US008048993B2

(12) United States Patent
Pecker et al.

(10) Patent No.: US 8,048,993 B2
(45) Date of Patent: *Nov. 1, 2011

(54) HEPARANASE SPECIFIC MOLECULAR PROBES AND THEIR USE IN RESEARCH AND MEDICAL APPLICATIONS

(75) Inventors: Iris Pecker, Rishon LeZion (IL); Israel Vlodavsky, Mevaseret Zion (IL); Yael Friedmann, Mevaseret Zion (IL); Tuvia Peretz, Hod Hasharon (IL)

(73) Assignees: InSight Biopharmaceuticals Ltd., Rehovot (IL); Hadasit Medical Research Services and Development Ltd., Jerusalem (IL)

( * ) Notice: Subject to any disclaimer, the term of this patent is extended or adjusted under 35 U.S.C. 154(b) by 401 days.

This patent is subject to a terminal disclaimer.

(21) Appl. No.: 12/003,999

(22) Filed: Jan. 4, 2008

(65) Prior Publication Data
US 2009/0099341 A1 Apr. 16, 2009

Related U.S. Application Data

(60) Continuation of application No. 10/676,079, filed on Oct. 2, 2003, now Pat. No. 7,339,038, which is a division of application No. 09/704,772, filed on Nov. 3, 2000, now Pat. No. 6,699,672, which is a division of application No. 09/322,977, filed on Jun. 1, 1999, now Pat. No. 6,531,129, which is a division of application No. 09/071,739, filed on May 1, 1998, now Pat. No. 6,177,545, which is a continuation-in-part of application No. 08/922,170, filed on Sep. 2, 1997, now Pat. No. 5,968,822.

(51) Int. Cl.
*C07K 16/00* (2006.01)
*C07K 16/40* (2006.01)
*C07K 14/00* (2006.01)
(52) U.S. Cl. .............. 530/387.1; 530/388.1; 530/388.26
(58) Field of Classification Search .................. None
See application file for complete search history.

(56) References Cited

U.S. PATENT DOCUMENTS

| 931,129 A | 8/1909 | Casse |
| 2,295,323 A | 9/1942 | Armstrong |
| 4,117,841 A | 10/1978 | Perrotta et al. |
| 4,455,296 A | 6/1984 | Hansen et al. |
| 4,683,195 A | 7/1987 | Mullis et al. |
| 4,859,581 A | 8/1989 | Nicolson et al. |
| 4,882,318 A | 11/1989 | Vlodavsky et al. |
| 4,937,747 A | 6/1990 | Koller |
| 4,946,778 A | 8/1990 | Ladner et al. |
| 5,061,689 A | 10/1991 | Alvarez |
| 5,129,877 A | 7/1992 | Gallo et al. |
| 5,145,679 A | 9/1992 | Hinson |
| 5,194,596 A | 3/1993 | Tischer et al. |
| 5,206,223 A | 4/1993 | Vlodavsky et al. |
| 5,332,812 A | 7/1994 | Nicolson et al. |
| 5,350,836 A | 9/1994 | Kopchick et al. |
| 5,360,735 A | 11/1994 | Weinshank et al. |
| 5,362,641 A | 11/1994 | Fuks et al. |
| 5,399,351 A | 3/1995 | Leshchiner et al. |
| 5,474,983 A | 12/1995 | Kuna et al. |
| 5,550,116 A | 8/1996 | Lormeau et al. |
| 5,571,506 A | 11/1996 | Regan et al. |
| 5,580,862 A | 12/1996 | Rosen et al. |
| 5,589,604 A | 12/1996 | Drohan et al. |
| 5,600,366 A | 2/1997 | Schulman |
| 5,602,095 A | 2/1997 | Pastan et al. |
| 5,618,709 A | 4/1997 | Gewirtz et al. |
| 5,656,595 A | 8/1997 | Schweighoffer et al. |
| 5,667,501 A | 9/1997 | Fowler et al. |
| 5,688,679 A | 11/1997 | Powell |
| 5,700,671 A | 12/1997 | Prieto et al. |
| 5,714,345 A | 2/1998 | Clark |
| 5,716,817 A | 2/1998 | Tornell |
| 5,736,137 A | 4/1998 | Anderson et al. |
| 5,739,115 A | 4/1998 | Fugedi et al. |
| 5,799,276 A | 8/1998 | Komissarchik et al. |
| 5,799,311 A | 8/1998 | Agrawal et al. |
| 5,830,759 A | 11/1998 | Chang et al. |
| 5,859,660 A | 1/1999 | Perkins et al. |
| 5,859,929 A | 1/1999 | Zhou et al. |
| 5,917,830 A | 6/1999 | Chen et al. |
| 5,962,321 A | 10/1999 | Gough et al. |
| 5,968,822 A | 10/1999 | Pecker et al. |

(Continued)

FOREIGN PATENT DOCUMENTS

| AU | 754228 | 11/1999 |
| AU | 735116 | 6/2001 |
| AU | 768820 | 1/2004 |
| EP | 0254067 | 1/1988 |
| EP | 0998569 | 5/2000 |
| EP | 1073682 | 5/2006 |
| JP | 04-187408 | 7/1992 |
| JP | 05-504047 | 7/1993 |
| JP | 05-509403 | 12/1993 |
| JP | 09-504422 | 5/1997 |

(Continued)

OTHER PUBLICATIONS

Mettenleiter et al. "Interaction of Glycoprotein GIII With a Cellular Heparinlike Substance Mediates Adsorption of Pseudorabies Virus", Journal of Virology, XP002503372, 64(1): 278-286, Jan. 1990. p. 281, r-h Col., § 1, 2.

(Continued)

*Primary Examiner* — Gerald R Ewoldt
*Assistant Examiner* — Marianne Dibrino

(57) ABSTRACT

According to the present invention there is provided an antibody that specifically binds an epitope of a heparanase protein, the heparanase protein including an amino acid sequence as set forth in SEQ ID NO:2, provided that phenylalanine replaces tyrosine at position 246. The present invention also provides an antibody elicited by an epitope of a heparanase protein, the heparanase protein including an amino acid sequence as set forth in SEQ ID NO:2, provided that phenylalanine replaces tyrosine at position 246.

12 Claims, 18 Drawing Sheets

U.S. PATENT DOCUMENTS

| | | | |
|---|---|---|---|
| 5,997,863 A | 12/1999 | Zimmermann et al. | |
| 6,020,931 A | 2/2000 | Bilbrey et al. | |
| 6,140,552 A | 10/2000 | Deboer et al. | |
| 6,153,187 A | 11/2000 | Yacoby-Zeevi | |
| 6,177,545 B1 * | 1/2001 | Pecker et al. | 530/387.3 |
| 6,190,875 B1 | 2/2001 | Ben-Artzi et al. | |
| 6,226,792 B1 | 5/2001 | Goiffon et al. | |
| 6,230,151 B1 | 5/2001 | Agrawal et al. | |
| 6,242,238 B1 | 6/2001 | Freeman et al. | |
| 6,307,965 B1 | 10/2001 | Aggarwal et al. | |
| 6,314,420 B1 | 11/2001 | Lang et al. | |
| 6,348,344 B1 | 2/2002 | Ayal-Hershkovitz et al. | |
| 6,387,643 B1 | 5/2002 | Heinrikson et al. | |
| 6,423,312 B1 | 7/2002 | Yacoby-Zeevi | |
| 6,426,209 B1 | 7/2002 | Ayal-Hershkovitz et al. | |
| 6,475,763 B1 | 11/2002 | Ayal-Hershkovitz et al. | |
| 6,531,129 B2 | 3/2003 | Pecker et al. | |
| 6,562,950 B2 | 5/2003 | Peretz et al. | |
| 6,664,105 B1 | 12/2003 | Pecker et al. | |
| 6,699,672 B1 | 3/2004 | Pecker et al. | |
| 6,790,658 B2 | 9/2004 | Pecker et al. | |
| 6,798,658 B2 | 9/2004 | Takedomi et al. | |
| 6,800,441 B2 | 10/2004 | Pecker et al. | |
| 6,946,131 B2 | 9/2005 | Peretz et al. | |
| 6,960,471 B2 | 11/2005 | Pecker et al. | |
| 6,986,996 B2 | 1/2006 | Pecker et al. | |
| 7,049,407 B2 | 5/2006 | Pecker et al. | |
| 2001/0006630 A1 | 7/2001 | Yacoby-Zeevi et al. | |
| 2002/0004585 A1 | 1/2002 | Pecker et al. | |
| 2002/0059202 A1 | 5/2002 | Hadzikadic et al. | |
| 2002/0064858 A1 | 5/2002 | Yacoby-Zeevi | |
| 2002/0068054 A1 | 6/2002 | Ilan et al. | |
| 2002/0068061 A1 | 6/2002 | Peretz et al. | |
| 2002/0088019 A1 | 7/2002 | Yacoby-Zeevi | |
| 2002/0102560 A1 | 8/2002 | Pecker et al. | |
| 2002/0102619 A1 | 8/2002 | Pecker et al. | |
| 2002/0114801 A1 | 8/2002 | Pecker et al. | |
| 2002/0119208 A1 | 8/2002 | Chajuss | |
| 2002/0168749 A1 | 11/2002 | Pecker et al. | |
| 2002/0194625 A1 | 12/2002 | Zcharia et al. | |
| 2003/0031660 A1 | 2/2003 | Yacoby-Zeevi et al. | |
| 2003/0068806 A1 | 4/2003 | Ayal-Hershkovitz et al. | |
| 2003/0082248 A1 | 5/2003 | Chajuss | |
| 2003/0161823 A1 | 8/2003 | Ilan et al. | |
| 2003/0163836 A1 | 8/2003 | Garofalo et al. | |
| 2003/0170860 A1 | 9/2003 | Pecker et al. | |
| 2003/0181687 A1 | 9/2003 | Peretz et al. | |
| 2003/0190737 A1 | 10/2003 | Pecker et al. | |
| 2003/0217375 A1 | 11/2003 | Zcharia et al. | |
| 2003/0236215 A1 | 12/2003 | Pecker et al. | |
| 2004/0063135 A1 | 4/2004 | Pecker et al. | |
| 2004/0142427 A1 | 7/2004 | Pecker et al. | |
| 2004/0146497 A1 | 7/2004 | Ilan et al. | |
| 2004/0146925 A1 | 7/2004 | Pecker et al. | |
| 2004/0170631 A1 | 9/2004 | Yacoby-Zeevi et al. | |
| 2004/0175371 A1 | 9/2004 | Yacoby-Zeevi | |
| 2004/0213789 A1 | 10/2004 | Yacoby-Zeevi et al. | |
| 2004/0229834 A1 | 11/2004 | Pecker et al. | |
| 2005/0260187 A1 | 11/2005 | Ilan et al. | |
| 2006/0008892 A1 | 1/2006 | Yacoby-Zeevi et al. | |
| 2006/0223108 A1 | 10/2006 | Pecker et al. | |
| 2006/0269552 A1 | 11/2006 | Yacoby-Zeevi et al. | |
| 2009/0099341 A1 | 4/2009 | Pecker et al. | |
| 2009/0275106 A1 | 11/2009 | Pecker et al. | |

FOREIGN PATENT DOCUMENTS

| | | |
|---|---|---|
| JP | 2000-502611 | 3/2000 |
| JP | 2002-510462 | 4/2002 |
| WO | WO 88/01280 | 2/1988 |
| WO | WO 91/02977 | 3/1991 |
| WO | WO 91/19197 | 12/1991 |
| WO | WO 92/01003 | 1/1992 |
| WO | WO 93/09718 | 5/1993 |
| WO | WO 93/18745 | 9/1993 |
| WO | WO 95/04158 | 2/1995 |
| WO | WO 97/11684 | 4/1997 |
| WO | WO 97/23345 | 7/1997 |
| WO | WO 97/27327 | 7/1997 |
| WO | WO 98/03638 | 1/1998 |
| WO | WO 98/46258 | 10/1998 |
| WO | WO 99/11798 | 3/1999 |
| WO | WO 99/18852 | 4/1999 |
| WO | WO 99/21975 | 5/1999 |
| WO | WO 99/40207 | 8/1999 |
| WO | WO 99/48478 | 9/1999 |
| WO | WO 99/57153 | 11/1999 |
| WO | WO 99/57244 | 11/1999 |
| WO | WO 00/03036 | 1/2000 |
| WO | WO 00/25817 | 5/2000 |
| WO | WO 00/52149 | 9/2000 |
| WO | WO 00/52178 | 9/2000 |
| WO | WO 01/00643 | 1/2001 |
| WO | WO 02/19962 | 3/2002 |
| WO | WO 02/32283 | 4/2002 |
| WO | WO 02/35350 | 5/2002 |
| WO | WO 03/006645 | 1/2003 |
| WO | WO 2004/108065 | 12/2004 |

OTHER PUBLICATIONS

Agrawal "Antisense Therapeutics: Is It as Simple as Complementary Base Recognition", Molecular Medicine Today, 6: 72-81, 2002.

Branch "A Good Antisense Molecule Is Hard to Find", Trends in Biochemical Sciences, 23(2): 45-50, 1998. Abstract.

Duff "Transgenic Mice Overexpressing Presenilin cDNAs: Phenotype and Utility in the Modeling of Alzheimer's Disease", Central Nervous System Diseases, p. 123-128, 2000. Abstract.

InSight "Monoclonal Anti-Human Heparanase 1 (HPA1) Antibody Clone HP130", InSight Biopharmaceuticals Ltd., 2 P., 2008.

InSight "Monoclonal Anti-Human Heparanase 1 (HPA1) Antibody Clone HP3/17", InSight Biopharmaceuticals Ltd., 2 P., 2008.

Kuyvenhoven et al. "Assessment of Serum Matrix Metalloproteinases MMP-2 and MMP-9 After Human Liver Transplantation: Increased Serum MMP-9 Level in Acute Rejection", Transplantation, 77(11): 1646-1652, 2004. Abstract.

Pontremoli et al. "Changes in Activity of Fructose-1,6-Bisphosphate Aldolase in Livers of Fasted Rabbits and Accumulation of Crossreacting Immune Material", Proc. Natl. Acad. Sci, USA, 76(12): 6323-6325, 1979.

Quax et al. "Metastatic Behavior of Human Melanoma Cell Lines in Nude Mice Correlates With Urokinase-Type Plasminogen Activator, Its Type-1 Inhibitor, and Urokinase-Mediated Matrix Degradation", The Journal of Cell Biology, 115(1): 191-199, 1991.

Savion et al. "Murine Macrophage Heparanase: Inhibition and Comparison With Metastatic Tumor Cells", Journal of Cellular Physiology, 130: 77-84, 1987.

Sordat et al. "Modulation of the Malignant Phenotype With the Urokinase-Type Plasminogen Activator and the Type 1 Plasminogen Activator Inhibitor", Cell Differentiation and Development, 32: 277-286, 1990.

Fux et al. "Structure-Function Approach Identifies A COOH-Terminal Domain That Mediates Heparanase Signalling", Cancer Research, 69(5): 1758-1767, Mar. 1, 2009.

Haisma et al. "A Monoclonal Antibody Against Human β-Glucurinodase for Application in Antibody-Directed Enzyme Prodrug Therapy", Hybridoma, 14(4): 377-382, 1995.

Ho "Activation of Human β-Glucuronidase by Murine Monoclonal Antibodies and Bovine Serum Albumin in An Uncompetitive Fashion", Biochemistry and Molecular Biology International, 36(6): 1277-1286, Aug. 1995.

Ho "Development and Optimization of An Enzyme-Linked Immunosorbent Asay Employing Two Murine Monoclonal Antibodies for Absolute Quantitation of Human β-Glucuronidase", Biotechnology and Applied Biochemistry, 16: 1-10, 1992.

Kasama et al. "Interleukin-10 Expression and Chemokine Regulation During the Evolution of Murine Type II Collagen-Induced Arthritis", Journal of Clinical Investigation, 95: 2868-2876, 1995.

Parren et al. "Two-in-One Designer Antibodies", Science, 323: 1567-1568, Mar. 20, 2009.

Paul et al. "Antigen-Antibody Interaction and Monoclonal Antibodies", Fundamental Immunology, 5th Ed., Chap.4: 86-89, 2003.

Payne "Progress in Immunoconjugate Cancer Therapeutics", Cancer Cell, 3: 207-212, Mar. 2003.
Wang et al. "A Single Amino Acid Determines Lysophospholipid Specificity of the S1P1 (EDG1) and LPA1 (EDG2) Phospholipid Growth Factor Receptors", The Journal of Biological Chemistry, 276(52): 49213-49220, Dec. 28, 2001.
International Search Report Dated Jan. 11, 1999 From the International Searching Authority Re.: Application No. PCTUS98/17954.
Agrawal "Antisense Oligonucleotides: Towards Clinical Trials", TIBTech, Trends in Biotechnology, 14: 376-387, 1996.
Alvarez-Dominguez et al. "Host Cell Heparian Sulfate Proteoglycans Mediate Attachment and Entry of Listeria Monocytogenes, and the Listerial Surface Protein ActA Is Involved in Heparan Sulfate Receptor Recognition", Infection & Immunity, 65(1): 78-88, 1997.
Anatolii "Hyaluronic Capsule as One of the Factors of Hemolytic Streptococcus Pathogenicity", Chemiocal Abstracts, 86(17): 339, 1977. Abstract 118714 in Zhurnal Mikrobiologii, Epidemiologii, i Immunobiologii, 2: 22-27, Feb. 1977. Abstract.
Aplin "Adhesion Molecules in Implantation", Reviews of Reproduction, 2(2): 84-93, 1997.
Asagoe et al. "Effect of Heparin on Infection of Cells by Equine Arteritis Virus", Journal of Veterinary Medical Science, 59(8): 727-728, 1997.
Aspenberg et al. "Dose-Dependent Stimulation of Bone Induction by Basic Fibroblast Growth Factor in Rats", Acta Orthopaedica Scandinavica, 62(5): 481-484, 1991. Abstract.
Aviezer et al. "Differential Structural Requirements of Heparin and Heparan Sulfate Proteoglycans That Promote Binding of Basic Fibroblast Growth Factor to Its Receptor", Journal of Biological Chemistry, 269(1): 114-121, 1994.
Azghani et al. "A Beta-Linked Mannan Inhibits Adherence of *Pseudomonas aeruginosa* to Human Lung Epithelial Cells", Glycobiology, 5(1): 39-44, 1995. Abstract.
Bartlett et al. "Comparative Analysis of the Ability of Leucocytes, Endothelial Cells, and Platelets to Degrade the Subendothelial Basement Membrane: Evidence for Cytokine Dependence and Detection of a Novel Sulfatase", Immunology & Cell Biology, 73: 113-124, 1995.
Benathan et al. "Living Epidermal and Dermal Substitutes for Treatment of Severely Burned Patients", Rev. Med. Suisse Romande, 118(2): 149-153, 1998. Abstract in French.
Bendayan "Possibilities of False Immunocytochemical Results Generated by the Use of Monoclonal Antibodies: The Example of the Anti-Proinsulin Antibody", Journal of Histochemistry and Cytochemistry, 43(9): 881-886, 1995.
Bendig et al. "Humanization of Rodent Monoclonal Antibodies by CDR Grafting", Methods: A Companion to Methods in Enzymology, 8: 83-93, 1995.
Benezra et al. "Antiproliferative Activity to Vascular Smooth Muscle Cells and Receptor Binding of Heparain-Mimicking Polyaromatic Anionic Compounds", Arteriosclerosis, Thrombosis, and Vascular Biology, 14(12): 1992-1999, 1993.
Benezra et al. "Reversal of Fibroblast Growth Factor-Mediated Autocrine Cell Transformation by Aromatic Anionic Compounds", Cancer Research, 52: 5656-5662, 1992.
Benjamin et al. "A Plasticity Window for Blood Vessel Remodelling Is Defined by Pericyte Coverage of the Preformed Endothelial Network and Is Regulated by PDGF-B and VEGF", Development, 125: 1591-1598, 1998.
Beuth et al. "Lectin-Mediated Bacterial Adhesion to Human Tissue", European Journal of Clinical Microbiology, 6(5): 591-593, 1987. Abstract.
Bischof et al. "The Regulation of Endometrial and Trophoblastic Metalloproteinases During Blastocyst Implantation", Contraception, Fertilité, Sexualité, 22(1): 48-51, 1994. Abstract. Article in French.
Blanquaert et al. "CMDBS, Functional Analogs of Sulfate Heparanes, Used as Osseous Cicatrizing Agents", Annales Endocrinologie, 55(2): 121-123, 1994. Abstract.
Boat et al. "Epithelial Cell Dysfunction in Cystic Fibrosis: Implications for Airways Disease", Acta Paediatrica Scandinavica Supplement, 363: 25-29, 1989.

Bost et al. "Antibodies Against A Peptide Sequence Within the HIV Envelope Protein Crossreacts With Human Interleukin-2", Immunological Investigations, 17(6-7): 577-586, Aug.-Oct. 1988.
Boucher et al. "Mucoid *Pseudomonas aeruginosa* in Cystic Fibrosis: Characterization of Muc Mutations in Clinical Isolates and Analysis of Clearance in a Mouse Model of Respiratory Infection", Infection and Immunity, 65(9): 3838-3846, 1997.
Boucher et al. "Two Distinct Loci Affecting Conversion to Mucoidy *Pseudomonas aeruginosa* in Cystic Fibrosis Encode Homologs of the Serine Protease HtrA", Journal of Bacteriology, 178(2): 511-523, 1996.
Brenner "Errors in Genome Annotation", Trends in Genetics, 15(4): 132-133, 1999.
Calabretta et al. "Normal and Leukemic Hematopoietic Cell Manifest Differential Sensitivity to Inhibitory Effects of C-Myc Antisense Oligodeoxynucleotides: An In Vitro Study Relevant to Bone Marrow Purging", Proc. Natl. Acad. Sci. USA, 88: 2351-2355, 1991.
Campbell "General Properties and Applications of Monoclonal Antibodies", Monoclonal Antibody Technology, Laboratory Techniques in Biochemistry & Molecular Biology, 13(Chap.1): 1-32, 1984.
Campbell et al. "Comparison of the Whey Acidic Protein Genes of the Rat and Mouse", Nucleic Acids Research, 12(22): 8685-8697, 1984.
Carlone et al. "Embryonic Modulation of Basic Fibroblast Growth Factor in the Rat Uterus", Biology of Reproduction, 49(4): 653-665, 1993.
Carpentier et al. "DNA Vaccination With HuD Inhibits Growth of a Neuroblastoma in Mice", Clinical Cancer Research, 4: 2819-2824. 1998.
Chase et al. "Respiratory Mucous Secretions in Patients With Cystic Fibrosis: Relationship Between Levels of Highly Sulfated Mucin Component and Severity of the Disease", Clinica Chimica Acta, 132(2): 143-155, 1983. Abstract.
Chen et al. "Dengue Virus Infectivity Depends on Envelope Protein Binding to Target Cell Heparan Sulfate", Nature Medicine, 3(8): 866-871, 1997. Abstract.
Cheng et al. "Increased Sulfation of Glycoconjugates NY Cultured Nasal Epithelial Cells From Patients With Cystic Fibrosis", The Journal of Clinical Investigation, 84(1): 68-72, 1989.
Colman "Effects of Amino Acid Sequence Changes on Antibody-Antigen Interactions", Research in Immunology, 145(1): 33-36. 1994.
Coombe et al. "Analysis of the Inhibition of Tumor Metastasis by Sulphated Polysaccharides", International Journal of Cancer, 39: 82-88, 1987. Abstract.
Crystal "Gene Therapy Strategies for Pulmonary Disease", American Journal of Medicine, 92 (Suppl.64): 6A-44S-6A-52S, 1992.
Dasgupta et al. "Reduction in Viscoelasticity in Cystic Fibrosis Sputum In Vitro Using Combined Treatment With Nacystelyn and RhDNase", Pediatric Pulmonology, 22: 161-166, 1996.
De Vouge et al. "Immunoselection of GRP94/Endoplasmin From A KNRK Cell-Specific λgt11 Library Using Antibodies Directed Against a Putative Heparanase Amino-Terminal Peptide", International Journal Cancer, 56: 286-294, 1994.
Dibrino "RT-PCR Method & Applications", Clonotech Laboratories, 1st Ed., 1: 11, 15, 23, 41, 26, 1991.
Doetschman "Interpretation of Phenotype in Genetically Engineered Mice", Laboratory Animal Science, 49(2): 137-143, 1999.
Durand et al. "Active-Site Motifs of Lysosomal Acid Hydrolases: Invariant Features of Clan GH-A Glycosyl Hydrolases Deduced From Hydrophobic Cluster Analysis", Glycobiology, 7(2): 277-284, 1997.
Farndale et al. "A Direct Spectrophotometric Microassay for Sulfated Glycosaminoglycans in Cartilage Cultures", Connective Tissue Research, 9: 247-248, 1982.
Finkel "Potential Target Found for Antimetastasis Drugs", Science, 285: 33-34, 1999.
Flanagan et al. "Potent and Selective Gene Inhibition Using Antisense Oligodeoxynucleotides", Molecular and Cellular Biochemistry, 172: 213-225, 1997.
Freeman et al. "A Rapid Quantitative Assay for the Detection of Mammalian Heparanase Activity", Biochemical Journal, 325: 229-237, 1997.

Freeman et al. "Evidence That Platelet and Tumour Heparanases Are Similar Enzymes", Biochemical Journal, 342: 361-368, 1999. Suppl. IDS in 25783.

Friedman et al. "Regulated Expression of Homeobox Genes Msx-1 and Msx-2 in Mouse Mammary Gland Development Suggests a Role in Hormone Action and Epithelial-Stromal Interactions", Developmental Biology, 177: 347-355, 1996.

Gabriel et al. "In Vitro Adherence of *Pseudomonas aeruginosa* to Four Intraocular Lenses", Journal of Cataract and Refractive Surgery, 24: 124-129, 1998. Abstract.

Gewirtz et al. "Facilitating Oligonucleotide Delivery: Helping Antisense Deliver on Its Promise", Proc. Natl. Acad. Sci. USA, 93: 3161-3163, 1996.

Gewirtz et al. "Nucleic Acid Therapeutics: State of the Art and Future Prospects", Blood, 92(3): 712-736, 1998.

Gilat et al. "Molecular Behaviour Adapts to Context: Heparanase Functions as an Extracellular Matrix-Degrading Enzyme or as a T-Cell Adhesion Molecule, Depending on the Local PH", Journal of Experimental Medicine, 181: 1929-1934, 1995.

Giuffrè et al. "Monocyte Adhesion to Activated Aortic Endothelium: Role of L-Selectin and Heparan Sulfate Proteoglycans", The Journal of Cell Biology, 136(4): 945-956, 1997.

Gorodetsky et al. "Isolation and Characterization of the Bos Taurus β-Casein Gene", Gene, 66: 87-96, 1988. Abstract.

Goshen et al. "Purification and Characterization of Placental Heparanase and Its Expression by Cultured Cytotrophoblasts", Molecular Human Reproduction, 2(9): 679-684, 1996.

Graham et al. "Comparison of the Heparanase Enzymes From Mouse Melanoma Cells, Mouse Microphages, and Human Platelets", Biochemistry and Molecular Biology International, 39(3): 563-571, 1996. Abstract.

Hagiwara et al. "Inhibitory Effect of Heparin on Red Blood Cell Invasion by Theileria Sergenti Merozoites", International Journal of Parasitology, 27(5): 535-539, 1997. Abstract.

Haimovits-Friedman et al, "Activation of Platelet Heparitinase by Tumor Cell-Derived Factors", Blood, 78(3): 789-796, 1991.

Haisma et al. "A Monoclonal Antibody Against Human β-Glucurinodase for Application in Antibody-Directed Enzyme Prodrug Therapy", Hybridoma, 14(4): 377-382, 1995.

Haisma et al. "Construction and Characterization of a Fusion Protein of Single-Chain Anti-Carcinoma Antibody 323/A3 and Human Beta-Glucuronidase", Cancer Immunology, Immunotherapy, 45(5): 266-272, 1998.

Hatano et al. "Biologic Activities of Antobodies to the Neutral-Polysaccharide Component of the *Pseudomonas aeruginosa* Lipopolysaccharide Are Blocked by O Side Chains and Mucoid Exopolysaccharide (Alginate)", Infection and Immunity, 63(1): 21-26, 1995.

Herrera et al. "Mediation of *Trypanosoma cruzi* Invasion by Heparan Sulfate Receptors on Host Cells and Penetrin Counter-Receptors on the Trypanosomes", Molecular & Biochemical Parasitology, 65(1): 73-83, 1994. Abstract.

Hill et al. "Organ-Specific Over-Sulfation of Glycosaminoglycans and Altered Extracellular Matrix in a Mouse Model of Cystic Fibrosis", Biochemical and Molecular Medicine, 62(1): 113-122, 1997. Abstract.

Ho "Activation of Human β-Glucuronidase by Murine Monoclonal Antibodies and Bovine Serum Albumin in an Uncompetitive Fashion", Biochemistry and Molecular Biology International, 36(6): 1277-1286, Aug. 1995.

Hormuzdi et al. "A Gene-Targeting Approach Identifies a Function for the First Intron in Expression of the α1(I) Collagen Gene", Molecular and Cellular Biology, 18(6): 3368-3375, Jun. 1998.

Hsuch et al. "Invasive Streptococci Pneumoniae Infection Associated With Rapidly Fatal Outcome in Taiwan", Journal of the Formosan Medical Association, 95(5): 364-371, 1996. Abstract.

Imai et al. "Osteoblast Recruitment and Bone Formation Enhanced by Cell Matrix-Associated Heparin-Binding Growth-Associated Molecule (HB-GAM)", The Journal of Cell Biology, 143(4): 1113-1128, Nov. 16, 1998.

Inoue et al. "Selective N-Desulfation of Heparin With Dimethyl Sulfoxide Containing Water or Methanol", Carbohydrate Research, 46(1): 87-95, Jan. 1976.

Irimura et al. "Chemically Modified Heparins as Inhibitors of Heparan Sulfate Specific Endo-Bela-Glucuronidase (Heparanase) of Metastatic Melanoma Cells", Biochemistry, 25: 5322-5328, 1986. Abstract.

Jin et al. "Molecular Cloning and Expression of Human Heparanase cDNA", Proceedings American Association for Cancer Research Annual Meeting, 1992, 33: 57, 1992. Abstract.

Johansen et al. "Vaccination Promotes TH1-Like Inflammation and Survival in Chronic *Pseudomonas aeruginosa* Pneumonia: A New Prophylactic Principle", Behring Institut Mitteilungen, 98: 269-273, 1997. Abstract.

Jusa et al. "Effect of Heparinon on Infection of Cells by Porcine Reproductive and Respiratory Syndrome Virus", American Journal of Veterinary Research, 58(5): 488-491, 1997. Abstract.

Kang et al. "Prolactin-Inducible Enhancer Activity of the First Intron of the Bovine Beta-Casein Gene", Molecules and Cells, 8(3): 259-265, 1998. Abstract.

Kato et al. "Physiological Degradation Converts the Soluble Syndecan-1 Ectodomain From an Inhibitor to a Potent Activator of FGF-2", Nature Medicine, 4(6): 691-697, 1998.

Köhler et al. "Continuous Cultures of Fused Cells Secreting Antibody of Predefined Specificity", Nature, 256: 495-497, 1975.

Konstan et al. "Current Understanding of the Inflammatory Process in Cystic Fibrosis", Pediatric Pulmonology, 24: 137-142, 1997.

Konstan et al. "Patterns of Medical Practice in Cystic Fibrosis: Part II. Use of Therapies", Pediatric Pulmonology. 28(4): 248-54, 1999. Abstract.

Krivit et al. "Microglia: The Effector Cell for Reconstitution of the Central Nervous System Following Bone Marrow Transplantation for Lysosomal and Peroxisomal Storage Diseases", Cell Transplantation, 4(4): 385-392, 1995. Abstract.

Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.

Krusat et al. "Heparin-Dependent Attachment of Respiratory Syncytial Virus (RSV) to Host Cells", Archives of Virology, 142(6): 1247-1254, 1997. Abstract.

Lai et al. "DNA Vaccines", Critical Reviews in Immunology, 18: 449-484, 1998.

Lai et al. "Homologous Recombination Based Gene Therapy", Experimental Nephrology, 7(1):11-14, 1999. Abstract.

Laskov et al. "Production of Heparanase by Normal and Neoplastic Murine—B-Lymphocytes", International Journal of Cancer, 47(1): 92-98, 1991.

Lazarus et al. "Ex Vivo Expansion and Subsequent Infusion of Human Bone Marrow-Derived Stromal Progenitor Cells (Mesenchymal Progenitor Cells): Implications for Therapeutic Use", Bone Marrow Transplantation, 16(4): 557-564, 1995. Abstract.

Le Fur et al. "Selective Increase in Specific Alternative Splice Variants of Tyrosinase in Murine Melanomas: A Projected Basis for Immunotherapy", Proc. Natl. Acad. Sci. USA, 94: 5332-5337, 1997.

Lederman et al. "A Single Amino Acid Substitution in a Common African Allele of the CD4 Molecule Ablates Binding of the Monoclonal Antibody, OKT4", Molecular Immunology, 28: 1171-1181, 1991.

Leong et al. "Different Classes of Proteoglycans Contribute to the Attachment of *Borrelia burgdorferi* to Cultured Endiothelial and Brain Cells", Infection and Immunity, 66(3): 994-999, 1998.

Lider et al. "Suppression of Experimental Autoimmune Diseases and Prolongation of Allograft Survival by Treatment of Animals With Low Doses of Heparins", Journal of Clinical Investigations, 83: 752-756, Mar. 1989.

Linhardt et al. "Polysaccharide Lyases", Applied Biochemistry and Biotechnology, 12: 135-176, 1986.

Luft "Making Sense Out of Antisense Oligodeoxynucleotide Delivery: Getting There Is Half the Fun", Journal of Miolecular Medicine, p. 75-76. 1998.

Marchetti et al. "Neurotrophin Stimulation of Human Melanoma Cell Invasion: Selected Enhancement of Heparanase Activity and Heparanase Degradation of Specific Heparan Sulfate Subpopulations", Cancer Research, 56: 2856-2863, 1996. Also in: Advances in Enzyme Regulation, 37: 111-134, 1997.

Marty et al. "Influence of Nutrient Media on the Chemical Composition of the Expolysaccharide From Mucoid and Non-Mucoid *Pseudomonas aeruginosa*", FEMS Microbiology Letters, 77(1-3): 35-44, 1992. Abstract.

Mateo et al. "Humanization of a Mouse Monoclonal Antibody That Blocks the Epidermal Growth Factor Receptor: Recovery Antagonistic Activity", Immunotechnology, 3: 71-81, 1997. Abstract.

Matoba et al. "Evaluation of Omental Implantation for Perforated Gastric Ulcer Therapy: Findings in a Rat Model", Journal of Gastroenterology, 31(6): 777-784, 1996. Abstract.

Meluleni et al. "Mucoid *Pseudomonas aeruginosa* Growing in a Biofilm In Vitro Are Killed by Opsonic Antibodies to the Mucoid Exopolysaccharide Capsule But Not by Antibodies Produced During Chtonic Lung Infection in Cystic Fibrosis Patients". Journal of Immunology, 155(4):2029-2038, 1995. Abstract.

Miao et al. "Modulation of Fibroblast Growth Factor-2 Receptor Binding Dimerization, Signaling, and Angiogenic Activity by a Synthetic Ileparain-Mimicking Polyaromatic Compound", Journal of Clinical Invesigation, 99(7): 1565-1575, 1997.

Mohapatra et al. "Alteration of Sulfation of Glycoconjugates, But Not Sulfate Transport and Intracellular Inorganic Sulfate Content in Cystic Fibrosis Airway Epithelial Cells", Pediatric Research, 38(1): 42-48, Jul. 1995. Abstract.

Mollinedo et al. "Major Co-Localization of the Extracellular-Matrix Degradative Enzymes Heparanase and Gelatinase in Tertiary Granules of Human Neutrophils", Biochemical Journal, 327: 917-923, 1997.

Moses et al. "Relative Contributions of Hyaluronic Capsule and M Protein to Virulence in a Mucoid Strain of the Group A Streptococcus", Infection and Immunity, 65(1): 64-71, Jan. 1997.

Mrsny "Distribution of DNA and Alginate in Purulent Cystic Fibrosis Sputum: Implications to Pulminary Targeting Strategies", Journal of Drug Targeting, 4(4): 233-243, 1996.

Murray et al. "The Extracellular Matrix", Harper's Biochemistry, McGraw-Hill Professional, 24th Ed., Chap.57, p. 667-685, 1998.

Nagasawa et al. "Solvolytic Desulfation of Glycosaminoglycuronan Sulfates With Dimethyl Sulfoxide Containing Water or Methanol", Carbohydrate Research, 58(1): 47-55, Sep. 1977. Abstract.

Nakajima "Heparanases and Tumor Metastasis", Tanpakushitsu Kakusan Koso, 37(11): 1753-1758, 1992. Abstract.

Nakajima et al. "A Solid-Phase Substrate of Heparanase: Its Application to Assay of Human Melanoma for Heparan Sulfate Degradative Activity", Analytical Biochemistry, 157: 162-171, 1986. Abstract.

Nakajima et al. "Heparanases and Tumor Metastasis", Journal of Cellular Biochemistry, 36(2): 157-167, 1988.

Ngo et al. "Computational Complexity, Protein Structure Prediction, and the Levinthal Paradox", The Protein Folding Problem and Tertiary Structure Prediction, Birkhauser, Boston, p. 433, 492-495, 1994.

Nicolson "Organ Specificity of Tumor Metastis: Role of Preferential Adhesion, Invasion and Growth of Malignant Cells at Specific Secondary Sites", Cancer Metastasis Reviews, 7(2): 143-188, Jun. 1988. Abstract.

Novagen "PET System Manual", Novagen, 6th Ed., p. 11, 1995.

Oosta et al. "Purification and Properties of Iluman Platelets Ileparitanase", The Journal of Biological Chemistry, 257(19): 11249-11255, 1982.

Pier et al. "How Mutant CFTR May Contribute to *Pscudomonas acruginosa* Infection in Cystic Fibrosis", American Journal of Respiratory and Critical Care Medicine, 154(4): S175-S182, 1996. Abstract.

Pomahac et al. "Tissue Engineering of Skin", Crit. Rev. Oral Biol. Med., 9(3): 333-344, 1998. Abstract.

Prahalada et al. "Diethylstilbestrol-Induced Cervical and Vaginal Adenosis Using the Neonatal Mouse Model", Biology of Reproduction, 38: 935-943, 1988. Abstract.

Reddi "Role of Morphogenetic Proteins in Skeletal Tissue Engineering and Regeneration", Nature Biotechnology, 16: 247-252, 1998.

Regan et al. "Mimicry of Biological Macromolecules by Polyaromatic Anionic Compounds", Journal of Bioactive and Compatible Polymers, 8(4): 317-337, 1993. Abstract.

Richards et al. "Construction and Preliminary Characterization of the Rat Casein and Alpha-Lactalbumin cDNA Clones", Journal of Biological Chemistry, 256(1): 526-32, 1981.

Ricoveri et al. "Heparan Sulfate Endoglycosidase and Metastatic Potential in Murine Fibrosarcoma and Melanoma", Cancer Research, 46(8): 3855-3861, 1986. Abstract.

Robert et al. "Chondroitin-4-Sulphate (Proeoglycan), A Receptor for Plasmodium Falciparum-Infected Erthrocyte Adherence on Brain Microvascular Endothelial Cells", Research in Immunology, 146(6): 383-393, 1995. Abstract.

Romanos "Advances in the Use of Pichia Pusteris for High-Level Gene Expression", Current Opinion in Biotechnology, 69(5): 527-533, 1995. Abstract.

Sasisekharan et al. "Heparinase Inhibits Neovascularization", Proc. Natl. Acad.Sci. USA, 91: 1524-1528, 1994.

Savitsky et al. "Ataxia-Telangiectasia: Structural Diversity of Untranslated Sequences Suggests Complex Post-Transcriptional Regulation of ATM Gene Expression", Nucleic Acids Research, 25(9): 1678-1684, 1997.

Schultz et al. "Growth Factors in Preimplantation Mammalian Embryos", Oxford Review of Reproduction in Biology, 15: 43-81, 1993. Abstract.

Schwab et al. "Increased Adherence of Staphylococcus Aures From Cystic Fibrosis Lungs to Airway Epithelial Cells", The American Review of Respiratory Disease, 148(2): 365-369, 1993. Abstract.

Sewell et al. "Human Mononuclear Cells Contain an Endoglycosidase Specific for Heparan Sulfate Glycosaminoglycan Demonstrable With the Use of a Specific Solid-Phase Metabolically Radiolabelled Substrate", Biochemical Journal, 264: 777-783, 1989.

Shakibaei et al. "Dual Interaction of the Malaria Circumsporozoite Protein With the Low Density Lipoprotein Receptor-Related Protein (LRP) and Heparan Sulfate Proteoglycans", Journal of Experimental Medicine, 184(5): 1699-1711, 1996.

Shastry "Gene Disruption in Mice: Models of Development and Disease", Molecular and Cellular Biochemistry, 181: 163-179, 1998.

Shekhar et al. "Correlation of Differences in Modulation of Ras Expression With Metastatic Competence of Mouse Mammary Tumour Subpopulations", Invasion Metastasis, 14: 27-37, May 1994.

Shich et al. "Cell Surface Receptors for Herpes Simplex Virus Are Heparan Sulfate Proteoglycan Proteoglycans", The Journal of Cell Biology, 116(5): 1273-1281, Mar. 1992.

Shimazu et al. "Syndecan-3 and the Control of Chondrocyte Proliferation During Endochondral Ossification", Exp. Cell. Res., 229(1): 126-136, 1996. Abstract.

Smith et al. "Expression of Heparan Sulfate Protoglycan (Perlecan) in the Mouse Blastocyst Is Regulated During Normal and Delayed Implantation", Developmental Biology, 184(1): 38-47, 1997. Abstract.

Smith et al. "The Challenges of Genome Sequence Annotation or 'The Devil Is in the Details'", Nature Biotechnology, 15: 1222-1223, 1997.

Spencer "Invasive Streptococci", European Journal of Clinical Microbiology & Infectious Diseases, 14(Suppl. 1): S26-S32, 1995. Abstract.

Stickler et al. "An Assessment of the Ability of a Silver-Releasing Device to Prevent Bacterial Contamination of Urethral Catheter Drainage Systems", British Journal of Urology, 78(4): 579-588, Oct. 1996.

Stracke et al. "Autotaxin, Tumor Motility-Stimulating Exophosphodiesterase", Advances in Enzyme Regulation, 37: 135-144, 1997. Introduction.

Sudhalter et al. "Importance of Size, Sulfation and Anticoagulant Activity in the Potentiation of Acidic Fibroblast Growth Factor by Heparin", The Journal of Biological Chemistry, 254(12): 6892-6897, Apr. 25, 1989.

Suggs et al. "Use of Synthetic Oligonucleotides as Hybridization Probes: Isolation of Cloned cDNA Sequences for Human β2-Microglobulin", Proc. Natl. Acad. Sci. USA, 78(11): 6613-6617, 1981. p. 6613.

Sutherland "Structure-Function Relationships in Microbial Exopolysaccharides", Biotechnology Advances, 12: 393-448, 1994.

Szczylik et al. "Selective Inhibition of Leukemia Cell Proliferation by BCR-ABL Antisense Oligodeoxynucleotides", Science, 253: 562-565, 1991. Abstract.

Trowbridge et al. "CD45: An Emerging Role as a Protein Tyrosine Phosphate Required for Lymphocyte Activation and Development.", Annual Reviews of Immunology, 12: 85-116, Apr. 1994.

Vlodaysky et al. "Endothelial Cell-Derived Basic Fibroblast Growth Factor: Synthesis and Deposition Into Subendothelial Extra-Cellular Matrix", Proc. Natl. Acad. Sci. USA, 84: 2292-2296, 1987.

Vlodavsky et al. "Expression of Heparanase by Platelets and Circulating Cells of the Immune System: Possible Involvement in Diapedesis and Extra Vasation", Invasion & Metastasis, 12(2): 112-127, 1992. Abstract.

Vlodavsky et al. "Extracellular Sequestration and Release of Fibroblast Growth Factor: A Regulatory Mechanism?", Trends in Biomedical Sciences, 16: 268-271, 1991. Abstract.

Wall "Transgenic Livestock: Progress and Prospects for the Future", Theriogenology, 45: 57-68, 1996.

Walton et al. "Prediction of Antisense Oligonucleotide Binding Affinity to A Structured RNA Target", Biotechnology and Bioengineering, 65(1): 1-9, 1999.

Wang "Basic Fibroblast Growth Factor for Stimulation of Bone Formation in Osteoinductive or Conductive Implants", Acta Orthopaedica Scandinavica Supplement, 269: 1-33, 1996. Abstract.

Wang "Basic Fibroblast Growth Factor Infused at Different Times During Bone Graft Incorporation. Titanium Chamber Study in Rats", Acta Orthopaedica Scandinavica, 67(3): 229-236, 1996. Abstract.

Wang et al. "Basic Fibroblast Growth Factor Enhances Bone-Graft Incorporation: Dose and Time Dependence in Rats", Journal of Orthopaedic Research,14(2): 316-323, 1996. Abstract.

Webster et al. "FGFR Activation in Skeletal Disorders: Too Much of a Good Thing", TIG, 13(5): 178-182, 1997.

Welch et al. "Expression of Ribozymes in Gene Transfer Systems to Modulate Target RNA Levels", Current Opinion in Biotechnology, 9(5): 486-496, 1998. Abstract.

Weller "Implications of Early Inflamation and Infection in Cystic Fibrosis: A Review of New and Potential Interventions", Pediatric Pulmonology, 24: 143-146, 1997.

Wessels et al. "Effects on Virulence of Mutations in a Locus Essential for Hyaluronic Acid Capsule Expression in Group A Streptococci", Infection and Immunity, 62(2): 433-441, 1994.

Wiils et al. "Short-Term Recombinant Human DNase in Bronchiectasis. Effect on Clinical State and In Vitro Sputum Transportability", American Journal of Respiratory and Critical Care Medicine, 154(2/Pt1): 413-417, Aug. 1996. Abstract.

Wordinger et al. "The Immunolocalzation of Basic Fibroblast Growth Factor in the Mouse Uterus During the Initial Stages of Embryo Implantation", Growth Factors, 11(3): 175-186, 1994. Abstract.

Yagel et al. "Normal Nonmetastatic Human Trophoblast Cells Share In Vitro Invasive Properties of Malignant Cells", Journal of Cellular Physiology, 136: 455-462, 1988.

Yayon et al. "Cell Surface, Heparin-Like Molecules Are Required for Binding of Basic Fibroblast Growth Factor to its High Affinity Receptor", Cell, 64: 841-848, 1991.

Ye et al. "Targeted Gene Correction: A New Strategy for Molecular Medicine", Molecular Medicine Today, p. 431-437, 1998.

Yesildaglar et al. "The Mouse as a Model to Study Adhesion Formation Following Endoscopic Surgery: A Preliminary Report", Human Reproduction, 14(1): 55-59, 1999. Abstract.

Ying et al. "Alginate, the Slime Exopolysaccharide of Pseudomonas aeruginosa, Binds Human Leukocyte Elastase, Retards Inhibition by Alpha 1-Proteinase Inhibitor, and Accelerates Inhibition by Secretory Leukoprotease Inhibitor", American Journal of Respiratory Cell and Molecular Biology, 15(2): 283-291, Aug. 1996. Abstract.

Zahm et al. "Early Alterations in Airway Mucociliary Clearance and Inflamation of the Lamina Propria in CF Mice", AJP—American Journal of Physiology—Cell Physiology, 272(3 Pt 1): C853-C859, 1997. Abstract.

Zheng et al. "Increment of hFIX Expression With Endogenous Intron 1 In Vitro", Cell Research, 7(1):21-29, 1997 Abstract.

Zhou et al. "HFE Gene Knockout Produces Mouse Model of Hereditary Hemochromatosis", PNAS, 95(5): 2492-2497, 1998.

Response Dated Oct. 26, 2010 to Communication Pursuant to Article 94(3) EPC of Aug. 17, 2010 From the European Patent Office Re. Application No. 04018465.7.

Abaza et al. "Effects of Amino Acid Substitutions Outside an Antigenic Site on Protein Binding to Monoclonal Antibodies of Predetermined Specificity Obtained by Peptide Immunization: Demonstration With Region 94-100 (Antigenic Site 3) of Myoglobin", Journal of Protein Chemistry, 11(5): 433-444, 1992.

Abrahamsohn et al. "Implantation and Decidualization in Rodents", Journal of Experimental Zoology, 266(6): 603-628, 1993. Abstract.

Adams et al. "Initial Assessment of Human Gene Diversity and Expression Patterns Based Upon 83 Million Nucleotides of cDNA Sequence", Nature, 377(6547): 3-174, 1995. GenBank Entry AA304653, 1997.

Albus et al. "Staphylococcus Aureus Capsular Types and Antibody Response to Lung Infection in Patients With Cystic Fibrosis", Journal of Clinical Microbiology, 26(12): 2505-2509, 1988. Abstract.

Alexander et al. "Complete Sequence of the Bovine β-Lactoglobulin cDNA", Nucleic Acids Research, 17(16): 6739-6744, 1989.

Allen "Opportunities for the Use Aerosolized α1—Antitrypsin for the Treatment of Cystic Fibrosis", Chest, 110: 256S-260S, 1996.

Allison et al. "Polysaccharide Production in Pseudomonas Cepacia", Journal of Basic Microbiology, 34(1): 3-10, 1994. Abstract.

Anatolii "Hyaluronic Capsule as One of the Factors of Hemolytic Streptococcus Pathogenicity", Chemical Abstracts, 86(17): 339, 1977. Abstract 118714 in Zhurnal Mikrobiologii, Epidemiologii, i Immunobiologii, 2: 22-27, Feb. 1977. Abstract.

Aoki et al. "In Vivo Transfer Efficiency of Antisense Oligonucleotides Into the Myocardium Using HVJ-Liposome Method", Biochemical and Biophysical Research Communications, 231: 540-545, 1997.

Armstrong et al. "Lower Airway Inflammation in Infants and Young Children With Cystic Fibrosis", American Journal of Respiratory and Critical Care Medicine, 156(4 Pt.1): 1197-1204, 1997.

Aspenberg et al. "Fibroblast Growth Factor Stimulates Bone Formation. Bone Induction Studied in Rats", Acta Orthopaedica Scandinavica, 60(4): 473-476, 1989. Abstract.

Bame "Heparanases: Endoglycosidases That Degrade Heparan Sulfate Proteoglycans", Glycobiology, 11(6): 91R-98R, 2001.

Barghouthi et al. "Nonopsonic Phagocytosis of Pseudomonas aeruginosa Requires Facilitated Transport of D-Glucose by Macrophages", The Journal of Immunology, 154(7): 3420-3428, 1995. Abstract.

Bar-Ner et al. "Inhibition of Heparanase-Mediated Degradation of Extracellular Matrix Heparan Sulphate by Non-Anticoagulant Heparin Species", Blood, 70(2): 551-557, 1987. Abstract.

Basu et al. "Analysis of Glycospingolipids by Fluorophore-Assisted Carbohydrate Electrophoresis Using Ceramide Glycanase From Mercenaria Mercenaria", Analytical Biochemistry, 222: 270-274, 1994.

Bean et al. "Fertilization In Vitro Increases Non-Disjunction During Early Cleavage Divisions in a Mouse Model System", Human Reproduction, 17(9): 2362-2367, 2002. Abstract.

Benezra et al. "Thrombin Enhances the Degradation of Heparan Sulfate in the Extracellular Matrix by Tumor Cell Heparanase", Experimental Cell Research, 201: 208-215, Jul. 1992.

Bennett et al. "Effect of Uridine 5'-Triphosphate Plus Amiloride on Mucociliary Clearance in Adult Cystic Fibrosis", American Journal of Respiratory and Critical Care Medicine, 153(6 Pt.1): 1796-1801, 1996. Abstract.

Berkow "The Merck Manual", Merck Research Laboratories, p. 201, 204, 1308, 177-179, 1016-1017, 194-197, 885, 601, 1997.

Bhaskar et al. "Dysregulation of Proteoglycan Production by Intraheptic Biliary Epithelial Cells Bearing Defective (Delta-f508) Cystic Fibrosis Transmembrane Conductance Regulator", Hepatology, 27(1): 7-14, 1998. Abstract.

Bischof et al. "The Regulation of Endometrial and Trophoblastic Metalloproteinases During Blastocyst Implantation", Contraception, Fertilit, Sexualit, 22(1): 48-51, 1994. Abstract. Article in French.

Blanquaert et al. "Heparan-Like Molecules Induce the Repair of Skull Defects", Bone, 17(6): 499-506, 1995. Abstract.

Boat et al. "Biochemistry of Airway Mucus Secretions", Federation Proceedings, 39(13): 3067-3074, 1980. Abstract.

Bork "Go Hunting in Sequence Databases But Watch Out for the Traps", Trends in Genetics, 12(10): 425-427, 1996.
Bork "Powers and Pitfalls in Sequence Analysis: The 70% Hurdle", Genome Research, 10 : 398-400, 2000.
Bowie et al. "Deciphering the Message in Protein Sequences: Tolerance to Amino Acid Substitutions", Science, 247: 1306-1310, 1990.
Brinster et al. "Restoration of Fertility by Germ Cell Transplantation Requires Effective Recipient Preparation", Biology of Reproduction, 69: 412-420, 2003.
Burch et al. "Oligodeoxynucleotides Antisense to the Interleukin 1 Receptor mRN Block the Effects of Interleukin 1 in Cultured Murine and Human Fibroblasts and in Mice", Journal of Clinical Investigation, 88: 1190-1196, 1991.
Burgess et al. "The Heparin-Binding (Fibroblast) Growth Factor of Proteins", Annual Review of Biochemistry, 58: 575-606, 1989.
Burrows et al. "Trophoblast Migration During Human Placental Implantation", Human Reproduction Update, 2(4): 307-321, 1996.
Cai et al. "Comparison of Sputum Processing Techniques in Cystic Fibrosis", Pediatric Pulmonoogy., 22(6): 402-407, 1996. Abstract.
Carson et al. "Mucin and Proteoglucan Functions in Embryo Implantation", BioEssays, 20(7): 577-583, 1998. Abstract, p. 580, col. 2 , § 2, p. 582, col. 1, Fig.1.
Chang et al. "Differential Ability of Heparan Sulfate Protecoglycans to Assemble the Fibroblast Growth Factor Receptor Complex In Situ", FASEB Journal, 14: 137-144, 2000.
Chiba et al. "Generation of Neutralizing Antibody to the Reserve Transcriptase of Human Immunodeficiency Virus Type 1 by Immunizing of Mice With an Infectious Vaccinia Virus Recombinant", Journal of Immunological Methods, 207(1): 53-60, Aug. 1997. Abstract.
Chleboun et al. "The Development and Enhancement of the Collateral Circulation in an Animal Model of Lower Limb Ischaemia",The Australian and New Zealand Journal of Surgery, 64(3): 202-207, 1994. Abstract.
Chow et al. "Development of an Epithelium-Specific Expression Cassette With Human DNA Regulatory Elements for Transgene Expression in Lung Airways", Proc. Natl. Acad. Sci. USA, 94: 14695-14700, 1997.
Chubet et al. "Vectors for Expression and Secretion of FLAG Epitope-Tagged Proteins in Mammalian Cells", BioTechniques, 20: 136-141, 1996. Abstract.
Clark "The Mammary Gland as A Bioreactor: Expression, Processing, and Production of Recombinant Proteins", Journal of Mammary Gland Biology and Neoplasia, 3(3): 337-350, 1998. Abstract.
Cohen "Oligonucleotide Therapeutics", Trends in Biotechnology 10: 87-91, 1992. Abstract.
Coligan et al. "Enzyme-Linked Immunosorbent Assays", Current Protocols in Immunology, 2.1.1-2.1.2, 1991.
Cordon-Cardo et al. "Expression of Basic Fibroblast Growth Factor in Normal Human Tissue", Laboratory Investigation, 63(6): 832-840, 1990. Abstract.
Cowley et al. "Mucociliary Clearance in Cystic Fibrosis Knockout Mice Infected With *Pseudomonas aeruginosa*", European Respiratory Journal, 10(10): 2312-2318, 1997.
Crystal "Gene Therapy Strategies for Pulmonary Disease", American Journal of Medicine, 92 (Suppl.64): 6A-44S-6A-52S, 1992.
Davies et al. "Regulation of the Alginate Biosynthesis Gene AlgC in *Pseudomonas aeruginosa* During Biofilm Development in Continuous Culture", Applied and Environmental Microbiology, 61(3): 860-867, 1995.
Davies et al. "The Involvement of Cell-to-Cell Signals in the Development of a Bacterial Biofilm", Science, 280: 295-298, 1998. Abstract.
Dempsey et al. "Heparanase Expression in Invasive Trophoblasts and Acute Vascular Damage", Glycobiology, 10(5): 467-475, 2000. Abstract, p. 470, col. 1, p. 471, col. 1-p. 472, col. 1, § 4-col. 2, § 2.
Dempsey et al. "Heparanase, A Potential Regulator of CellMatrix Interactions", TIBS, 25(8): 349-351, 2000. p. 350, col. 1, § 1, col. 3, § 1, Claims 1-24.
Docrks et al. "Protein Annotation: Detective Work for Function Prediction", Trends in Genetics, 14(6): 248-250, 1998.
Drigues et al. "Comparative Studies of Lipopolysaccharide and Exopolysaccharide From a Virulent Strain of *Pseudomonas solanacearum* and From Three Avirulent Mutants", Journal of Bacteriology, 162(2): 504-509, 1985. Abstract.
Ducy et al. "The Osteoblast: A Sophisticated Fibroblast Under Central Surveillance", Science, 289: 1501-1504, 2000.
Duffy et al. "Maximizing Flap Survival in a Prefabrication Model Using Exogenous and Endogenous bFGF: A New Approach", Microsurgery, 17(4): 176-179, 1996. Abstract.
Edwards et al. "Some Properties and Applications of Monoclonal Antibodies", Biochemical Journal, 200: 1-10, 1981.
Ehle et al. "Immunoaffinity Chromatography of Enzymes", Bioseparation, 1(2): 97-110, 1990.
Eisenberg et al. "Lipoprotein Lipase Enhances Binding of Lipoproteins to Heparan Sulfate on Cell Surface and Extracellular Matrix", Journal of Clinical Investigation, 90: 2013-2021, 1992.
Ejima et al. "Induction of Apoptosis in Placentas of Pregnant Mice Exposed to Lipopolysaccharides: Possible Involvement of Fas/Fas Ligand System", Biology of Reproduction, 62: 178-185, 2000. Abstract.
Elkin et al. "Heparanase as Mediator of Angiogenesis: Mode of Action", The FASEB Journal, 15: 1661-1663, 2001.
Elkin et al. "Heparanase as Mediator of Angiogenesis: Mode of Action", The FASEB Journal, Published Online, 10 p. 2001.
Ennis et al. "Rapid Cloning of HLA-A,B cDNA by Using the Polymerase Chain Reaction: Frequency and Nature of Errors Produced in Amplification", Proc. Natl. Acad. Sci. USA, 87: 2833-2837, 1990.
Ernst et al. "Enzymatic Degradation of Glycosaminoglycans", Critical Reviews in Biochemistry and Molecular Biology, 30(5): 387-444, 1995.
Esko et al. "Tumor Formation Dependent on Proeoglycans Biosynthesis", Science, 241(4869): 1092-1096, 1988. Abstract.
Evans et al. "Human Chromosome 11 187a8 Cosmid, Complete Sequence", Database EMBL, Accession No. U73640, XP002198427, 1996. Abstract.
Faber-Elman et al. "Involvement of Wound-Associated Factors in Rat Brain Astrocyte Migratory Response to Axonal Injury: In Vitro Simulation", Journal Clinical Investigation, 97(1): 162-171, 1996.
Fairbanks et al. "Processing of the Human Heparanase Precursor and Evidence that the Active Enzyme Is a Heterodimer", The Journal of Biological Chemistry, 274(42): 29587-29590, 1999.
Ferber et al. "Pancreatic and Duodenal Homeobox Gene 1 Induces Expression of Insulin Genes in Liver and Ameliorates Streptozotocin-Induced Hyperglycemia", Nature Medicine, 6(5): 568-572, 2000.
Folkman et al. "A Hcparin-Binding Angiogenic Protein—Basic Fibroblast Growth Factor—Is Stored Within Basement Membrane", American Journal of Pathology, 130(2): 393-400, 1988.
Folkman et al. "Angiogenic Factors", Science, 235(4787): 442-447, 1987.
Frederiksen et al. "Antibiotic Treatment of Initial Colonization With *Pseudomonas aeruginosa* Postpones Chronic Infection and Prevents Deterioraton of Pulmonary Function in Cystic Fibrosis", Pediatric Pulmonolaton, 23(5): 330-335, 1997. Abstract.
Frederiksen et al. "Changing Epidemiology of *Pseudomonas aeruginosa* Infection in Danish Cystic Fibrosis Patients (1974-1995)", Pediatric Pulmonology, 28(3): 159-166, 1999.
Freeman et al. "Human Platelet Heparanase: Purification, Characterization and Catalytic Activity", Biochemical Journal, 330: 1341-1350, 1998.
Freshney "Culture of Animal Cells", Wiley-VCH, 5th Ed.: 48-49, 2005. Abstract.
Fux et al. "Structure-Function Approach Identifies a COOH-Terminal Domain That Mediates Heparanase Signalling", Cancer Research, 69(5): 1758-1767, Mar. 1, 2009.
Gantt et al. "Cell Adhesion to a Motif Shared by the Malaria Circumsporozoite Protein and Thrombospondin Is Mediated by Its Glycosaminoglycan-Binding Region and Not by CSVTCG", The Journal of Biological Chemistry, 272(31): 19205-19213, 1997.
Garner "Epidermal Regulation of Dermal Fibroblast Activity", Plastic and Reconstructive Surgery, 102(1):135-139, 1998. Abstract.
Ghani et al. "Ceftazidime, Gentamicin, and Rifampicin, in Combination, Kill Biofilms of Mucoid *Pseudomonas aeruginosa*", Canadian Journal of Microbiology, 43(11): 999-1004, 1997. Abstract.

Gitay-Goren et al. "The Binding of Vascular Endothelial Growth Factor to Its Receptors Is Dependent on Cell Surface-Associated Heparin-Like Molecules", Journal of Biological Chemistry, 267(9): 6093-6098, 1992.

Giuffr? et al. "Monocyte Adhesion to Activated Aortic Endothelium: Role of L-Selectin and Heparan Sulfate Proteoglycans", The Journal of Cell Biology, 136(4): 945-956, 1997.

Godder ct al. "Heparanase Activity in Cultured Endothelial Cells", Journal of Cellular Physiology, 148: 274-280, 1991.

Goldberg et al. "An Improved Method for Determining Proteoglycans Synthesized by Chondrocytes in Culture", Live Tissue Research, 24: 265-275, 1990.

Goldshmidt et al. "Cell Surface Expression and Secretion of Heparanase Markedly Promote Tumor Angiogenesis and Metastasis", Proc. Natl. Acad. Sci. USA, 99(15): 10031-10036, 2002.

Gordon-Cardo et al. "Expression of Basic Fibroplast Growth Factor in Normal Human Tissues", Laboratory Investigation, 63: 832-840, 1990. Abstract.

Gospodarowicz et al. "Permissive Effect of the ExtraCellular Matrix on Cell Proliferation In Vitro", Proc. Natl. Acad. Sci. USA., 77(7): 4094-4098, 1980.

Gospodarowicz et al. "Stimulation of Corneal Endothelial Cell Proliferation In Vitro by Fibroblast and Epidermal Growth Factors", Experimental Eye Research, 25: 75-89, 1977. Abstract.

Gottschalk et al. "Somatic Gene Therapy. Present Situation and Future Perspective", Arzneimittelforschung, 48(11): 1111-1120, 1998. Abstract.

Green et al. "Antisense Oligonucleotides: An Evolving Technology for the Modulation of Gene Expression in Iluman Disease", Journal of American Cell Surgery, 191(1): 93-105, 2000.

Guo et al. "Protein Tolerance to Random Amino Acid Change", Proc. Natl. Acad. Sci. USA, 101(25): 9205-9210, 2004.

Guriec et al. "CD44 Isoforms With Exon V6 and Mestastasis of Primary N0M0 Breast Carcinomas", Breast Cancer Research and Treatment, 44(3):261-268, 1997. Abstract.

Haimov-Kochman et al. "Localization of Hepranase in Normal and Pathological Human Placenta", Molecular Human Reproduction, 8(6): 566-573, 2002.

Haisma et al. "A Monoclonal Antibody Against Human ?-Glucurinodase for Application in Antibody-Directed Enzyme Prodrug Therapy", Hybridoma, 14(4): 377-382, 1995.

Hammer et al. "Spontaneous Inflammatory Disease in Transgenic Rats Expressing HLA-B27 and Human β2m: An Animal Model of HLA-B27-Associated Human Disorders", Cell, 63: 1099-1112, 1990.

Harlow et al. "Antibodies—A Laboratory Manual", Cold Spring Harbor Press, p. 471-510, 1988.

Harvey et al. "Expression of Exogenous Protein in the Egg White of Transgenic Chickens", Nature Biotechnology, 19: 396-399, 2002.

Hatano et al. "Biologic Activities of Antobodies to the Neutral-Polysaccharide Component of the *Pseudomonas aeruginosa* Lipopolysaccharide Are Blocked by O Side Chains and Mucoid Exopolysaccharide (Alginate)", Infection and Immunity, 63(1): 21-26, 1995.

Hatch et al. "Alginate Lyase Promotes Diffusion of Aminoglycosides Through the Extracellular Polysaccharide of Mucoid *Pseudomonas aeruginosa*", Antimicrobial Agents and Chemotherapy, 42(4): 974-977, Apr. 1998.

Hayward et al. "Cellular Mechanisms of Heparinase III Protection in Rat Traumatic Shock", American Journal of Physiology, 275: II23-II30, 1998.

Hayward et al. "Heparinase III Exerts Endothelial and Cardioprotective Effects in Feline Myocardial Ischemia-Reperfusion Injury", Journal of Pharmacology and Experimental Therapeutics, 283(3): 1032-1038, 1997.

Hayward et al. "Heparinase III Exerts Endothelial and Cardioprotective Effects in Feline Myocardial Ischemia-Reperfusion Injury", The Journal of Pharmacology and Experimental Therapeutics, 283(3): 1032-1038, 1997.

Hida et al. "Antisense E1AF Transfection Restrains Oral Cancer Invasion by Reducing Matrix Metalloproteinase Activities", American Journal of Pathology, 150(6): 2125-2132, Jun. 1997.

Hillier et al. "The WashU-Merck EST Project" GenBank Entry N32056, 1996.

Hillier et al. "The WashU-Merck EST Project", Database EMBL Accession No. N45367, XP 002198420, 1996. Abstract.

Hillier et al. "The WashU-Merck EST Project", No. N30824, Database GenBank on STN, US National Library of Medicine (Bethesda MD), 1996.

Hillier et al. "The WashU-Merck EST Project", No. N30845, Database GenBank on STN, US National Library of Medicine (Bethesda MD), 1996.

Ho "Activation of Human ?-Glucuronidase by Murine Monoclonal Antibodies and Bovine Serum Albumin in an Uncompetitive Fashion", Biochemistry and Molecular Biology International, 36(6): 1277-1286, Aug. 1995.

Hudson "Recombinant Antibody Fragment", Current Opinion in Biotechnology, 4:395-402, 1998.

Hulett et al. "Cloning of Mammalian Heparanase, An Important Enzyme in Tumor Invasion and Metastasis", Nature Medicine, 5(7): 803-809, 1999.

Inui et al. "Local Application of Basic Fibroblast Growth Factor Minipellet Induces the Healing of Segmental Bony Defects in Rabbits", Calcified Tissue International, 63(6): 490-495, 1998. Abstract.

Ishai-Michaeli et al. "Heparanase Activity Expressed by Platelets, Neutrophilis, and Lymphoma Cells Releases Active Fibroblast Growth Factor From Extracellular Matrix", Cell Regulation, 1: 833-842, 1990.

Ishai-Michaeli et al. "Importance of Size and Sulfation of Heparin in Release of Basic Fibroblast Growth Factor From the Vascular Endothelium and ExtraCellular Matrix", Biochemistry, 31(7): 2080-2088, 1992. Abstract.

Jackson "The Use of Polyacrylamide-Gel Electrophoresis for the High-Resolution of Separation of Reducing Saccharides Labelled With the Fluorophore 8-Aminonaphtalene-1, 3, 6-Trisulphonic Acid", Biochemistry Journal, 270: 705-713, 1990.

Jayaraman et al. "Rational Selection and Quantitative Evaluation of Antisense Oligonucleotides", Biochimica et Biophysica Acta, 1520: 105-114, 2001.

Jin et al. "Immunochemical Localization of Heparanase in Mouse and Human Melanomas", International Journal of Cancer, 45: 1088-1095, 1990.

Jorba et al. "Variations in the *P. aeruginosa* Polysaccharide Synthesis Conditioned by Aminosugars", Revista Española de Fisiología, 36(2): 155-161, 1980. Abstract.

Kawaja et al. "Employment of Fibroblasts for Gene Transfer: Applications for Grafting Into the Central Nervous System", Genetic Engineering. NY, 13: 205-220, 1991. Abstract.

Kawase et al. "Effect of Partial Incision of the Zona Pellucida by Piezo-Micromanipulator for In Vitro Fertilization Using Frozen-Thawed Mouse Spermatozoa on the Developmental Rate of Embryos Transferred at the 2-Cell Stage", Biology of Reproduction, 66: 3810385, 2002. Abstract.

Kiberstis et al. "Bone Health in the Balance", Science, 289: 1497, 2000.

Kizaki et al. "Cloning and Localization of Heparanase in Bovine Placenta", Placenta, 24: 424-430, 2003.

Kizaki et al. "Expression of Heparanase mRNA in Bovine Placenta During Gestation", Reproduction, 121: 573-580, 2001.

Korb et al. "Stimulation of Gene Expression by Introns: Conversion of an Inhibitory Intron to a Stimulatory Intron by Alteration of the Splice Donor Sequence", Nucleic Acids Research, 21(25): 5901-5908, 1993.

Kosir et al. "Early Human Breast Carcinoma Cells Produce Extra Cellular Heparanase", Molecular Biology/Biochemistry, Proceedings of the American Association for Cancer Research, 37: 495, 1996.

Kosir et al. "Human Prostate Carcinoma Cells Produce Extracellular Heparanase", Journal of Surgical Research, 67: 98-105, 1997.

Kurachi et al. "Role of Intron I in Expression of the Human Factor IX Gene", Journal of Biological Chemistry, 270(10): 5276-5281, 1995.

Kussie et al. "Cloning and Functional Expression of a Human Heparanase Gene", Biochemical and Biophysical Research Communication, 261(1): 183-187, 1999. Suppl. IDS in 23665; Suppl. IDS in 22716; Suppl. IDS in 25783.

Lampard et al. "Secretion of Foreign Proteins Mediated by Chicken Lysozyme Gene Regulatory Sequences", Biochemistry and Cell Biology, 80(6): 777-788, 2002. Abstract.

Lessey et al. "Paracrine Signaling in the Endometrium: Integrins and the Establishement of Uterine Receptivity", Journal of Reproductive Immunology, 39(1-2): 105-116, 1998. Abstract.

Li et al. "Immunochemical Localization of Heparanase in Mouse and Human Melanomas", International Journal of Cancer, 45: 1088-1095, 1990.

Li et al. "In Vivo Fragmentation of Heparan Sulfate by Heparanase Overexpression Renders Mice Resistant to Amyloid Protein a Amyloidosis", Proc. Natl.Acad. Sci. USA, 102(18): 6473-6477, 2005.

Li et al. "β-Endorphin Omission Analogs: Dissociation of Immunoreactivity From Other Biological Activities", Proc. Natl. Acad. Sci. USA, 77: 3211-3214, 1980.

Lider et al. "A Disaccharide That Inhibits Tumor Necrosis Factor α Is Formed From the Extracellular Matrix by the Enzyme Heparanase", Proc. Natl. Acad. Sci. USA, 92: 5037-5041, 1995.

Lider et al "Inhibition of T Lymphocyte Heparanase by Heparin Prevents T Cell Migration and T Cell-Mediated Immunity", European Journal of Immunology, 20(3): 493-499, 1990. Abstract.

Liu et al. "Live Offspring by In Vitro Fertilization of Oocytes From Cryopreserved Primordial Mouse Follicles After Sequential In Vivo Transplantation and In Vitro Maturation", Biology of Reproduction, 64: 171-178, 2001. Abstract.

Loredo et al. "Regulation of Glycosaminoglycan Metabolism by Bone Morphogenetic Protein-2 in Equine Cartilage Explant Cultures", American Journal of Veterinary Research, 57(4): 554-559, 1996. Abstract.

Macone et al. "Mucoid *Escherichia coli* in Cystic Fibrosis", The New England Journal of Medicine, 304(24): 1445-1449, 1981. Abstract.

Maillard et al. "Pre-Treatment With Elastase Improves the Efficiency of Percutaneous Adenovirus-Mediated Gene Transfer to the Arterial Media", Gene Therapy, 5: 1023-1030, 1998. Abstract.

Makrides "Strategies for Achieving High-Level Expresion of Genes in *Escherichia coli*", Microbiological Reviews, 60(3): 512-538, 1996.

Marra et al. "The WashU-HHMI Mouse EST Project", Database EMBL, Accession No. A1122034, XP 002198426, 1998. Abstract.

Marra et al. "The WashU-HHMI Mouse Est Project", Database EMBL, Accession No. AA047943, XP002198424, 1996.

Massague "The TGF-BETA Family of Growth and Differentiation Factors", Cell, 49: 437-438, 1987.

Matzner et al. "Degradation of Heparan Sulfate in the Subendothelial Extracellular Matrix by a Readily Released Heparanase From Human Neutrophils", Journal of Clinical Investigation, 76(4): 1306-1313, 1985.

McKenzie et al. "Biochemical Characterization of the Active Heterodimer Form of Human Heparanase (Hpa1) Protein Expressed in Insect Cells", Biochemical Journal, 373: 423-435, 2003.

McKenzie et al. "Cloning and Expression Profiling of Hpa2, A Novel Mammalian Heparanase Family Member", Biochemical and Biophysical Research Communications, 276(3): 1170-1177, 2000.

Menezo et al. "Mouse and Bovine Models for Human IVF", Reproductive BioMedicine Online 2002, 4(2): 170-175, 2002. Abstract.

Mengistu et al. "Continuous Culture Studies on the Synthesis of Capsular Polysaccharide by Klebsiella Pneumoniae K1", Journal of Applied Bacteriology, 76(5): 424-430, 1994. Abstract.

Mes et al. "Relative Sensitivity of Various Reagents for the Detection and Differentiation of Sugars and Sugar Derivatives in Glycoproteins", Journal of Chromatography, 38(1): 120-125, 1968. Abstract.

Mes et al. "The Use of Triphenyltetrazolium Chloride for the Quantitative Analysis of Sugars and Sugar Derivatives Reported in Glycoproteins", Journal of Chromatography, 43: 480-486, 1969. Abstract.

Mettenleiter et al. "Interaction of Glycoprotein GIII With a Cellular Heparinlike Substance Mediates Adsorption of Pseudorabies Virus", Journal of Virology, XP002503372, 64(1): 278-286, Jan. 1990. p. 281, r-h col., § 1, 2.

Miao et al. "Cloning, Expression and Purification of Mouse Heparanase", Protein Expression and Purification, 26: 425-431, 2002.

Miller et al. "Xenograft Model of Progressive Human Proliferative Breast Disease", Journal of the National Cancer Institute, 85(21): 1725-1732, Nov. 3, 1993. Abstract.

Mirault et al. "Transgenic Glutathione Peroxidase Mouse Models for Neuroprotection Studies", Annals of the New York Academy of Sciences, 738: 104-115, 1994. Abstract.

Miyake et al. "Highly Specific and Sensitive Detection of Malignancy in Urine Samples From Patients With Urothelial Cancer by CD44v8-10/CD44v10 Competitive RT-PCR", International Journal of Cancer, 79(6): 560-564, 1998. Abstract.

Morel et al. "Human Neutrophil Gelitanase Is a Collagenase Type IV", Biochemical & Biophysical Research Communications, 191: 269-274, 1993.

Morrison et al. "Sequences in Antibody Molecules Important for Receptor-Mediated Transport Into the Chicken Egg Yolk", Molecular Immunology, 38(8): 619-625, 2002. Abstract.

Moser et al. "Chronic *Pseudomonas aeruginosa* Lung Infection Is More Severe in Th2 Responding BALB/c Mice Compared to Th1 Responding C3H/HeN Mice", APMIS, 105(11): 838-842, 1997. Abstract.

Muir et al. "Histomorphometric Analysis of the Effects of Standard Heparin on Trabecular Bone In Vivo", Blood, 88(4): 1314-1320, 1996. Abstract.

Mullins et al. "Expression of the DBA/2J Ren-2 Gene in the Adrenal Gland of Transgenic Mice", The EMBO Journal, 8(13): 4065-4072, 1989.

Mullins et al. "Fulminant Hypertension in Transgenic Rats Harbouring the Mouse Ren-2 Gene", Nature, 344: 541-544, 1990.

Murphy et al. "The Latent Collagenase and Gelatin of Human Polymorphonuclear Neutrophil Leucicytes", Biochemistry Journal, 192: 517-525, 1980.

Myers et al. "Transplantation of Keratinocytes in the Treatment of Wounds", The American Journal of Surgery, 170(1): 75-83, 1995. Abstract.

Nadav et al. "Activation, Processing and Trafficking of Extracellular Heparanase by Primary Human Fibroblasts", Journal of Cell Science, 115(10): 2179-2187, 2002.

Nadir et al. "Co—Interaction and Increased Release of Tissue Factor Pathway Inhibitor by Heparanase", Blood, 106(11/Part 2): 90B, 2005. Abstract# 4038.

Nakajima et al. "Heparan Sulfate Degradation: Relation to Tumor Invasion and Metatastic Properties of Mouse B16 Melanoma Sublines", Science, 220: 611-613, 1983.

Naparstek et al. "Activated T Lymphocytes Produce a Matrix-Degrading Heparan Sulphate Endoglycosidase", Nature, 310(5974): 241-244, 1984. Abstract.

Narindrasorasak et al. "High Affinity Interactions Between the Altzheimer's β-Amyloid Precursor Proteins and the Basement Membrane Form of Heparan Sulfate Proteoglycan", The Journal of Biological Chemistry, 266(20): 12878-12883, Jul. 15, 1991.

Nasser et al. "Heparanase Neutralizes the Anticoagulation Properties of Heparin and Low-Molecular-Weight Heparin", Journal of Thrombosis and Haemostasis, 4: 560-565, 2006.

Newbold et al. "Exposure to Diethylstilbestrol During Pregnancy Permanently Alters the Ovary and Oviduct", Biology of Reproduction, 28: 735-744, 1983. Abstract.

Nilsson et al. "The Role of Staphylococcal Polysaccharide Microcapsule Expression in Septricemia and Septic Arthritis", Infection & Immunity, 65(10): 4216-4221, Oct. 1997.

Niwa et al. "Efficient Selection for High-Expression Transfectants With a Novel Eukaryotic Vector", Gene, 108(2): 193-199, 1991. Abstract.

Ofek et al. "Bacterial Adhesion to Cells and Tissues", Chapman & Hall, NY, p. 114-118, 148-153, 418-423, 420-423, 1994.

Okamoto et al. "Highly Specific and Sensitive Detection of Malignancy in Urine Samples From Patients With Urothelial Cancer by CD44V8-10/CD44V10 Competitive RT-PCR", International Journal of Cancer, 79(6): 560-564, Dec. 18, 1998. Abstract.

Oldberg et al. "Characterization of a Platelet Endoglycosidase Degrading Heparin-Like Polysaccharides", Biochemistry, 19: 5755-5762, 1980.

Ornitz et al. "Heparin Is Required for Cell-Free Binding of Basic Fibroblast Growth Factor to a Soluble Receptor and for Mitogenesis in Whole Cells", Molecular and Cellular Biology, 12: 240-247, Jan. 1992.

Parish et al. "Evidence That Sulphated Polysaccharides Inhibit Tumor Metastasis by Blocking Tumor-Cell-Derived Heparanases", International Journal of Cancer, 40: 511-517, 1987.

Parish et al. "Treatment of Central Nervous System Inflammation With Inhibitors of Basement Membrane Degradation", Immunology & Cell Biology, 76: 104-113, 1998. Abstract. p. 104-108.

Pasquier et al. "Implication of Neutral Polysaccharides Associated to Alginate in Inhibition of Murine Macrophage Response to *Pseudomonas aeruginosa*", FEMS Microbiology Letters, 147(2): 195-202, 1997. Abstract.

Pfaff et al. "Cryobiology of Rat Embryos I: Determination of Zygote Membrane Permeability Coefficients for Water and Cryoprotectants, Their Activation Energies, and the Development of Improved Cryopreservation Methods", Biology of Reproduction, 63: 1294-1302, 2000. Abstract.

Pier "Rationale for Development of Immunotherapies That Target Mucoid *Pseudomonas aeruginosa* Infection in Cystic Fibrosis Patients", Behring Inst. Mitt., 98: 350-360, 1997. Abstract.

Pier et al. "Cystic Fibrosis Transmembrane Conductance Regulator Is an Epithelial Cell Receptor for Clearance of *Pseudomonas aeruginosa* From the Lung", Proc. Natl. Acad. Sci. USA, 94(22): 12088-12093, 1997.

Pilbeam et al. "Comparison of the Effects of Various Lengths of Synthetic Human Parathyroid Hormone-Related Peptide (hPTHrP) of Malignancy on Bone Resorption and Formation in Organ Culture", Bone, 14: 717-720,1993.

Pina et al. "The Role of Fluoroquinolones in the Promotion of Alginate Synthesis and Antibiotic Resistance in *Pseudomonas aeruginosa*", Current Microbiology, 35(2): 103-108, 1997. Abstract.

Prockop "Marrow Stromal Cells as Stem Cells for Nonhematopoietic Tissues", Science, 276: 71-74, 1997.

Rader et al. "A Phage Display Approach for Rapid Antibody Humanization: Designed Combinatorial V Gene Libraries", Proc. Natl. Acad. Sci. USA, 95: 8910-8915, 1998.

Raghunath et al. "Cultured Epithelial Autografts: Diving From Surgery Into Matrix Biology", Pediatric Surgery International, 12(7): 478-483, 1997. Abstract.

Rahmoune et al. "Chrondroitin Sulfate in Sputum From Patients With Cystic Fibrosis and Chronic Bronchitis", American Journal of Respiratory Cell & Molecular Biology, 5(4): 315-320, 1991. Abstract.

Rajur et al. "Covalent Protein-Oligonucleotide Conjugates for Efficient Delivery of Antisense Molecules", Bioconjugate Chemistry, 8: 935-940, 1997.

Ramos et al. "Relationship Between Glycolysis and Exopolysaccharide Biosynthesis in Lactococcus Lactis", Applied and Environmental Microbiology, 67(1): 33-41, Jan. 2001.

Ramsey et al. "Intermittent Administraton of Inhaled Tobramycin in Patients With Cystic Fibrosis. Cystic Fibrosis Inhaled Tobramycin Study Group", New England Journal of Medicine, 340(1): 23-30, 1999. Abstract.

Richardson et al. "Regulation of Basic Fibroblast Growth Factor Binding and Avtivity by Cell Density and Heparan Sufate", Journal Biological Chemistry, 274(19): 13534-13540, 1990.

Rubin "Emerging Therapies for Cystic Fibrosis Lung Disease", Chest, 115: 1120-1126, 1999.

Ruppert et al. "Human Bone Morphogenic Protein 2 Contains a Heparin-Binding Site Which Modifies Its Biological Activity", European Journal of Biochemistry., 237(1): 295-302, 1996. Abstract.

Sasisekharan et al. "Cloning and Expression of Heparinase I Gene From Flavobacterium Heparinum", Proc. Natl. Acad. Sci. USA, 90: 3660-3664, 1993.

Schoepe et al. "Neutralization of Hemolytic and Mouse Lethal Activities of *C. perfringens* Alpha-Toxin Need Simultaneous Blockage of Two Epitopes by Monoclonal Antibodies", Microbial Pathogenesis, 23(1): 1-10, 1997. Abstract.

Schwartz et al. "CpG Motifs in Bacterial DNA Cause Inflammation in the Lower Respiratory Tract", Journal of Clinical Investigation, 100(1): 68-73, 1997.

Scott et al. "Visualization of an Extracellular Mucoid Layer of Treponema Denticola ATCC 35405 and Surface Sugar Lectin Analysis of Some Treponema Species", Oral Microbiology & Immunology, 12(2): 121-125, 1997. Abstract.

Selvan et al. "Heparan Sulfate in Immune Responses", Annals of the New York Academy of Sciences, 797: 127-139, 1996.

Service "Tissue Engineers Build New Bone", Science, 289: 1498-1500, 2000.

Shimada et al. "Involvement of Cell Surface Heparin Sulfate in the Binding of Lipoprotein Lipase to Cultured Bovine Endothelial Cells", Journal of Clinical Investigation, 68(4): 995-1002, Oct. 1981.

Skolnick et al. "From Genes to Protein Structure and Function: Novel Applications of Computational Approaches in the Genomic Era", Trends in Biotechnology, 18: 34-39, 2000.

Soule et al. "Isolation and Characterization of a Spontaneously Immortalized Human Breast Epithelial Cell Line, MCF-10[1]", Cancer Research, 50: 6075-6086, 1990. Abstract.

Speert et al. "Modulation of Macrophage Function for Defense of the Lung Against *Pseudomonas aeruginosa*", Behring Institut Mitteilungsblatt, 98: 274-282, Feb. 1997. Abstract.

Spencer "Invasive Streptococci", European Journal of Clinical Microbiology & Infectious Diseases, 14(Suppl.1): S26-S32, 1995. Abstract.

Spiegel et al. "Heparanase Facilitates Development and SDF-1 Induced Migration of Hematopoietic Stem and Progenitor Cells", Blood, 102(11): 825a-826a, 2003. Abstract# 3056.

Spivak-Kroizman et al. "Heparin-Induced Oligomerization of FGF Molecules Is Responsible for FGF Receptor Dimerization, Activation, and Cell Proliferation", Cell, 79: 1015-1024, 1994.

Suggs et al. "Use of Synthetic Oligonucleotides as Hybridization Probes: Isolation of Cloned cDNA Sequences for Human ?2-Microglobulin", Proc. Natl. Acad. Sci. USA, 78(11): 6613-6617, 1981. p. 6613.

Tabata et al. "Bone Regeneration by Basic Fibroblast Growth Factor Complexed With Biodegradable Hydrogels", Biomaterials, 19(7-9): 807-815, Apr.-May 1998. Abstract.

Takayama et al. "Neutrophil-Dependent Goblet Cell Degranulation: Role of Membrane-Bound Elastase and Adhesion Molecules", AJP, American Journal of Physiology—Lung Cellular and Molecular Physiology, 275(2/Part 1): L294-L302, 1998.

Tang et al. "Contribution of Specific *Pseudomonas aeruginosa* Virulence Factors to Pathogenesis of Pneumonia in a Neonatal Mouse Model of Infection", Infection and Immunity, 64(1): 37-43, 1996.

Tatnell et al. "Characterisation of Alginates From Mucoid Strains of *Pseudomonas aeruginosa*", Biochemical Society Transactions, 24: 404S, 1996.

Tatnell et al. "Chemical Analysis of Alginates From Mucoid Strains of *Pseudomonas aeruginosa*", Biochemical Society Transactions, 22: 310S, 1994.

Tatnell et al. "Colonisation of Cystic Fibrosis Patients by Non-Mucoid *Pseudomonas aeruginosa*—Characterisation of the Alginate From Mucoid Variants", Biochemical Society Transactions, 24: 406S, 1996.

Taurog et al. "HLA-B27 in Inbred and Non-Inbred Transgenic Mice", The Journal of Immunology, 141(11): 4020-4023, 1988.

Taylor et al. "A Colorimetric Method for the Quantitation of Uronic Acids and a Specific Assay for Galacturonic Acid", Analytical Biochemistry, 201: 190-196, 1992. Abstract.

Thompson et al. "Identification of Chondroitin Sulfate E in Human Lung Mast Cells", Journal of Immunology, 140(8): 2708-2713, 1988. Abstract.

Thuong et al. "Sequence-Specific Recognition and Modification of Double-Helical DNA by Oligonucleotides", Angewandte Chemie International Edition in English, 32: 666-690, 1993.

Toyoshima et al. "Human Heparanase: Purification, Characterization, Cloning, and Expression", Journal of Biological Chemistry, 274(34): 24153-24160, 1999.

Uno et al. "Antisense-Mediated Suppression of Human Heparanase Gene Expression Inhibits Pleural Dissemination of Human Cancer Cells", Cancer Research, 61(21): 7855-7860, 2001.

Van Heeckeren et al. "Excessive Inflammatory Response of Cystic Fibrosis Mice to Bronchopulmonary Infection With *Pseudomonas aeruginosa*", Journal of Clinical Investigation, 100(11): 2810-2815, 1997.

Vernet et al. "Virulence Factors (Aerobactin and Mucoid Phenotype) in Klebsiella Pneumoniae and *Escherichia coli* Blood Culture Isolates", FEMS Microbiological Letters, 130(1): 51-57, 1995. Abstract.

Vlodavsky et al. "Extracellular Matrix-Resident Growth Factors and Enzymes: Possible Involvement in Tumor Metastasis and Angiogenesis", Cancer and Metatastis Reviews, 9(3): 203-226, Nov. 1990.

Vlodavsky et al "Inhibition of Tumor Metastasis by Heparanase Inhibiting Species of Heparin", Invasion & Metastasis, 14(1-6): 290-302, 1994/95. Suppl. S18 in 21782; Suppl. IDS in 27970; IDS in 25718; Suppl. IDS in 23884; Suppl. IDS in 22716; Suppl. IDS in 25783.

Vlodavsky et al. "Involvement of Heparanase in Tumor Metastasis and Angiogenesis", IsraeliJournal of Medical Sciences, 24(9-10): 464-470, 1988.

Vlodavsky et al. "Involvement of the ExtraCellular Matrix, Heparin Sulfate Proteoglycans, and Heparin Sulfate Degrading Enzymes in Angiogenesis and Metastis", Tumor Angeogenesis, p. 125-140, 1997.

Vlodavsky et al. "Lymphoma Cell-Mediated Degradation of Sulfated Proteoglycans in the Subendothelial ExtraCellular Matrix: Relationship to Tumor Cell Metastasis", Cancer Research, 43: 2704-2711, 1983.

Vlodavsky et al. "Mammalian Heparanase: Gene Cloning, Expression and Function in Tumor Progression and Metastasis", Nature Medicine, 5(7): 793-802, 1999.

Vlodavsky et al. "Morphological Appearance, Growth Behaviour and Migratory Activity of Human Tumor Cells Maintained on Extracellular Matrix Versus Plastic", Cell, 19: 607-616, 1980. Abstract.

Vogel et al. "Production of Proteoglycans by Human Lung Fibroblasts (IMR-90) Maintained in a Low Concentration of Serum", Biochemical Journal, 207(3): 369-379. Abstract.

Vukicevic et al. "Induction of Nephrrogenic Mesenchyme by Osteogenic Protein 1 (Bone Morphogenetic Protein 7)", Proc. Natl. Acad. Sci. USA, 93: 9021-9026, 1996.

Walch et al. "Correlation of Overexpression of the Low-Affinity p75 Neutrotrophin Receptor With Augmented Invasion and Heparanase Production in Human Malignant Melanoma Cells", International Journal of Cancer, 82: 112-120, 1999.

Wang et al. "Isolation and Characterization of *Pseudomonas aeruginosa* Genes Inducible by Respiratory Mucus Derived From Cystic Fibrosis Patients", Molecular Microbiology, 22(5): 1005-1012, 1996. Abstract.

Watson et al. "A Growth Factor Phenotype Map for Ovine Preimplantation Development", Biology of Reproduction, 50(4): 725-733, 1994.

Welch et al. "Complex Saccharide Metabolism in Cystic Fibrosis Fibroblasts", Pediatric Research, 9(9): 698-702, 1975. Abstract.

Whitelock et al. "The Degradation of Human Endothelial Cell-Derived Perlecan and Release of Bound Basic Fibroblast Growth Factor by Stromelysin, Collagenase, Plasmin, and Heparanases", Journal of Biological Chemistry, 271(17): 10079-10086, 1996.

Wight et al. "Cell Biology of Arterial Proteoglycans", Arteriosclerosis, 9(1): 1-20, 1989. Abstract.

Wight et al. "The Role of Proteoglycans in Cell Adhesion, Migration and Proliferation", Current Opinion in Cell Biology, 4: 793-801, 1992. Abstract.

Yazaki et al. "The Structure and Expression of the FGF Receptor-1 mRNA Isoforms in Rat Tissues", Biochimica et Biophysica Acta, 1172: 37-42, 1993.

Yoshida "Effects of Basic Fibroblast Growth Factor on the Development of Mouse Preimplantation Embryos", Nippon Sanka Fujinka Gakkai Zasshi, 48(3): 170-176, 1996. Abstract.

Yu et al. "Microbial Pathogens in Cystic Fibrosis: Pulmonary Clearance of Mucoid *Pseudomonas aeruginosa* and Inflammation in a Mouse Model of Repeated Respiratory Challenge", Infection and Immunity, 66(1): 280-288, 1998.

Zeharia et al. "Heparanase Acclerates Wound Angiogenesis and Wound Healing in Mouse and Rat Models", The FASEB Journal, 19: 211-221, 2005.

Zeharia et al. "Heparanase Regulates Murine Hair Growth", American Journal of Pathology, 166(4): 999-1008, 2005.

Zeharia et al. "Molecular Properties and Involvement of Heparanase in Cancer Progression and Mammary Gland Morphogenesis", Journal of Mammary Gland Biology and Neoplasia, 6(3): 311-322, 2001.

Zeharia et al. "Transgenic Expression of Mammalian Heparanase Uncovers Physiological Functions of Heparan Sulfate in Tissue Morphogenesis, Vascularization, and Feeding Behavior", The FASEB Journal, 18: 252-263, 2004.

Zhong-Sheng et al. "Role of Heparan Sulfate Proteoglycans in the Binding and Uptake of Apolipoprotein E-Enriched Remnant Lipoproteins by Cultured Cells", Journal of Biological Chemistry, 268(14): 10160-10167, 1993.

Zhou et al. "A 182 Bp Fragment of the Mouse Pro?1(11) Collagen Gene Is Sufficient to Direct Chondrocyte Expression in Transgenic Mice", Journal of Cell Science, 108: 3677-3684, 1995.

Zhou et al. "HFE Gene Knockout Produces Mouse Model of Hereditary Hemochromatosis", PNAS, 95(5): 2492-2497, 1998.

Zhu et al. "Development of Heritable Melanoma in Transgenic Mice", The Journal of Investigative Dermatology, 110: 247-252, 1998.

Coligan et al. "Enzyme-Linked Immunosorbent Assays", Current Protocols in Immunology, 2.1.1-2.1.2, 1991.

Response Dated Jun. 9, 2011 to Communication Pursuant to Article 94(3) EPC of Nov. 29, 2010 From the European Patent Office Re. : Application No. 04001481.3.

* cited by examiner

FIG. 9A
FIG. 9B
FIG. 9C
FIG. 9D
FIG. 9E
FIG. 9F
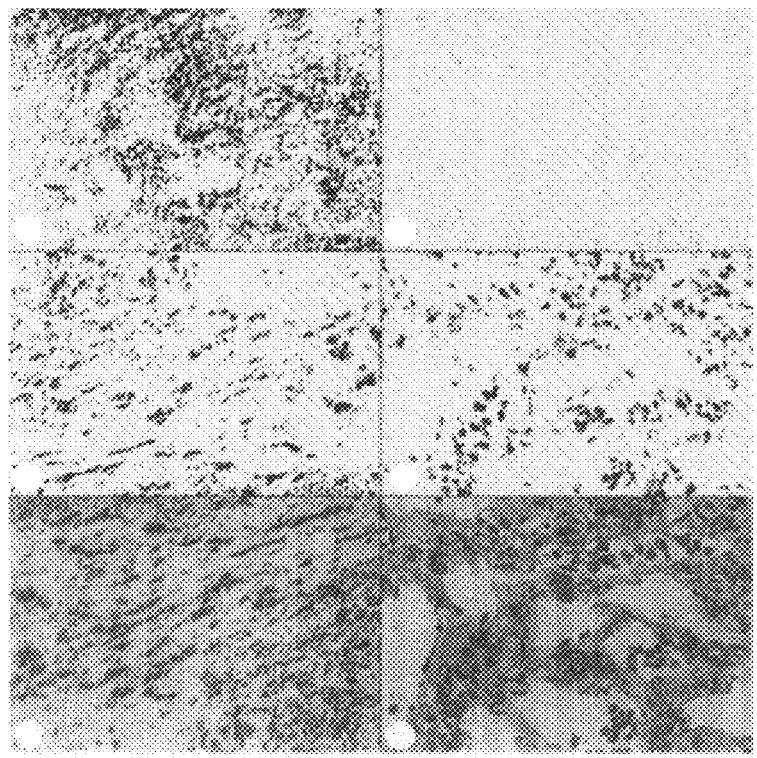
FIG. 10A
FIG. 10B
FIG. 10C
FIG. 10D
FIG. 10E
FIG. 10F
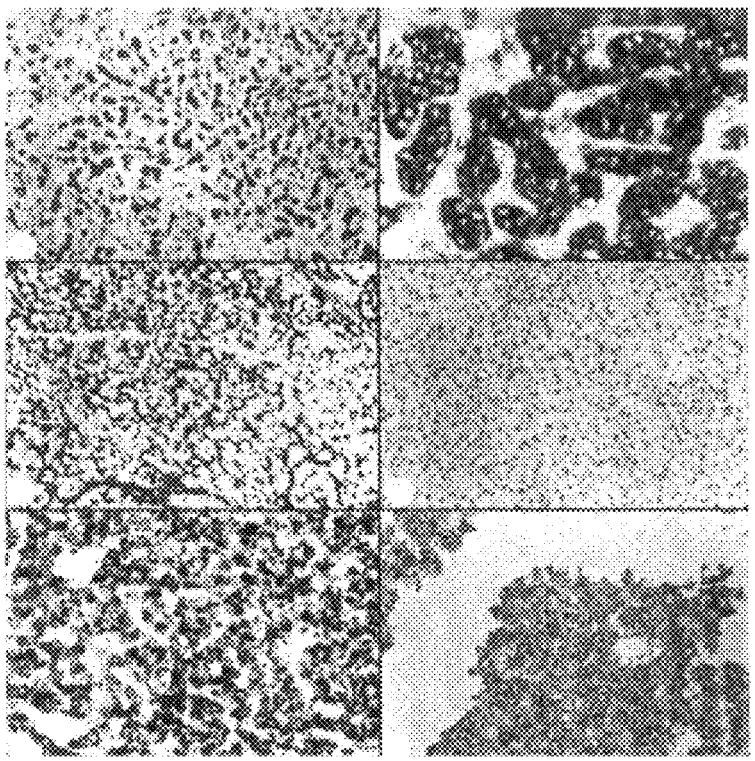

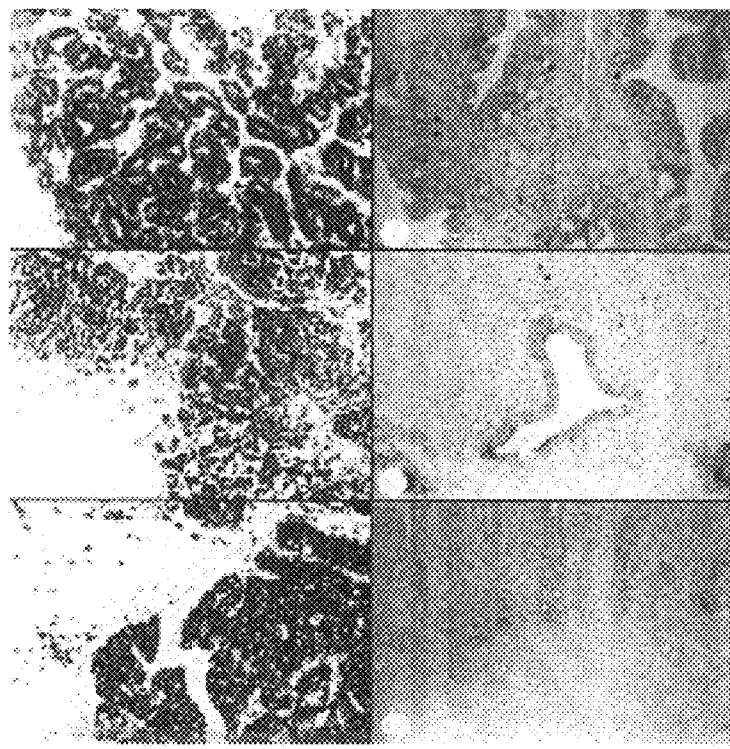
FIG. 11A　　　　　　　　　　　FIG. 11B
FIG. 11C　　　　　　　　　　　FIG. 11D
FIG. 11E　　　　　　　　　　　FIG. 11F
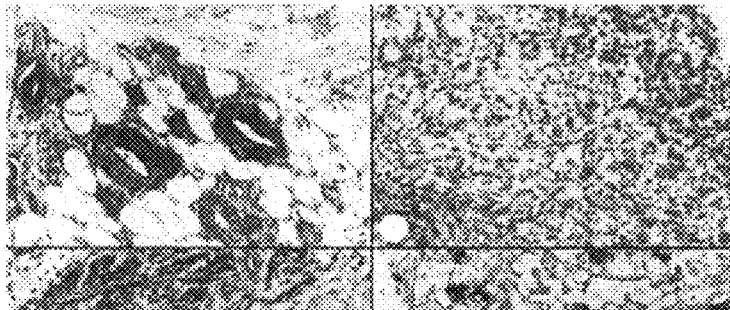
FIG. 12A　　　　　　　　　　　FIG. 12B
FIG. 12C　　　　　　　　　　　FIG. 12D
FIG. 12E　　　　　　　　　　　FIG. 12F

HEPARANASE SPECIFIC MOLECULAR PROBES AND THEIR USE IN RESEARCH AND MEDICAL APPLICATIONS

RELATED APPLICATIONS

This is a continuation of U.S. patent application Ser. No. 10/676,079 filed Oct. 2, 2003 which is a divisional of U.S. patent application Ser. No. 09/704,772, filed Nov. 3, 2000, now U.S. Pat. No. 6,699,672, issued Mar. 2, 2004 which is a divisional of U.S. patent application Ser. No. 09/322,977, filed Jun. 1, 1999, now U.S. Pat. No. 6,531,129, issued Mar. 11, 2003, which is a divisional of U.S. patent application Ser. No. 09/071,739, filed May 1, 1998, now U.S. Pat. No. 6,177,545, issued Jan. 23, 2001, which is a continuation-in-part of U.S. patent application Ser. No. 08/922,170, filed Sep. 2, 1997, now U.S. Pat. No. 5,968,822, issued Oct. 19, 1999. The contents of the above applications are incorporated herein by reference.

FIELD AND BACKGROUND OF THE INVENTION

The present invention relates to heparanase specific molecular probes their use in research and medical applications. More particularly, the present invention relates to the use of heparanase specific molecular probes, such as anti-heparanase antibodies (both poly- and monoclonal) and heparanase gene (hpa) derived nucleic acids, including, but not limited to, PCR primers, antisense oligonucleotide probes, antisense RNA probes, DNA probes and the like for detection and monitoring of malignancies, metastasis and other non-malignant conditions, efficiency of therapeutic treatments, targeted drug delivery and therapy.

Heparan sulfate proteoglycans (HSPGs): HSPGs are ubiquitous macromolecules associated with the cell surface and extracellular matrix (ECM) of a wide range of cells of vertebrate and invertebrate tissues (1-5). The basic HSPG structure consists of a protein core to which several linear heparan sulfate chains are covalently attached. The polysaccharide chains are typically composed of repeating hexuronic and D-glucosamine disaccharide units that are substituted to a varying extent with N- and O-linked sulfate moieties and N-linked acetyl groups (1-5). Studies on the involvement of ECM molecules in cell attachment, growth and differentiation revealed a central role of HSPGs in embryonic morphogenesis, angiogenesis, metastasis, neurite outgrowth and tissue repair (1-5). The heparan sulfate (HS) chains, unique in their ability to bind a multitude of proteins, ensure that a wide variety of effector molecules cling to the cell surface (4-6). HSPGs are also prominent components of blood vessels (3). In large vessels they are concentrated mostly in the intima and inner media, whereas in capillaries they are found mainly in the subendothelial basement membrane where they support proliferating and migrating endothelial cells and stabilize the structure of the capillary wall. The ability of HSPGs to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of HS may therefore result in disassembly of the subendothelial ECM and hence may play a decisive role in extravasation of blood-borne cells (7-9). HS catabolism is observed in inflammation, wound repair, diabetes, and cancer metastasis, suggesting that enzymes which degrade HS play important roles in pathologic processes.

Involvement of heparanase in tumor cell invasion and metastasis: Circulating tumor cells arrested in the capillary beds of different organs must invade the endothelial cell lining and degrade its underlying basement membrane (BM) in order to escape into the extravascular tissue(s) where they establish metastasis (10). Several cellular enzymes (e.g., collagenase IV, plasminogen activator, cathepsin B, elastase) are thought to be involved in degradation of the BM (10). Among these enzymes is an endo-β-D-glucuronidase (heparanase) that cleaves HS at specific intrachain sites (7, 9, 11-12). Expression of a HS degrading heparanase was found to correlate with the metastatic potential of mouse lymphoma (11), fibrosarcoma and melanoma (9) cells. Treatment of experimental animals with heparanase inhibitors (i.e. non-anticoagulant species of low MW heparin) markedly reduced (>90%) the incidence of lung metastases induced by B16 melanoma, Lewis lung carcinoma and mammary adenocarcinoma cells (8, 9, 13).

Heparanase activity could not be detected in normal stromal fibroblasts, mesothelial, endothelial and smooth muscle cells derived from non cancerous biopsies and effusions (12). These observations indicate that heparanase expression may serve as a marker for tumor cells and in particular for those which are highly invasive or potentially invasive. If the same conclusion can be reached by immunostaining of tissue specimens, anti-heparanase antibodies may be applied for early detection and diagnosis of metastatic cell populations and micro-metastases.

Our studies on the control of tumor progression by its local environment, focus on the interaction of cells with the extracellular matrix (ECM) produced by cultured corneal and vascular endothelial cells (EC) (14, 15). This ECM closely resembles the subendothelium in vivo in its morphological appearance and molecular composition. It contains collagens (mostly type III and IV, with smaller amounts of types I and V), proteoglycans (mostly heparan sulfate- and dermatan sulfate-proteoglycans, with smaller amounts of chondroitin sulfate proteoglycans), laminin, fibronectin, entactin and elastin (13, 14). The ability of cells to degrade HS in the ECM was studied by allowing cells to interact with a metabolically sulfate labeled ECM, followed by gel filtration (SEPHAROSE 6B) analysis of degradation products released into the culture medium (11). While intact HSPG are eluted next to the void volume of the column (Kav<0.2, Mr~0.5× $10^6$), labeled degradation fragments of HS side chains are eluted more toward the Vt of the column (0.5<kav<0.8, Mr=5-7×$10^3$) (11).

Possible involvement of heparanase in tumor angiogenesis: Fibroblast growth factors are a family of structurally related polypeptides characterized by high affinity to heparin (16). They are highly mitogenic for vascular endothelial cells (EC) and are among the most potent inducers of neovascularization (16, 17). Basic fibroblast growth factor (bFGF) has been extracted from subendothelial ECM produced in vitro and from BM of the cornea, suggesting that ECM may serve as a reservoir for bFGF (18). Studies on the interaction of bFGF with ECM revealed that bFGF binds to HSPG in the ECM and can be released in an active form by HS degrading enzymes (19, 20). Heparanase activity expressed by platelets, mast cells, neutrophils, and lymphoma cells releases active bFGF from ECM and BM (20), suggesting that heparanase may not only function in cell migration and invasion, but may also elicit an indirect neovascular response (18). These results suggest that the ECM HSPGs provide a natural storage depot for bFGF and possibly other heparin-binding growth promoting factors. Displacement of bFGF from its storage within ECM may therefore provide a novel mechanism for induction of neovascularization in normal and pathological situations (6, 18).

Expression of heparanase by cells of the immune system: Heparanase activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulfate (HS) by heparanase activity (7). The enzyme is released from intracellular compartments (e.g., lysosomes, specific granules) in response to various activation signals (e.g., thrombin, calcium ionophore, immune complexes, antigens, mitogens), suggesting its regulated involvement and presence in inflammatory sites and autoimmune lesions. Heparan sulfate degrading enzymes released by platelets and macrophages are likely to be present in atherosclerotic lesions (21). Hence, cDNA probes and anti-heparanase antibodies may be applied for detection and early diagnosis of these lesions.

Cloning and expression of the heparanase gene: The cloning and expression of the human heparanase gene are described in U.S. Pat. No. 5,968,822, which is incorporated by reference as if fully set forth herein. A purified fraction of heparanase isolated from human hepatoma cells was subjected to tryptic digestion. Peptides were separated by high pressure liquid chromatography and micro sequenced. The sequence of one of the peptides was used to screen data bases for homology to the corresponding back translated DNA sequence. This procedure led to the identification of a clone containing an insert of 1020 base pairs (bp) which included an open reading frame of 963 bp followed by 27 bp of 3' untranslated region and a Poly A tail. The new gene was designated hpa. Cloning of the missing 5' end of hpa cDNA was performed by PCR amplification of DNA from placenta cDNA composite. The plasmid containing the entire heparanase cDNA was designated phpa. The joined cDNA fragment contained an open reading frame which encodes a polypeptide of 543 amino acids with a calculated molecular weight (MW) of 61,192 daltons. The ability of the hpa gene product to catalyze degradation of heparan sulfate (HS) in vitro was examined by expressing the entire open reading frame of hpa in High five and Sf21 insect cells, using the Baculovirus expression system. Extracts of infected cells were assayed for heparanase activity. For this purpose, cell lysates were incubated with sulfate labeled, ECM-derived HSPG (peak I), followed by gel filtration analysis (SEPHAROSE 6B) of the reaction mixture. While the substrate alone consisted of high molecular weight (MW) material, incubation of the HSPG substrate with lysates of cells infected with hpa containing virus resulted in a complete conversion of the high MW substrate into low MW labeled heparan sulfate degradation fragments.

In subsequent experiments, the labeled HSPG substrate was incubated with the culture medium of infected High Five and Sf21 cells. Heparanase activity, reflected by the conversion of the high MW HSPG substrate into low MW HS degradation fragments, was found in the culture medium of cells infected with the pFhpa virus, but not the control pF1 virus. Altogether, these results indicate that the heparanase enzyme is expressed in an active form by cells infected with Baculovirus containing the newly identified human hpa gene. In other experiments, we have demonstrated that the heparanase enzyme expressed by cells infected with the pFhpa virus is capable of degrading HS complexed to other macromolecular constituents (e.g., fibronectin, laminin, collagen) present in a naturally produced intact ECM, in a manner similar to that reported for highly metastatic tumor cells or activated cells of the immune system.

Purification of the recombinant heparanase enzyme: The purification of the human heparanase gene are described in U.S. Pat. No. 5,968,822, which is incorporated by reference as if fully set forth herein. Sf21 insect cells were infected with pFhpa virus and the culture medium was applied onto a heparin-SEPHAROSE column. Fractions were eluted with a salt gradient (0.35-2 M NaCl) and tested for heparanase activity and protein profile (SDS/PAGE followed by silver staining). Heparanase activity correlated with the appearance of a protein band of about 63 kDa in fractions 19-24, consistent with the expected MW of the hpa gene product. Active fractions eluted from heparin-SEPHAROSE were pooled, concentrated and applied onto a Superdex 75 FPLC gel filtration column. Aliquots of each fraction were tested for heparanase activity and protein profile. A correlation was found between the appearance of a major protein of about 63 kDa in fractions 4-7 and heparanase activity. This protein was not present in medium conditioned by control non-infected Sf21 cells and subjected to the same purification protocol.

Research on the involvement of heparanase/HS in tumor cell metastasis and angiogenesis has been handicapped by the lack of biological tools (i.e., molecular probes, antibodies) to explore a causative role of heparanase in disease. U.S. Pat. No. 5,968,822 offers, for the first time, a good opportunity to elucidate the enzyme's involvement in tumor metastasis and angiogenesis and the related diagnostic applications.

On the basis of the examples described below, it appears that cDNA and RNA probes, PCR primers, and anti-heparanase antibodies (heparanase specific molecular probes) can be applied to detect the heparanase gene and protein and hence for early diagnosis of micrometastases, autoimmune lesions, renal failure and atherosclerotic lesions using biopsy specimens, plasma samples, and body fluids.

Specificity and advantages over other reported antibodies: A variety of blood, tumor cells and certain normal cells have been shown to produce significant amounts of heparanase activity. The purification to homogeneity and characterization of mammalian heparanases has been difficult, primarily due to the lack of a convenient assay. Most reports contain only partial description with conflicting information. Oosta, et al. (22) described the purification of a human platelet heparanase with an estimated molecular mass of 134 kDa expressing an endoglucuronidase activity. Hoogewert, et al. (23) reported the purification of a 30 kDa human platelet heparanase which was shown to be an endoglucosaminidase that cleave both heparin and heparan sulfate essentially to disaccharides. They claimed that the holoenzyme consists of four subunits, each closely related to the CXC chemokines CTAPIII, NAP-2 and β-thromboglobulin (23). Freeman and Parish (24) have purified to homogeneity a 50 kDa platelet heparanase exhibiting endoglucuronidase activity. Likewise heparanase enzyme purified from human placenta and from hepatoma cell line (U.S. Pat. No. 5,362,641) had a molecular mass of approximately 48 kDa. A similar molecular weight was determined by gel filtration analysis of partially purified heparanase enzymes isolated form human platelets, human neutrophils and mouse B16 melanoma cells (our unpublished data). In contrast, heparanase purified from B16 melanoma cells by Nakajima, et al. (9, 26) had a molecular weight of 96 kDa. The latter enzyme has been localized immunochemically to the cell surface and cytoplasm of human melanoma lesions using a polyclonal antiserum (26) and in tertiary granules in neutrophils using monoclonal antibodies (26a), both directed against a putative amino terminal sequence from purified B16F10 melanoma cell heparanase (26). However, the melanoma heparanase amino terminal sequence was found to be characteristic of a 94 kDa glucose-regulated protein (GRP94/endoplasmin) that functions as a molecular chaperone which lacks heparanase activity (27). This result and a recent study using anti-endoplasmin antibody (28) suggest that the endoplasmin-like 98 kDa protein found in purified melanoma heparanase preparations is a contaminant (27, 28). This calls into question the previous heparanase immunolocalization studies carried out using the B16 melanoma heparanase amino terminal peptide antiserum (26). Likewise, antiserum directed against the amino terminal sequence of CTAP III was applied to immunolocalize the heparanase enzyme in biopsy specimens of human prostate and breast carcinomas (29, 30). Again, the validity of the results is questionable, since the possibility that CTAP III is a contaminant of the platelet preparation was not excluded. First, attempts to express heparanase active CTAPIII/NAP2 protein were unsuccessful and the recombinant CTAPIII/NAP2 chemokines failed to exhibit heparanase activity. Second, western blot analysis of the platelet enzyme purified by Freeman and Parish (24) with antibodies against human β-thromboglobulin or platelet factor-4 demonstrated that these and related proteins (e.g., CTAP-III and NAP-2) were not present in the purified platelet heparanase preparations (24). Moreover, while heparanase activity can be detected in purified preparations of β-thromboglobulin, it is probably due to contamination with the "classical" platelet heparanase since it exhibited an endo-beta-D-glucuronidase activity rather than an endoglucosaminidase activity (23), as reported by Hoogewerf et al. (Pikas et al. manuscript submitted for publication).

Our studies on the immunolocalization of CTAPIII in human biopsy specimens revealed a preferential localization of CTAP-III in cells (i.e., vascular endothelia cells, keratinocytes) that failed to express heparanase activity and vice versa. Finally, none of the sequences published by Hoogewerf et al (platelet CTAP-III/NAP-2) (23) or Jin et al. (B16 melanoma) (26) nor sequences of the bacterial heparin/heparan sulfate degrading enzymes (hep I & III) (30a) were found in our recombinant human heparanase that was cloned and expressed on the basis of sequences derived from the purified human placenta and hepatoma heparanases.

Several years ago we prepared rabbit polyclonal antibodies directed against our partially purified preparation of human placenta heparanase. These antibodies, referred to in U.S. Pat. No. 5,362,641, were later found to be directed against plasminogen activator inhibitor type I (PAI-1) that was co-purified with the placental heparanase. These findings led to a modification of the original purification protocol to remove the PAI-1 contaminant.

Collectively, it is evident that so far no one had succeeded in eliciting anti-heparanase antibodies.

Unlike the above described information, both the polyclonal and monoclonal antibodies described hereinunder were raised, for the first time, against a purified, highly active, recombinant enzyme. As further shown below these antibodies specifically recognizes the heparanase enzyme in cell lysates and conditioned media and does not cross-react with β-thromboglobulin, NAP-2, PAI-1 or bacterial heparinases I and III. They do recognize the mouse B16-F10 heparanase, the human platelet heparanases, and the heparanase enzymes produced by several human tumor cell lines and Chinese hamster ovary (CHO) cells. By virtue of being produced against a purified recombinant enzyme and their specificity, these antibodies appear highly appropriate for diagnostic purposes such as immunohistochemistry of biopsy specimens and quantitative ELISA of body fluids (e.g., plasma, urine, pleural effusions, etc.). Similarly, as presented in the Examples section hereinunder, both the molecular probes for in situ determination of the tissue distribution of the hpa gene and the cDNA primers for detection of the hpa mRNA in normal and malignant cells of human origin (e.g., leukemia and lymphoma cells, melanoma cells) can be applied, for the first time, for diagnosis of early events in tumor progression, metastatic spread and response to treatment.

SUMMARY OF THE INVENTION

According to the present invention there are provided heparanase specific molecular probes and their use in use in research and medical applications including diagnosis and therapy.

According to further features in preferred embodiments of the invention described below, there is provided an antibody elicited by a heparanase protein or an immunogenical portion thereof, the antibody specifically binds heparanase.

According to still further features in the described preferred embodiments the heparanase protein is recombinant.

According to still further features in the described preferred embodiments the elicitation is through in vivo or in vitro techniques, the antibody having been prepared by a process comprising the steps of (a) exposing cells capable of producing antibodies to the heparanase protein or the immunogenical part thereof and thereby generating antibody producing cells; (b) fusing the antibody producing cells with myeloma cells and thereby generating a plurality of hybridoma cells each producing monoclonal antibodies; and (c) screening the plurality of monoclonal antibodies to identify a monoclonal antibody which specifically binds heparanase.

According to still further features in the described preferred embodiments the antibody is selected from the group consisting of a polyclonal antibody and a monoclonal antibody.

According to still further features in the described preferred embodiments the polyclonal antibody is selected from the group consisting of a crude polyclonal antibody and an affinity purified polyclonal antibody.

According to further features in preferred embodiments of the invention described below, there is provided an oligonucleotide comprising a nucleic acid sequence specifically hybridizable with heparanase encoding nucleic acid.

According to further features in preferred embodiments of the invention described below, there is provided a pair of polymerase chain reaction primers comprising a sense primer and an antisense primers, each of the primers including a nucleic acid sequence specifically hybridizable with heparanase encoding nucleic acid.

According to further features in preferred embodiments of the invention described below, there is provided an antisense nucleic acid (RNA or DNA) molecule comprising a nucleic acid sequence specifically hybridizable with heparanase messenger RNA.

According to further features in preferred embodiments of the invention described below, there is provided a sense nucleic acid (RNA or DNA) molecule comprising a nucleic acid sequence specifically hybridizable with heparanase antisense RNA.

According to further features in preferred embodiments of the invention described below, there is provided a method of in situ detecting localization and distribution of heparanase expression in a biological sample comprising the step of reacting the biological sample with a detectable heparanase specific molecular probe and detecting the localization and distribution of the detectable heparanase specific molecular probe.

According to further features in preferred embodiments of the invention described below, there is provided a method of detecting heparanase expression in a biological sample comprising the step of reacting the biological sample with a detectable heparanase specific molecular probe and detecting said detectable heparanase specific molecular probe. Protein and nucleic acid dot blot application are envisaged.

According to still further features in the described preferred embodiments the biological sample is selected from the group consisting of cells and tissues.

According to still further features in the described preferred embodiments the biological sample is malignant.

According to still further features in the described preferred embodiments the malignancy is selected from the group consisting of a solid tumor and a hematopoietic tumor.

According to still further features in the described preferred embodiments the solid tumor is selected from the group consisting of carcinoma, adenocarcinoma, squameous cell carcinoma, teratocarcinoma, mesothelioma and melanoma, and further wherein the hematopoietic tumor is selected from the group consisting of lymphoma and leukemia.

According to still further features in the described preferred embodiments the solid tumor is a primary tumor, or a metastasis thereof, and is originated from an organ selected from the group consisting of liver, prostate, bladder, breast, ovary, cervix, colon, skin, intestine, stomach, uterus, pancreas.

According to still further features in the described preferred embodiments the detectable heparanase specific molecular probe is selected from the group consisting of a nucleic acid sequence hybridizable with heparanase encoding nucleic acid and an anti-heparanase antibody capable of specifically binding heparanase.

According to still further features in the described preferred embodiments the nucleic acid sequence hybridizable with heparanase encoding nucleic acid is selected from the group consisting of a synthetic oligonucleotide, an antisense heparanase RNA and heparanase DNA labeled by a detectable moiety.

According to further features in preferred embodiments of the invention described below, there is provided a method of detecting heparanase protein in a body fluid of a patient comprising the steps of reacting the body fluid with an anti-heparanase antibody and monitoring the reaction.

According to still further features in the described preferred embodiments the body fluid is selected from the group consisting of plasma, urine, pleural effusions and saliva.

According to still further features in the described preferred embodiments the body fluid is of a patient suffering from a condition selected from the group consisting of cancer, renal disease and diabetes.

According to still further features in the described preferred embodiments the renal disease is associated with diabetes.

According to still further features in the described preferred embodiments the anti-heparanase antibody is selected from the group consisting of a monoclonal antibody and a poly clonal antibody.

According to still further features in the described preferred embodiments reacting the body fluid with the anti-heparanase antibody is effected in solution.

According to still further features in the described preferred embodiments reacting the body fluid with the anti-heparanase antibody is effected on a substrate capable of adsorbing proteins present in the body fluid.

According to still further features in the described preferred embodiments the body fluid is of a patient suffering from myeloma, breast carcinoma, metastatic breast carcinoma, hemorrhagic nephritis, nephrotic syndrome, normoalbuminuric type I diabetes, microalbuminuric type I diabetes, kidney disorder, inflammation, sepsis, inflammatory and autoimmune disease.

According to further features in preferred embodiments of the invention described below, there is provided a method of detecting the presence, absence or level of heparanase transcripts in a biological sample comprising the steps of (a) extracting messenger RNA from the biological sample, thereby obtaining a plurality of messenger RNAs; (b) reverse transcribing the plurality of messenger RNAs into a plurality of complementary DNAs; (c) contacting the plurality of complementary DNAs with a pair of heparanase specific polymerase chain reaction primers, nucleoside triphosphates and a thermostable DNA polymerase; (d) performing a polymerase chain reaction; and (e) detecting the presence, absence or level of the polymerase chain reaction product.

According to further features in preferred embodiments of the invention described below, there is provided a method of detecting heparanase messenger RNA in a biological sample comprising the steps of reverse transcribing the messenger RNA into complementary DNA, contacting the complementary DNA with polymerase chain reaction oligonucleotides hybridizable to heparanase encoding nucleic acid, performing a polymerase chain reaction and monitoring for heparanase specific polymerase chain reaction products.

According to further features in preferred embodiments of the invention described below, there is provided a method of detecting the presence, absence or level of heparanase protein in a biological sample comprising the steps of (a) extracting proteins from the biological sample, thereby obtaining a plurality of proteins; (b) size separating the proteins; (c) interacting the size separated proteins with an anti-heparanase antibody; and (d) detecting the presence, absence or level of the interacted anti-heparanase antibody.

According to still further features in the described preferred embodiments the anti-heparanase antibody is selected from the group consisting of a polyclonal antibody and a monoclonal antibody.

According to still further features in the described preferred embodiments the size separation is effected by electrophoresis.

According to further features in preferred embodiments of the invention described below, there is provided a method of targeted drug delivery to a tissue of a patient, the tissue expressing heparanase, the method comprising the steps of providing a complex of a drug directly or indirectly linked to an anti-heparanase antibody and administering the complex to the patient.

According to further features in preferred embodiments of the invention described below, there is provided a method of treating a patient having a condition associated with heparanase expression comprising the step of administering an anti-heparanase antibody to the patient.

It is an object of the present invention to use a heparanase specific molecular probe for detection of the presence, absence or level of heparanase expression.

It is another object of the present invention to use a heparanase specific molecular probe for therapy of a condition associated with expression of heparanase.

It is yet another object of the present invention to use a heparanase specific molecular probe for quantification of heparanase in a body fluid.

It is still another object of the present invention to use a heparanase specific molecular probe for targeted drug delivery.

It is another object of the present invention to use a heparanase specific molecular probe as a therapeutic agent.

The present invention successfully addresses the shortcomings of the presently known configurations by providing a variety of heparanase specific molecular probes which can be used for research and medical applications including diagnosis and therapy.

BRIEF DESCRIPTION OF THE DRAWINGS

The invention herein described, by way of example only, with reference to the accompanying drawings, wherein:

FIGS. 9a-f demonstrate detection of hpa mRNA by in situ hybridization in specimens of human malignant melanoma and normal nevus. FIGS. 9a, c and d—metastatic human melanoma (3 different patients), FIG. 9b—non malignant nevus tissue. Labeling is not seen in the nevus tissue, as compared to intense staining of the metastatic melanoma. FIGS. 9e and f—same sections as in Figures c and d stained with hematoxylin-eosine.

FIGS. 10a-f demonstrate detection of hpa mRNA by in situ hybridization in specimens of normal and malignant human liver. Hepatocellular carcinoma (×200), hepatocellular carcinoma (×1000), liver adenocarcinoma, normal adult liver, embryonic liver and control sense staining of embryonic liver are shown respectively. Labeling is not seen in normal liver cells as compared to intense staining of embryonic and malignant liver cells.

FIGS. 11a-f demonstrate detection of hpa mRNA by in situ hybridization in specimens of normal and malignant human tissues. Adenocarcinoma of the ovary, normal ovary, squameous cell carcinoma of the cervix, normal cervix, colon adenocarcinoma and normal small intestine are shown respectively.

FIGS. 12a-f demonstrate detection of hpa mRNA by in situ hybridization in specimens of various human tumors. Positive staining of the hpa gene was clearly seen in adenocarcinoma of the stomach, teratocarcinoma, well differentiated endometrial adenocarcinoma, adenocarcinoma of the pancreas, mesothelioma, FIGS. 12a-e, respectively. Control, sense staining of human mesothelioma is shown in FIG. 12f.

DESCRIPTION OF THE PREFERRED EMBODIMENTS

Figure 1:
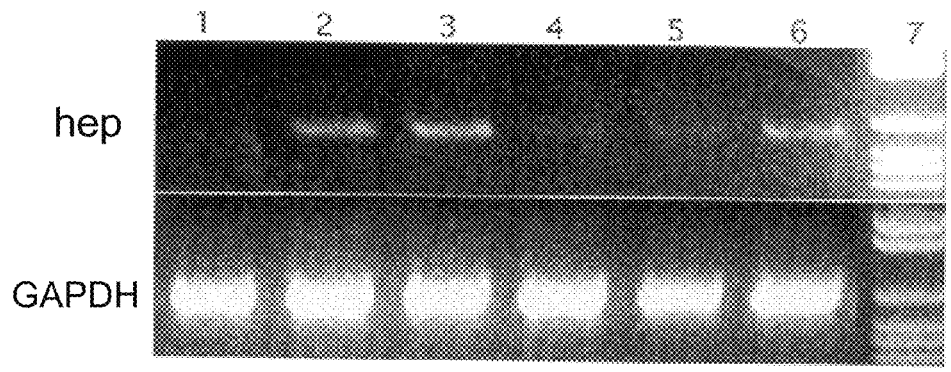
FIG. 1 demonstrates the expression of the human heparanase gene by human breast carcinoma cell lines with different metastatic potentials. Total RNA was isolated and subjected to semi quantitative RT-PCR (28 cycles) using human heparanase primers (hep) and primers for the GAPDH housekeeping gene. Reactions without reverse transcriptase demonstrated no amplification of genomic DNA contamination in the RNA samples (not shown). Lane 1, Non metastatic MCF-7 cells, lane 2, moderate metastatic MDA-231 cells, lane 3, highly aggressive MDA-435 cells, lane 4, minimal metastatic ZR-75 cells, lane 5, moderate metastatic MCF-ANeoT cells, lane 6, highly metastatic MCF-T$_6$ 3B cells; lane 7, DNA molecular weight marker VI (Boehringer Mannheim).

The present invention is of heparanase specific molecular probes which can be used in research and medical applications. Specifically, the present invention can be used for the detection and monitoring of malignancies, metastasis and other, non-malignant conditions, efficiency of therapeutic treatments, targeted drug delivery and therapy, using heparanase specific molecular probes, such as anti-heparanase antibodies (both poly- and monoclonal) and heparanase gene (hpa) derived nucleic acids, including, but not limited to, PCR primers, antisense oligonucleotide probes, antisense RNA probes, DNA probes and the like.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As shown in the Examples section below heparanase specific antibodies and/or nucleic acids reveals in situ expression (protein and/or messenger RNA) of heparanase in a variety of cells and tissues, especially in malignant cells and tissues, wherein the degree of expression corroborates with metastasis.

Therefore, according to one aspect of the present invention there is provided a method of in situ detecting localization and distribution of heparanase expression in a biological sample. The method comprises the step of reacting the biological sample with a detectable heparanase specific molecular probe and detecting the localization and distribution of the detectable heparanase specific molecular probe.

According to another aspect of the present invention, there is provided a method of detecting heparanase expression in a biological sample. The method comprises the step of reacting the biological sample with a detectable heparanase specific molecular probe and detecting the detectable heparanase specific molecular probe. Protein and nucleic acid dot blot application are envisaged.

As used herein in the specification and in the claims section below, the term "heparanase expression" refers mainly to the processes of transcription and translation, resulting in a catalytically active heparanase having endoglycosidase hydrolyzing activity which is specific for heparin or heparan sulfate proteoglycan substrates, as opposed to the activity of bacterial enzymes (heparinase I, II and III) which degrade heparin or heparan sulfate by means of β-elimination.

As used herein in the specification and in the claims section below, the term "biological sample" refers to cells and tissues, including, but not limited to cancer cells and tissues. The term further relates to body fluids, as further detailed below.

As used herein in the specification and in the claims section below, the term "detectable heparanase specific molecular probe" and its equivalent term "detectable heparanase molecular probe" both refer to a nucleic acid sequences hybridizable with heparanase encoding nucleic acid or to an anti-heparanase antibody capable of specifically binding heparanase. The nucleic acid sequence hybridizable with heparanase encoding nucleic acid is, for example, a synthetic oligonucleotide, an antisense heparanase RNA or heparanase DNA, and it is preferably labeled by the detectable moiety.

As used herein in the specification and in the claims section below, the term "detectable moiety" refers to any atom, molecule or a portion thereof, the presence, absence or level of which is directly or indirectly monitorable. One example include radioactive isotopes. Other examples include (i) enzymes which can catalyze color or light emitting (luminescence) reactions and (ii) fluorophores. The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable is preferably employed. The detectable moiety may be inherent to the molecular probe. For example, the constant region of an antibody can serve as an indirect detectable moiety to which a second antibody having a direct detectable moiety can specifically bind.

As used herein in the specification and in the claims section below, the term "antibody" refers to any monoclonal or polyclonal immunoglobulin, or a fragment of an immunoglobin such as sFv (single chain antigen binding protein), Fab1 or Fab2. The immunoglobulin could also be a "humanized" antibody, in which murine variable regions are fused to human constant regions, or in which murine complementarity-determining regions are grafted onto a human antibody structure (Wilder, R. B. et al., J. Clin. Oncol., 14:1383-1400, 1996). Unlike mouse or rabbit antibodies, "humanized" antibodies often do not undergo an undesirable reaction with the immune system of the subject. The terms "sFv" and "single chain antigen binding protein" refer to a type of a fragment of an immunoglobulin, an example of which is sFv CC49 (Larson, S. M. et al., Cancer, 80:2458-68, 1997).

According to one embodiment of the invention the biological sample is malignant, e.g., it is a solid tumor or hematopoietic tumor sample. The solid tumor can, for example, be of the types: carcinoma, adenocarcinoma, squameous cell carcinoma, teratocarcinoma, mesothelioma or melanoma, which are shown hereinunder in the Examples section to express heparanase in good correlation to the degree of metastasis. The hematopoietic tumor can, for example, be lymphoma or leukemia.

In some embodiments of the present invention the solid tumor is a primary tumor, or a metastasis thereof, and it originates from an organ such as, for example, liver, prostate, bladder, breast, ovary, cervix, colon, skin, intestine, stomach, uterus (including embryo) and pancreas.

As shown in the Examples section below, it was further found that body fluids (e.g., urine) of patients with certain conditions include catalitically active heparanase. These conditions include myeloma, breast carcinoma, metastatic breast carcinoma, hemorrhagic nephritis, nephrotic syndrome, normoalbuminuric type I diabetes, microalbuminuric type I diabetes, kidney disorder, inflammation, sepsis, inflammatory and autoimmune disease.

Therefore, according to another aspect of the present invention there is provided a method of detecting heparanase protein in a body fluid of a patient. The method comprises the steps of reacting the body fluid with an anti-heparanase antibody, either poly or monoclonal antibody, and monitoring the reaction. The body fluid is, for example, plasma, urine, pleural effusions or saliva. Monitoring the reaction may be effected by having the antibody labeled with a detectable moiety, or to use its constant region as an inherent detectable moiety, to which a second antibody which includes a detectable moiety can specifically bind.

Urine heparanase was detected in patients suffering from conditions such as cancer, renal disease and diabetes. In some cases the renal disease was associated with diabetes.

According to a preferred embodiment of the present invention reacting the body fluid with the anti-heparanase antibody is effected in solution. Alternatively, reacting the body fluid with the anti-heparanase antibody is effected on a substrate capable of adsorbing proteins present in the body fluid, all as well known in the art of antibody based diagnosis.

As further shown in the Examples section below, RT-PCR proves useful in detecting the presence, absence or level of heparanase transcripts in various biological samples.

Therefore, according to another aspect of the present invention there is provided a method of detecting the presence, absence or level of heparanase transcripts in a biological sample. The method comprises the following steps. First, messenger RNA (e.g., as a component of total RNA) is extracted from the biological sample, thereby a plurality of messenger RNAs are obtained. Second, the plurality of messenger RNAs are reverse transcribed into a plurality of complementary DNAs. Third, the plurality of complementary DNAs are contacted with a pair of heparanase specific polymerase chain reaction (PCR) primers, nucleoside triphosphates and a thermostable DNA polymerase (e.g., *Thermophilus aquaticus* DNA polymerase, native or recombinant) and a polymerase chain reaction is performed by temperature cycling, as well known in the art. Finally, the presence, absence or level of the polymerase chain reaction product is detected, e.g., by gel electrophoresis, by monitoring the incorporation of a detectable moiety into the product or any other applicable way, all as well known in the art.

As further shown in the Examples section below, protein blots and anti-heparanase antibodies prove useful in detecting the presence, absence or level of heparanase protein in various biological samples.

Therefore, further according to the present invention there is provided a method of detecting the presence, absence or level of heparanase protein in a biological sample. The method comprises the following steps. First, proteins are extracted from the biological sample, thereby a plurality of proteins are obtained. The protein extract may be a crude extract and can also include non-proteinacious material. Second, the proteins are size separated, e.g., by electrophoresis, gel filtration etc. Fourth, the size separated proteins are interacted with an anti-heparanase antibody, either poly or monoclonal antibody. Finally, the presence, absence or level of the interacted anti-heparanase antibody is detected. In case of gel electrophoresis the interaction with the antibody is typically performed following blotting of the size separated proteins onto a solid support (membrane).

In many cases it was shown that directly or indirectly (e.g., via liposomes) linking a drug (e.g., anti cancerous drug, such as, for example radio isotopes) to an antibody which recognized a protein specifically expressed by a tissue sensitive to the drug and administering the antibody-drug complex to a patient, results in targeted delivery of the drug to the expressing tissue.

Therefore, according to yet another aspect of the present invention there is provided a method of targeted drug delivery to a tissue of a patient, the tissue expressing heparanase. The method comprises the steps of providing a complex of a drug directly or indirectly linked to an anti-heparanase antibody and administering the complex to the patient. External radio imaging is also envisaged, wherein the drug is replaced with an imageable radio isotope. Endoscopic or laparoscopic imaging is also envisaged. In the latter cases the drug is typically replaced by a fluorescence or luminescence substance. These procedures may, for example, be effective in finding/destroying micrometastases.

In other cases, it was shown that administering an antibody capable of binding epitopes associated with certain tissues provide means of destroying such tissues by an elicited immune response.

Therefore, according to another aspect of the present invention there is provided a method of treating a patient having a condition associated with heparanase expression. The method comprises the step of administering an anti-heparanase antibody to the patient.

Further according to the present invention there is provided an antibody elicited by a heparanase protein (e.g., recombinant) or an immunogenical portion thereof, the antibody specifically binds heparanase. The antibody can be a poly or monoclonal antibody. If it is poly clonal and produced in vivo, it is preferably affinity purified, however crude antibody preparations are also applicable, all as shown and described in more detail in the Examples section hereinunder.

Preferably, the elicitation of the antibody is through in vivo or in vitro techniques, the antibody having been prepared by a process comprising the steps of, first, exposing cells capable of producing antibodies to the heparanase protein or the immonogenical part thereof and thereby generating antibody producing cells. second, fusing the antibody producing cells with myeloma cells and thereby generating a plurality of hybridoma cells each producing monoclonal antibodies, and third, screening the plurality of monoclonal antibodies to identify a monoclonal antibody which specifically binds heparanase.

Further according to the present invention there is provided an oligonucleotide comprising a nucleic acid sequence specifically hybridizable with heparanase encoding nucleic acid, be it heparanase DNA or RNA. The oligonucleotide may include natural nucleotides and/or nucleotide analogs, such as, but not limited to phosphorothioated analogs. Such oligonucleotides are readily synthesized provided that the sequence is known. Such oligonucleotides can be deduces, for example, from SEQ ID NOs: 1 and 3.

Further according to the present invention there are provided an antisense nucleic acid (RNA or DNA) molecule comprising a nucleic acid sequence specifically hybridizable with heparanase messenger RNA and a sense nucleic acid (RNA or DNA) molecule comprising a nucleic acid sequence specifically hybridizable with heparanase antisense RNA.

EXAMPLES

Reference is now made to the following examples, which together with the above descriptions, illustrate the invention in a non limiting fashion.

Experimental Methods and Materials

Cells: Cultures of bovine corneal endothelial cells (BCECs) were established from steer eyes as previously described (19, 31). Stock cultures were maintained in DMEM (1 gram glucose/liter) supplemented with 10% newborn calf serum, 5% fetal calf serum (FCS). bFGF (1 ng/ml) was added every other day during the phase of active cell growth (14, 15).

Preparation of sulfate labeled substrates: BCECs (second to fifth passage) were plated into 35 mm tissue culture plates at an initial density of $2\times10^5$ cells/ml and cultured in DMEM supplemented with 10% FCS and 5% dextran T-40 for 12 days. $Na_2^{35}SO_4$ (25 µCi/ml) was added on day 1 and 5 after seeding and the cultures were incubated with the label without medium change. The subendothelial ECM was exposed by dissolving (5 min, room temperature) the cell layer with PBS containing 0.5% Triton X-100 and 20 mM $NH_4OH$, followed by four washes with PBS. The ECM remained intact, free of cellular debris and firmly attached to the entire area of the tissue culture dish (14, 15, 20).

To prepare soluble sulfate labeled proteoglycans (peak I material), the ECM was digested with trypsin (25 µg/ml, 6 hours, 37° C.), the digest was concentrated by reverse dialysis, applied onto a SEPHAROSE 6B gel filtration column and the high molecular weight material ($K_{av}<0.2$, peak I) was collected (32). More than 80% of the labeled material was shown to be composed of heparan sulfate proteoglycans (11).

Heparanase activity: Cells ($1\times10^6$/35-mm dish), cell lysates or conditioned medium were incubated on top of $^{35}S$-labeled ECM (18 hours, 37° C.) in the presence of 20 mM phosphate or phosphate citrate buffer (pH 6.2). Cell lysates and conditioned media were also incubated with sulfate labeled peak I material (10-20 µl). The incubation medium was collected, centrifuged (18,000 g, 4° C., 3 min), and sulfate labeled material was analyzed by gel filtration on a SEPHAROSE CL-6B column (0.9×30 cm). Fractions (0.2 ml) were eluted with PBS at a flow rate of 5 ml/hour and counted for radioactivity using Bio-fluor scintillation fluid. The excluded volume ($V_o$) was marked by blue dextran and the total included volume ($V_t$) by phenol red. The latter was shown to comigrate with free sulfate (11, 20). Degradation fragments of HS side chains were eluted from SEPHAROSE 6B at $0.5<K_{av}<0.8$ (peak II) (11, 20). A nearly intact HSPG released from ECM by trypsin was eluted next to $V_O$ ($K_{av}<0.2$, peak I). Recoveries of labeled material applied on the columns ranged from 85 to 95% in different experiments.

Construction of heparanase expression vector: A BamHI-KpnI 1.3 kb fragment (nucleotides 450-1721 of the hpa sequence, SEQ ID NOs: 1 and 3, U.S. Pat. No. 5,968,822) was cut out from pfasthpa and cloned into pRSET-C bacterial expression vector (Invitrogen). The resulting recombinant plasmid pRSEThpaBK encodes a fusion protein comprised of His tag, a linker sequence and amino acids 130-543 of the heparanase protein (SEQ ID NOs: 2 and 3).

A 1.6 kb fragment of hpa cDNA was amplified from pfasthpa (a hpa cDNA cloned in pfastBac, see U.S. Pat. No. 5,968,822), by PCR using specific sense primer: (Hpu-550Nde)-5'-CGCATATGCAGGACGTCGTG GACCTG-3' (SEQ ID NO:4) and a vector specific antisense primer: (3'pFast) 5'-TATGATCCTCTAGTACTTCTCGAC-3' (SEQ ID NO:5). The upper primer introduced an NdeI site and an ATG codon preceding nucleotide 168 of hpa. The PCR product was digested by NdeI and BamHI and its sequence was confirmed. pRSEThpaBK was digested with NdeI and BamHI and ligated with the NdeI-BamHI hpa fragment. The resulting plasmid, designated pRSEThpaS1, encoded an open reading frame of 508 amino acids (36-543) of the heparanase protein, lacking the N-terminal 35 amino acids which are predicted to be a signal peptide. Expression constructs were introduced into E. coli BL21 (DEL3)pLysS cells (Stratagene), according to supplier's protocol.

Preparation of antigen: E. coli cells harboring the recombinant plasmid were grown at 37° C. overnight in Luria broth containing ampicillin and chloramphenicol. Cells were diluted 1/10 in the same medium, and the cultures were grown to an OD600 of approximately 0.5. Isopropyl-thiogalactoside (IPTG) (Promega) was added to a final concentration of 1 mM and the culture was incubated at 37° C. for 3 hours. Cells from induced cultures were cooled on ice, sedimented by centrifugation at 4,000×g for 20 minutes at 4° C., and resuspended in 0.5 ml of cold phosphate-buffered saline (PBS). Cells were lysed by sonication, and cell debris was sedimented by centrifugation at 10,000×g for 20 minutes. The resulting pellet was analyzed by 10% SDS-PAGE. The gel was stained with 1×PBS coomassie blue and the band of 45 kDa which contained the recombinant heparanase was cut out and crashed through a needle (21G) attached to a syringe. For immunization of mice, the crashed gel was incubated in PBS overnight at 4° C. and the protein diffused into the buffer was collected. Rabbits ware injected with gel homogenate.

The 55 kDa protein (508 amino acids) was purified from E. coli inclusion bodies by preparative SDS-PAGE, using a Model 491 Prep Cell (Bio-Rad) which is designed to purify proteins from complex mixtures by continuous elution electrophoresis. This antigen was used for ELISA screening.

Immunization—polyclonal antibodies: Two rabbits (designated 7640 and 7644) were immunized each with 200 µg of protein emulsified with equal volume of complete Freund's adjuvant. An equal amount of protein emulsified with incomplete Freund's was injected to each rabbit two weeks following the first injection and again after another four weeks. Ten days after the third injection the rabbits were bled and serum was examined for reactivity with recombinant heparanase. Four weeks after bleeding another boost was injected and 10 days later blood was collected.

Immunization—monoclonal antibodies: 6 to 8 weeks old female Balb/C mice were each immunized intradermally with 50 µg recombinant heparanase emulsified in 50 µl PBS complete Freund's adjuvant. Two to three weeks later the same amount of the emulsion was injected subcutaneously or intradermally at multiple sites in incomplete Freund's adjuvant. After 3 weeks 25 µg antigen in aqueous solution was injected intrapertoneally. 7-10 days later animals were bled and the titer of the relevant antibodies was determined. 3-4 weeks after the last boost, one or two animals were injected intraperitoneal with 20 µg of soluble antigen (in PBS) and 3-4 days later spleens were removed.

Fusion and cloning: The spleens of immunized mice were ground, splenocytes were harvested and fused with the NSO myeloma cells by adding 41% PEG. Hybridoma cells were grown in HAT-selective DMEM growth media containing 15% (v/v) HS (Beit Haemek), 2 mM glutamine, Pen-Strep-Nystatin solution (Penicillin: 10,000 units/ml, Streptomycin: 10 mg/ml, Nystatin: 1,250 units/ml), at 37° C. in 8% $CO_2$ containing atmosphere. Hybridoma cells were cloned by limiting dilution. Hybridomas producing Mabs to human heparanase were identified by reactivity with solid-phase immobilized human heparanase.

ELISA: Falcon polyvinyl plates were coated with 50 ng/well of baculovirus derived human heparanase (native) and 100 ng/well of E. coli derived human heparanase (55 kDa—non-active) in PBS (pH 7.2) overnight at 40° C. Hybridoma tissue culture supernatants were added to the wells, and incubated at room temperature for 2 hours. Binding of Mabs was then detected by incubation with HRP-conjugated goat anti mouse IgG (Fab specific) (Sigma), followed by development in o-phenylenediamine substrate (Sigma) and measurement of absorbencies at 450 nm. PBS with 0.05% Tween was used to wash the plates between incubations. Polyclonal rabbit anti human heparanase was used as positive control and negative control included coating with PBS or irrelevant supernatant.

Affinity purification of polyclonal antibodies: 200 μg of recombinant heparanase were separated on 10% SDS-PAGE. Following electrophoresis protein was transferred to a nitrocellulose membrane (Schleicher & Scuell). Membrane was stained with Ponceau S and the heparanase band was cut out. The membrane strip was blocked for 2 hours in TBS containing 0.02% Tween 20 and 5% skim milk. Antiserum was diluted 1:3 in blocking solution and incubated with the membrane for 16 hours. Membrane strip was washed with 0.15 M NaCl for 20 minutes and then with PBS for additional 20 minutes. Antibodies were eluted with 0.2 M glycine, 1 mM EDTA pH 2.8 for 20 minutes at room temperature, and then neutralized by addition of 0.1 volumes of 1 M Tris pH 8.0 and 0.1 volumes of 10×PBS. $NaNO_3$ was added to a final concentration of 0.02%.

Western blot: Proteins were separated on 4-20%, or 8-16% polyacrylamide ready gradient gels (Novex). Following electrophoresis proteins were transferred to Hybond-P nylon membrane (Amersham) (350 mA/100V for 90 minutes). Membranes were blocked in TBS containing 0.02% Tween 20 and 5% skim milk for 1-16 hours, and then incubated with antisera diluted in blocking solution. Blots were then washed in TBS-Tween, incubated with appropriate HRP-conjugated anti mouse/anti rabbit IgG, and developed using ECL reagents (Amersham) according to the manufacturer's instructions. Alternatively, an alkaline phosphatase conjugated anti-mouse/anti-rabbit IgG antibodies were used as secondary antibodies and blots were developed with FAST™ BCIP/NBT (Sigma) according to the supplier's instructions.

Expression of the heparanase gene in various cell types and tissues (RT-PCR): RT-PCR was applied to evaluate the expression of the hpa gene by various cell types. For this purpose, total RNA was reverse transcribed and amplified, using the following cDNA primers: Human hpa—Hpu-355 5'-TTCGATCCCAAGAAGGAATCAAC-3' (SEQ ID NO:6) and Hpl-229—5'-GTAGTGATGCCATGTAACTGAATC-3' (SEQ ID NO:7).

Expression pattern of the heparanase gene transcript (in situ hybridization). In situ hybridization enables determination of the distribution of hpa transcripts in normal and malignant tissues. For this purpose, thin sections of biopsy specimens were processed for in situ hybridization and hybridized with an antisense RNA probe to the hpa gene. The experiments have the resolution power to unambiguously identify the expressing cell type, be they tumor cells, tissue macrophages, mast cells or platelets. Sections were treated with proteinase K to expose the target RNA and to block non specific binding sites before addition of the probe (34). For in situ hybridization, two digoxigenin labeled probes were prepared, one in the sense direction and the other in the anti-sense direction. They were both transcribed from a fragment of about 624 bp of the hpa cDNA sequence (nucleotides 728-1351, SEQ ID NOs: 1 and 3) cloned in to the EcoRI-HindIII sites of the transcription vector pT3T7-Pac (a modified vector derived from pT3T7, Pharmacia), using T3 (for antisense) or T7 (for sense) RNA polymerase, according to the suppliers protocol. Slides were hybridized under appropriate conditions with the labeled probe and the hybridized probe is visualized using colorimetric reagents (NBT & BCIP) (34). Reactions were stopped when the desired intensity has been reached.

In situ detection of heparanase by antibodies: hpa-transfected and non transfected CHO cells were plated on 8-chamber tissue culture slides (Nunc). Cells were fixed in 95% ethanol, 5% acetic acid for 5 minutes at −20° C. Cells were permeabilized using permeabilization buffer (20 mM HEPES, pH 7.4; 300 mM Sucrose; 50 mM NaCl; 3 mM $MgCl_2$; 0.5% Triton X-100) for 4 minutes at 4° C. Endogenous peroxidases were blocked using 0.3% $H_2O_2$ in methanol and non specific binding sites were blocked using 5% horse serum in PBS. Monoclonal anti-heparanase antibody (supernatant of hybridoma) was applied and incubated with the cells overnight at room temperature. Antibody was washed away and biotinylated secondary antibody (horse-anti mouse, Vector, Vectastain ABC system) was added for 30 minutes at room temperature. Immunostaining was detected using Di Amino Benzidine and $H_2O_2$ (Sigma tablets) until desired staining-intensity was achieved. Slides were counterstained with Mayer's hematoxylin. Immunostaining with polyclonal antibodies was performed under the same conditions, affinity purified antibody was used at 1:500 dilution. Biotinylated horse anti-rabbit was used as a secondary antibody (Vector, Vectastain ABC system). Blood smears were prepared from a healthy donor. Fixation and staining were performed as described above.

Experimental Results

Figure 2A:
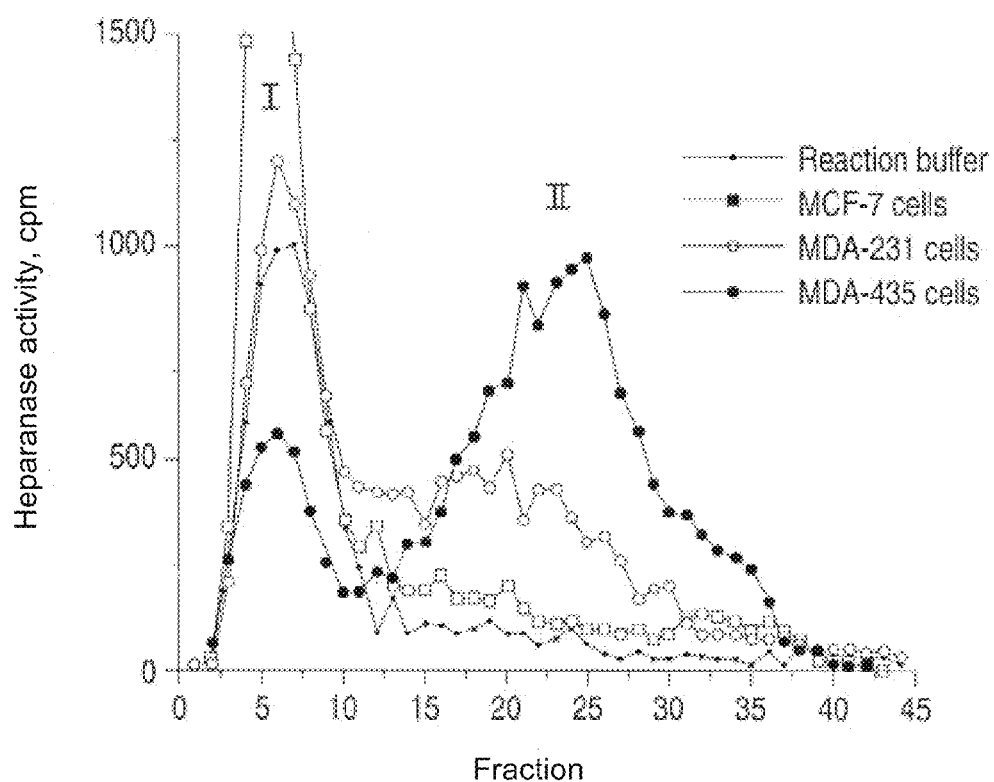
FIGS. 2a-b demonstrate heparanase activity expressed by human breast carcinoma cell lines with different metastatic potentials. Breast carcinoma cell lysates of the above described cell lines were incubated (24 hours, 37° C., pH 6.2) with $^{35}$S-HSPG isolated from intact subendothelial ECM. Heparanase mediated conversion of the heparan sulfate substrate (peak I) into low MW degradation fragments (peak II) was analyzed by gel filtration on SEPHAROSE 6B. Expression of the human hpa gene correlates with heparanase activity and metastasis in experimental animals.

Differential expression of the hpa gene in human breast carcinoma and breast carcinoma cell lines: Semi-quantitative RT-PCR was applied to evaluate the expression of the hpa gene by human breast carcinoma cell lines exhibiting different degrees of metastasis (35, 36). While the non-metastatic MCF-7 breast carcinoma line failed to express the expected 585 bp cDNA of the hpa gene (FIG. 1, lane 1), moderate (MDA 231, FIG. 1, lane 2) and highly (MDA 435, lane 3) metastatic breast carcinoma cell lines exhibited a marked increase in hpa gene expression. The differential expression of the hpa gene was reflected by a similar differential pattern of heparanase activity. As demonstrated in FIG. 2a, lysates of MCF-7 cells exhibited little or no heparanase activity, as compared to a moderate and high activity expressed by MDA-231 and MDA-435 cells, characterized by moderate and high metastatic potential in nude mice, respectively.

Figure 2B:
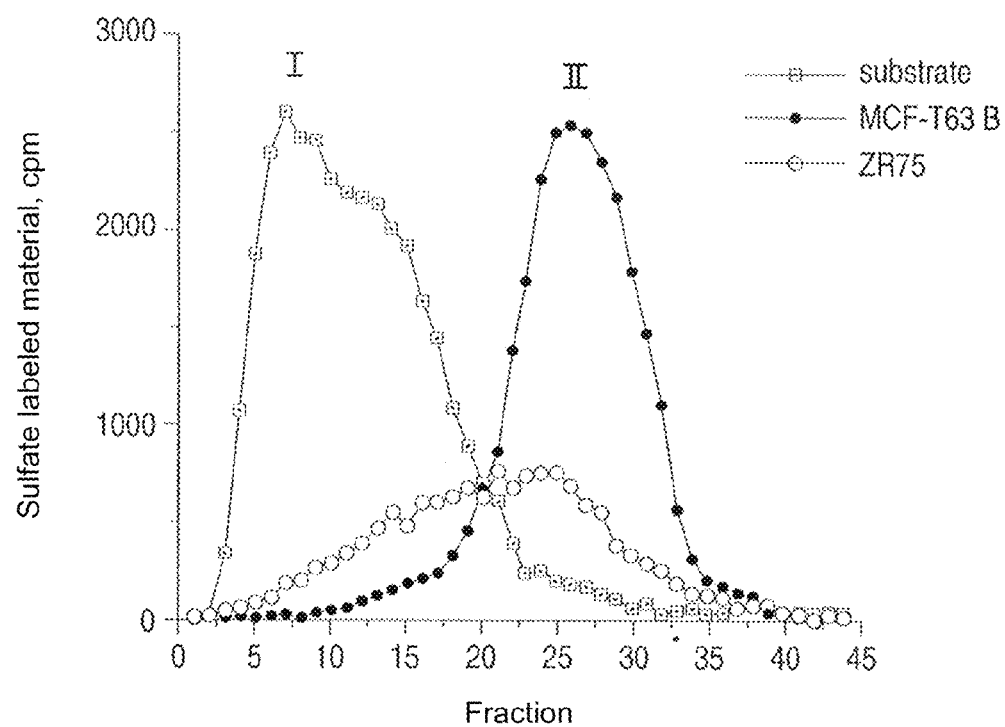
Figure 3A:
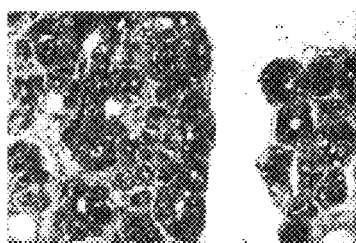
FIGS. 3a-f demonstrate detection of hpa mRNA by in situ hybridization in specimens of normal and malignant human breast tissue with antisense heparanase RNA probe: invasive carcinoma of the breast, pre-malignant fibrocystic breast tissue, adenocarcinoma of the breast, invasive breast carcinoma surrounding the area of tumor necrosis (not stained), normal breast tissue-reduction mammoplasty (antisense hpa probe), and normal breast tissue-reduction mammoplasty (control sense probe), respectively.
Figure 3B:
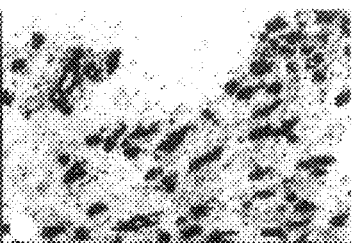
Figure 3C:
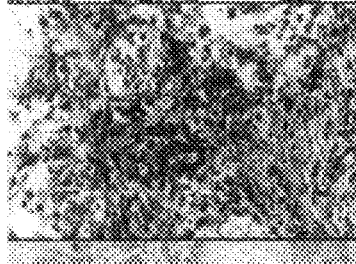
Figure 3D:
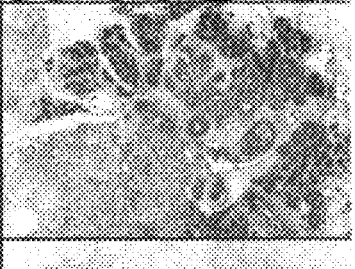
Figure 3E:
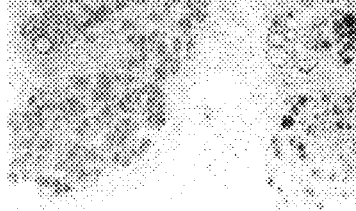
Figure 3F:
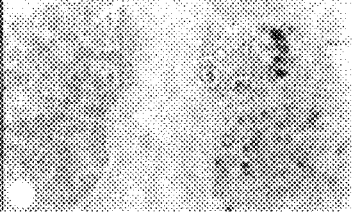

The same pattern of hpa gene expression and heparan sulfate degrading activity was observed in another model of breast cancer. While the ZR75 (=MCF10A) displastic breast cell line originated from fibrocystic breast epithelial cells showed little or no expression of the hpa gene (FIG. 1, lane 4), Ha-ras transfected ZR75 cell line (MCF10AT and MCF10AT3B) expressed the hpa gene (lanes 5 and 6) in correlation with their metastatic potential. The highly metastatic MCF10AT3B cells were derived from the third generation of xenografted tumors (36). The heparanase activity expressed by these cell lines was in correlation with their metastatic behavior (FIG. 2b).

In subsequent experiments, sense and antisense deoxigenin labeled RNA probes (600 bp fragment of the hpa cDNA) were employed to screen archivial paraffin embedded human breast tissue for expression of the hpa gene transcripts by in situ hybridization.

As shown in FIGS. 3a-f, massive expression of the hpa gene was observed in invasive breast carcinoma (3a) and breast adenocarcinoma (3c). The hpa gene was already expressed by differentiated epithelial cells of pre-malignant fibrocystic breast (3b) and in breast carcinoma tissue surrounding the area of tumor necrosis where little or no staining was observed (3d). Unlike the malignant tissue, normal breast tissue failed to express the hpa transcript as revealed by the lack of staining in tissue derived from reduction mammoplasty, both by the antisense (3e) and sense (3f) hpa probes.

Altogether, these results demonstrate a preferential expression of the hpa gene malignant breast carcinoma cells, indicating a potential application in early diagnosis of the disease, particularly in view of the positive staining detected already in the fibrocystic stage.

Figure 4:
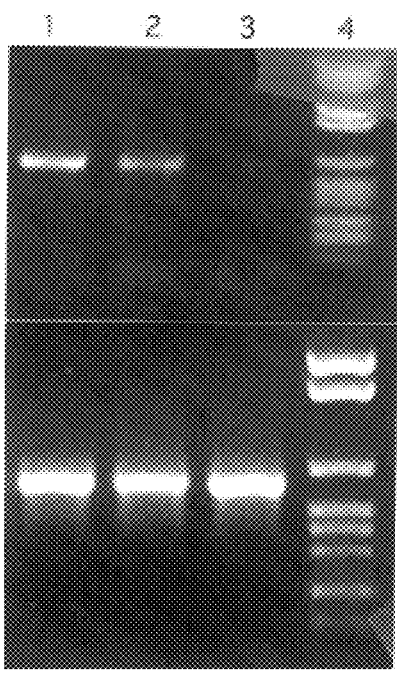
FIG. 4 demonstrate heparanase activity expressed by human prostate carcinoma cell lines. Expression of the human hpa gene by normal and malignant human prostate cells. Total RNA was isolated and subjected to RT-PCR using the appropriate human hpa primers (hep) and primers for the GAPDH housekeeping gene. Reactions without reverse transcriptase demonstrated no genomic DNA contamination in the RNA samples (not shown). Lane 1, metastatic DU145 human prostate carcinoma cells, lane 2, metastatic PC3 human prostate carcinoma cells, lane 3, normal human prostate tissue (biopsy specimen), lane 4, DNA molecular weight marker VI (Boehringer Mannheim).
Figure 5:
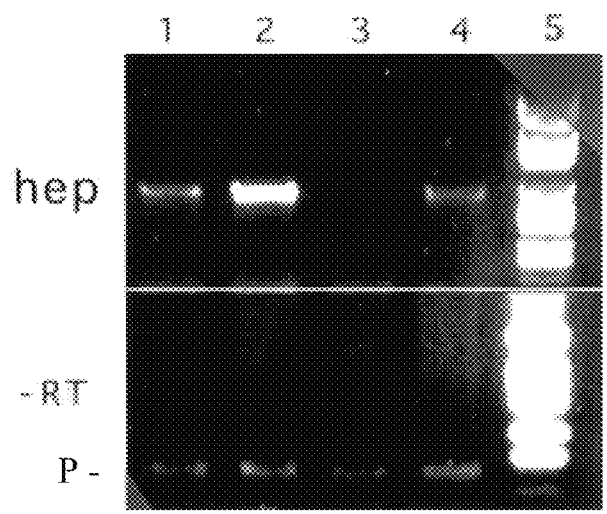
FIG. 5 demonstrate the expression of the hpa gene by high and low metastatic human bladder carcinoma and mouse T lymphoma cell lines. Total RNA was isolated and subjected to RT-PCR using human hpa primers. Lane 1, non metastatic MBT2 human bladder carcinoma cells, lane 2, highly metastatic T50 variant of MBT2 cells, lane 3, non-metastatic Eb mouse T-lymphoma, lane 4, highly metastatic ESb variant of the Eb mouse T-lymphoma cells, lane 5, DNA molecular weight marker VI (Boehringer Mannheim). –RT: negative control, without reverse transcriptase, P: non amplified primers.
Figure 6A:
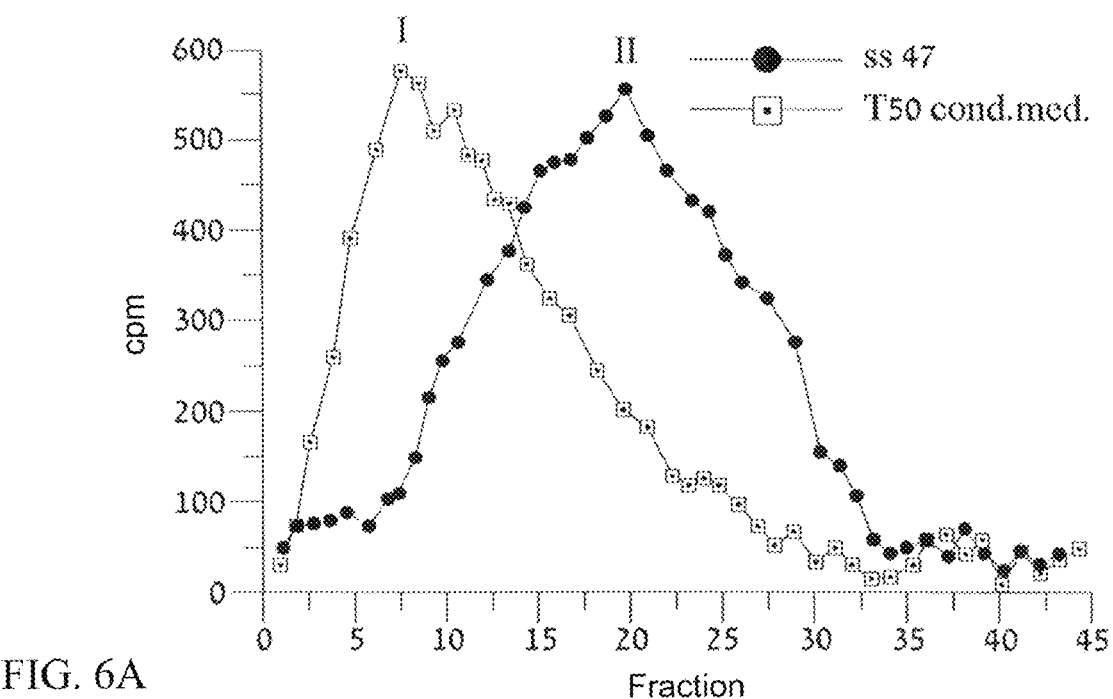
FIGS. 6a-c demonstrate heparanase activity expressed by high and low metastatic human bladder carcinoma cells. Media conditioned by low (MBT2) and high (T50) metastatic human bladder carcinoma cells were incubated (24 hours, 37° C., pH 6.2) with $^{35}$S-HSPG isolated from intact subendothelial ECM. Heparanase mediated conversion of the heparan sulfate substrate (peak I, ss 47) into low molecular weight degradation fragments (peak II) was analyzed by gel filtration on SEPHAROSE 6B. Expression of the human hpa gene correlates with heparanase activity and metastasis in experimental animals.
Figure 6B:
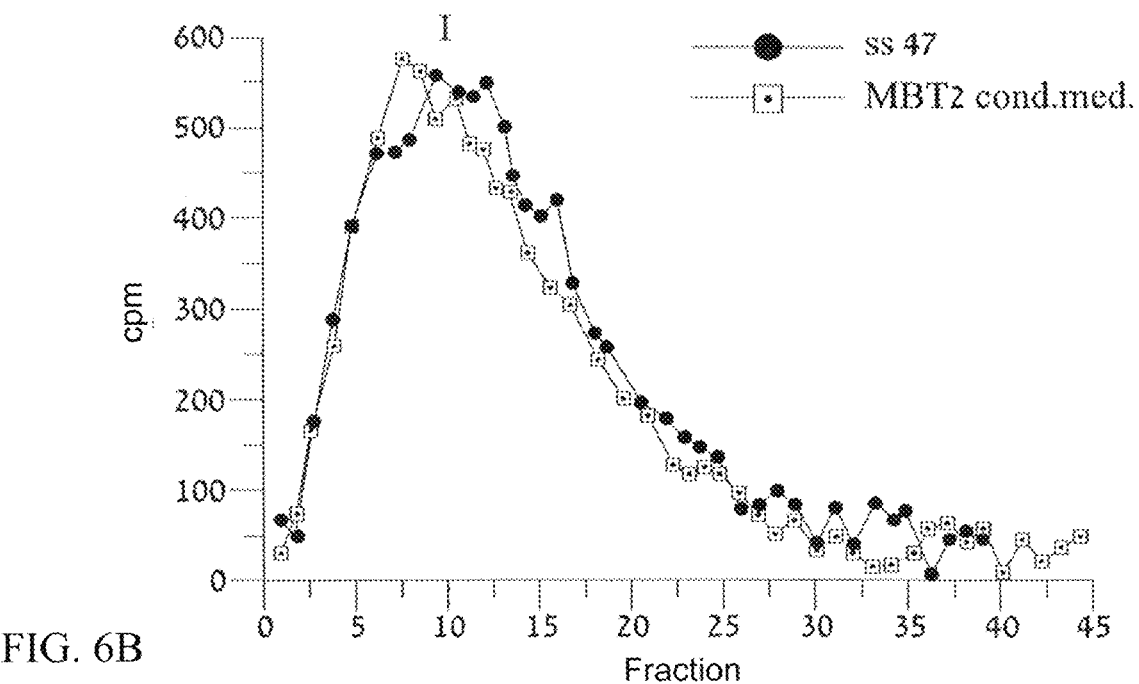
Figure 6C:
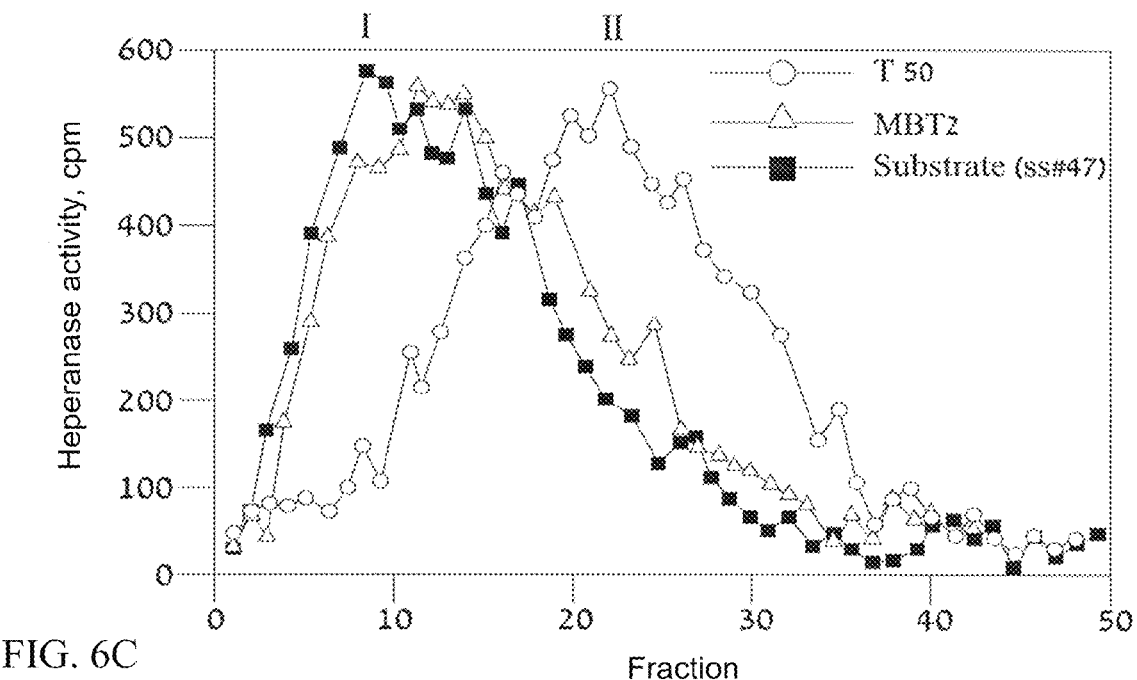

Human prostate and bladder carcinomas: Differential expression of the hpa mRNA was also suggested by RT-PCR analysis of several human prostate and bladder carcinoma cell lines. As demonstrated in FIG. 4, both DU145 (lane 1) and PC3 (lane 2) human prostate cell lines showed high expression of the hpa mRNA in contrast to lack of, or non-detectable, expression in a biopsy of normal adult prostate tissue (lane 3). Similarly, as demonstrated in FIG. 5, highly metastatic variant (T50) of the non-metastatic MBT2 human bladder carcinoma cell line, exhibited a much higher expression of the hpa gene (lane 2) as compared with the MBT2 cell line (lane 1). This difference was also reflected by high heparanase activity secreted into the culture medium of the aggressive T50 cells, as compared to no detectable activity in the medium of the parental MBT2 cells (FIGS. 6a-c). Again, the observed differential expression of the hpa gene and enzyme activity points toward potential application in the diagnosis of metastatic human prostate and bladder carcinomas.

Figure 7:
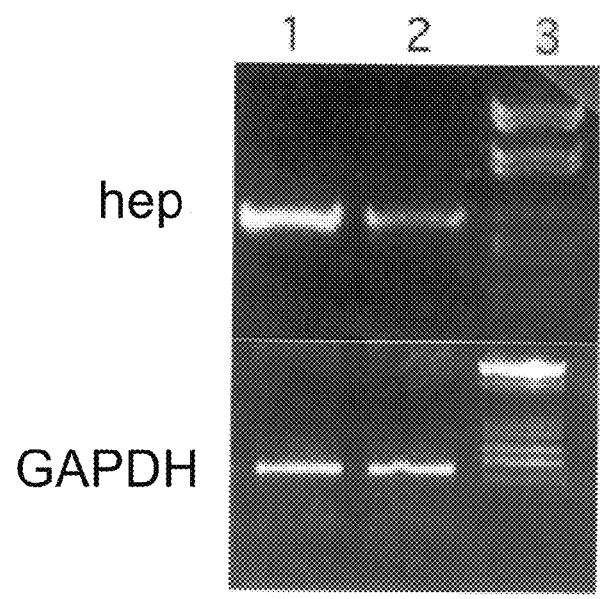
FIG. 7 demonstrate expression of the hpa gene by high and low metastatic B16 mouse melanoma cell lines. Total RNA was isolated and subjected to RT-PCR using hpa primers (hep) and primers for the GAPDH housekeeping gene. Reactions without reverse transcriptase demonstrated no genomic DNA contamination in the RNA samples. Lane 1, highly metastatic B16-F10 mouse melanoma cells, lane 2, low metastatic B16-F1 mouse melanoma cells, lane 3, DNA molecular weight marker VI (Boehringer Mannheim).

Mouse melanoma and T-lymphoma: Differential expression of the hpa MRNA and heparan sulfate degrading activity, correlated with the metastatic potential in mice was also demonstrated in studies with mouse B16 melanoma and T-lymphoma. In fact, the melanoma (9, 37) and lymphoma (11) cell systems were the first experimental systems pointing toward an important role of heparanase in tumor cell invasion and metastasis. Our cloning of the hpa cDNA, encoding for the heparanase enzyme, provides, for the first time, an evidence that the difference in enzymatic activity is due primarily to a preferential expression of the hpa gene by highly metastatic tumor cells. Thus, as demonstrated in FIGS. 5 and 7, the highly metastatic ESb lymphoma (FIG. 5, lane 4) and B16-F10 melanoma (FIG. 7, lane 1) cell lines, expressed the hpa gene to a much higher extent as compared to the parental low metastatic Eb lymphoma (FIG. 5, lane 3) and B16-F1 melanoma (FIG. 7, lane 2) cells. The respective high and low levels of heparanase activity by these cell lines were reported in earlier studies (9, 11, 37).

Figure 8A:
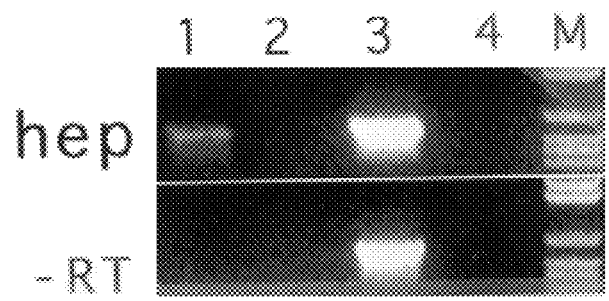
FIG. 8a demonstrate expression of the hpa gene by biopsy specimens from malignant human melanoma tumors and non-malignant benign nevus tissue which were processed for cell culture. Total RNA was isolated from subconfluent cultures and subjected to RT-PCR using human specific hpa primers (hep). Representative cases are shown. Lane 1, malignant melanoma, lane 2, non-malignant nevus tissue, lane 3, hpa-pcDNA plasmid (positive control), lane 4, negative control (no RNA), lane 5, DNA molecular weight marker VI (Boehringer Mannheim). Reactions without reverse transcriptase (–RT) demonstrated no genomic DNA contamination in the RNA samples.
Figure 8B:
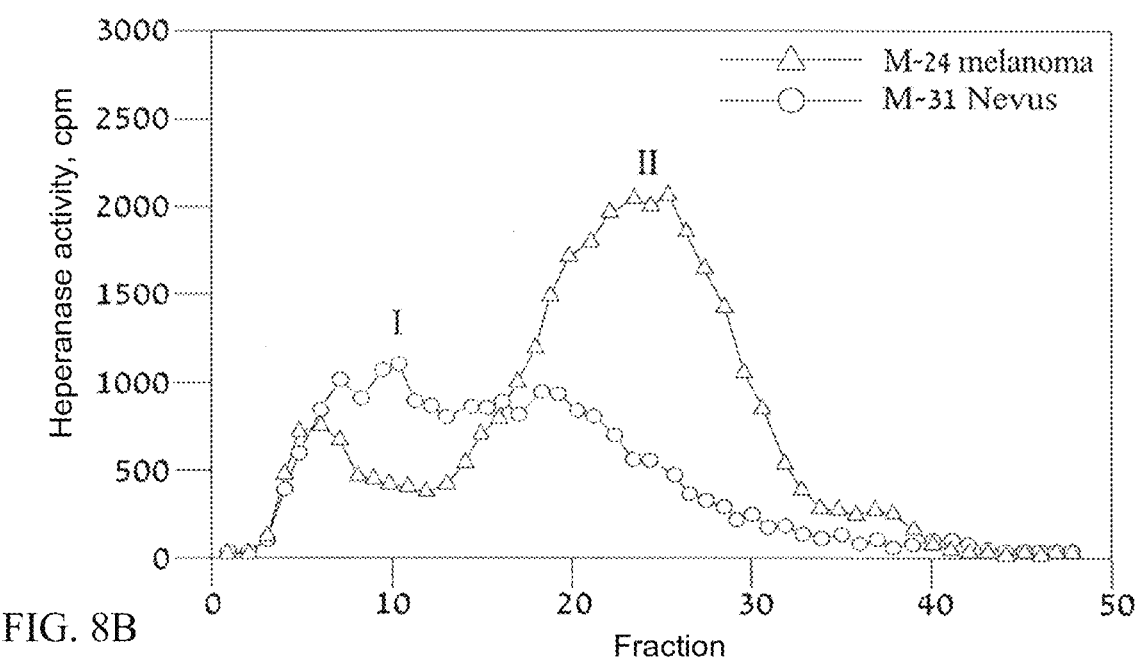
FIG. 8b demonstrates heparanase activity expressed by cultured cells derived from malignant melanoma (patient M-24) and non-malignant nevus tissue (patient M-31). Cultured cells were seeded on sulfate labeled ECM. Labeled degradation fragments released into the incubation medium were subjected to gel filtration on SEPHAROSE 6B.

Human melanoma: Preferential expression of the hpa gene and enzyme activity was also observed in cells derived from biopsies of human melanoma and normal nevus tissue. Biopsy specimens of malignant melanoma are routinely processed for cell culture in the department of Oncology (Hadassah Hospital, Jerusalem) for immunotherapy purposes. Cultured cells derived from 16 out of 16 patients (see also Table 1, below) expressed the hpa gene, as revealed by RT-PCR (FIG. 8a, lane 1, a representative patient). Melanoma cells derived from 3 of these patients were tested for degradation of soluble heparan sulfate proteoglycans and were found to be highly active (FIG. 8b). In contrast, cells derived from a non-malignant nevus tissue showed no detectable expression of the hpa mRNA (FIG. 8a, lane 2) and no enzyme activity (FIG. 8b).

Similar results were obtained using archivial paraffin embedded biopsy specimens and in situ hybridization. Again, cytoplasmic labeling of the hpa mRNA was observed in tissue sections of metastatic specimens derived from 3 different patients with malignant melanoma (FIGS. 9a and 9c-d), but not from a non-malignant nevus (FIG. 9b). Altogether, these results imply a potential use of hpa specific primers, nucleic acid probes and antibodies in early diagnosis of melanoma metastasis.

Human liver carcinoma: The heparanase enzyme was first purified in our laboratory from a human hepatoma cell line (Sk-Hep-1). In fact, amino acid sequences derived from the purified hepatoma heparanase were used to clone the hpa gene. In situ hybridization studies revealed an intense expression of the hpa gene in tissue sections derived from human heaptocellular carcinoma (FIGS. 10a-b) and liver adenocarcinoma (FIG. 10c). The hpa mRNA was not expressed by adult normal liver tissue (FIG. 10d). It was expressed, however, in embryonic human liver (FIG. 10e). Each of these examples clearly supports the use of heparanase specific molecular probes as tools for early diagnosis of human cancer and its spread and response to anti-cancer treatments.

Other human tumors: A preferential expression of the hpa gene was clearly observed by in situ hybridization performed with biopsy specimens of several different human carcinomas in comparison with their normal tissue counterparts. As demonstrated in FIGS. 11a-f, an intense expression of the hpa gene was observed in tissue sections derived from adenocarcinoma of the ovary (FIG. 11a), squameous cell carcinoma of the cervix (FIG. 11c), and colon adenocarcinoma (FIG. 11e). In contrast, there was little or no expression of the hpa mRNA in human tissue sections derived from normal ovary (FIG. 11b), cervix (FIG. 11d) and small intestine (FIG. 11f). The few cells stained in the normal tissue specimens were single infiltrating macrophages and neutrophils.

Positive staining of the hpa gene was also clearly seen in adenocarcinoma of the stomach (FIG. 12a), teratocarcinoma (FIG. 12b), well differentiated endometrial adenocarcinoma (FIG. 12c), adenocarcinoma of the pancreas (FIG. 12d), and mesothelioma (FIG. 12e). Each of these examples clearly supports the use of heparanase specific molecular probes as tools for early diagnosis of human cancer and its spread and response to anti-cancer treatments.

Figure 13A:
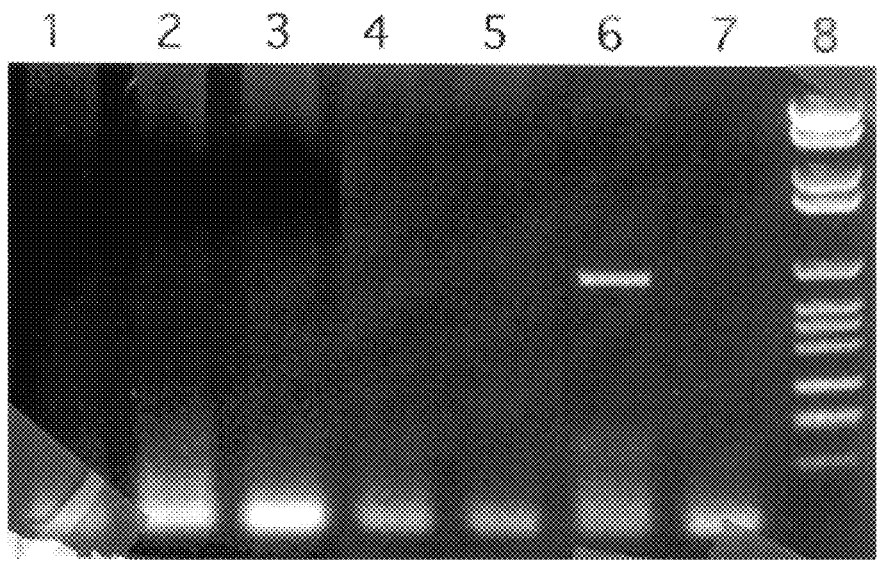
FIGS. 13a-b demonstrate expression of heparanase in human leukemias and lymphomas. Peripheral white blood cells of patients with various types of leukemia and lymphoma were isolated and tested for expression of the human hpa gene. For this purpose, total RNA was isolated and subjected to RT-PCR using human specific hpa primers. Reactions without reverse transcriptase demonstrated no genomic DNA contamination in the RNA samples. Peripheral white blood cells of different patients with chronic lymphocytic leukemia (FIG. 13a, lanes 1-5) were isolated and tested for expression of the human hpa gene. 13a Lane 6, hpa-pcDNA plasmid (positive control), lane 7, negative control (no reverse transcriptase), lane 8, DNA molecular weight marker VI (Boehringer Mannheim). Representative patients with various types of leukemia and lymphoma are shown in FIG. 13b. Lane 1, acute myelocytic leukemia, lane 2, Chronic lymphocytic leukemia (atypical B cell), lane 3, acute myelocytic leukemia (M5), lane 4, hairy cell leukemia, lane 5, non-hodjkin lymphoma (mature B cells), lane 6, non-hodjkin lymphoma (mature B cells), lane 7, chronic lymphocytic leukemia (stage I), lane 8, acute myelocytic leukemia (M2), lane 9, chronic myelocytic leukemia, lane 10, chronic lymphocytic leukemia (stage II), lane 11, acute lymphocytic leukemia, lane 12, chronic lymphocytic leukemia (stage III), lane 13, acute myelocytic leukemia (M1), lane 14, acute myelocytic leukemia (M3), lane 15, hpa-pcDNA plasmid (positive control), lane 16, negative control (no reverse transcriptase), lane 17, DNA molecular weight marker VI (Boehringer Mannheim).
Figure 13B:
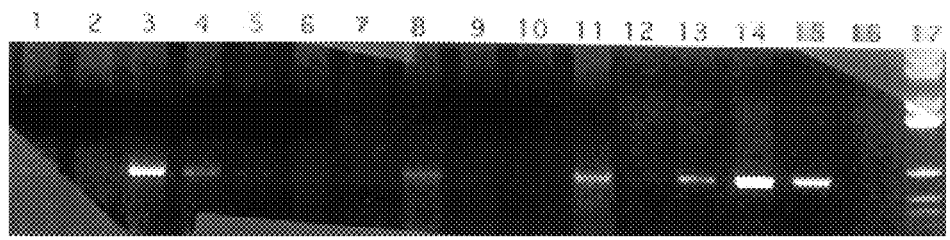
Figure 14:
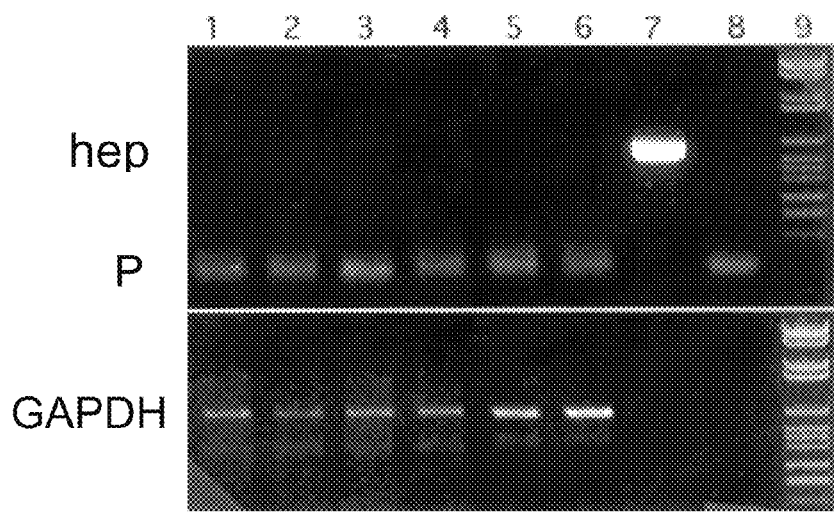
FIG. 14 demonstrates no expression of the hpa gene by normal human umbilical cord white blood cells. Total RNA was isolated and subjected to RT-PCR using hpa primers (hep) and primers for the GAPDH housekeeping gene. Reactions without reverse transcriptase demonstrated no genomic DNA contamination in the RNA samples. Lanes 1-6, white blood cell preparations from 6 different umbilical cords, lane 7, hpa-pcDNA plasmid (positive control), lane 8, negative control (no reverse transcriptase), lane 9, DNA molecular weight marker VI (Boehringer Mannheim).
Figure 15:
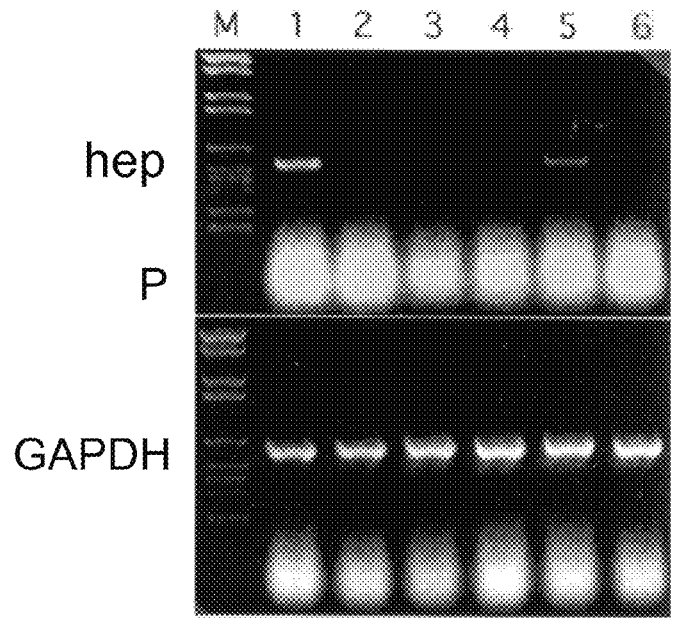
FIG. 15 demonstrates expression of the hpa gene by leukemia and lymphoma cell lines. Total RNA was isolated and subjected to RT-PCR using hpa primers (hep) and primers for the GAPDH housekeeping gene. Reactions without reverse transcriptase demonstrated no genomic DNA contamination in the RNA samples. Lane 1, normal B lymphoblastoid cell line (Monga), lane 2, Burkitt B lymphoma (Raji), lane 3, Burkitt B lymphoblasts (Daudi), lane 4, Burkitt B lymphoblasts (non Ebv, DG-75), lane 5, erythroleukemia (K-562), lane 6, pre B lymphoma (nalm$_6$), M=DNA molecular weight marker VI (Boehringer Mannheim).

Human leukemia and lymphoma: We have previously applied time consuming measurements of heparanase activity and demonstrated that heparanase is expressed and readily secreted by acute and chronic human myeloid leukemic cells (AML and CML), but not by chronic lymphocytic leukemic cells (CLL). The availability of heparanase specific primers enables a more sensitive and rapid determination of hpa gene expression by human leukemia and lymphoma cells. For this purpose, peripheral white blood cells (derived from patients with leukemia and lymphoma) were purified on Ficoll-hypack and subjected to total RNA isolation and RT-PCR determination of the hpa mRNA. Altogether, cells of 69 patients were tested. Representative patients are presented in FIGS. 13a-b and the results are summarized in Table 1 below. Cells from 31 out of 31 patients with CLL showed no detectable expression of the hpa gene (FIG. 13a, lanes 1-5, FIG. 13b, lanes 2, 7, 10 and 12) regardless of the stage of the disease. Similar results were obtained with cells from 4 out of 4 patients with non-Hodjkin lymphoma (NHL) (FIG. 13b, lanes 5 and 6). Both the CLL and NHL cells represent primarily differentiated B cells. In contrast, the hpa mRNA was expressed by cells derived from 14 out of 14 patients with AML (FIG. 13b, lane 11). These cells represent undifferentiated myeloblasts of neutrophils and monocyte origin. The hpa mRNA was expressed in cells of 1 out of 3 patients with CML, and 2 out of 2 patients with acute lymphocytic leukemia. Surprisingly, umbilical cord blood derived white blood cells showed little (one case) or no expression (13 additional cases) of the hpa gene in different cord blood samples (FIG. 14, Table 1, below). These cord blood preparations are enriched with hematopoietic stem cells. Studies with established cell lines (FIG. 15) revealed no expression of the hpa mRNA in Burkitt B lymphoma (i.e., Raji, Daudi, DG-75, lanes 2-4, respectively), as opposed to mature normal B (Ebv transformed) lymphoblastoid cell line (i.e., monga, FIG. 15, lane 1) and erythroleukemia (K-562, lane 5).

Apparently, heparanase expression can distinguish between differentiated B cell lymphoma (CLL and NHL) and undifferentiated myelocytic and lymphoblastoid leukemia (AML and ALL) (Table 1). The lack of hpa gene expression by umbilical cord white blood cells may enable to distinguish between early normal white blood cells (hpa negative) and early leukemic cells (hpa positive). Furthermore, the presence of heparanase may distinguish between early lymphatic leukemic cells (hpa positive) and late B leukemia and lymphoma cells (hpa negative).

TABLE 1

Expression of hpa mRNA (RT-PCR) in human leukemia, lymphoma and melanoma

Figure 16A:
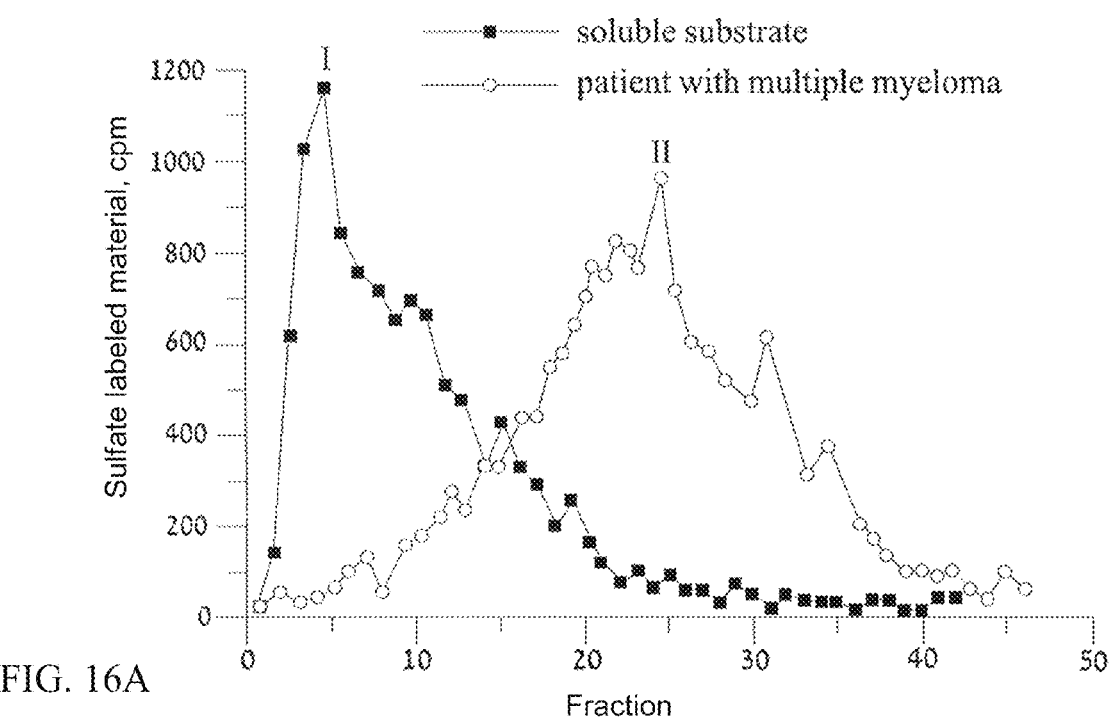
FIGS. 16a-h demonstrate urinary heparanase activity. Urine samples (o) of healthy donor (16d) and patients with multiple myeloma (16a), bilateral breast carcinoma (16b), metastatic breast carcinoma (16c), hemorrhagic nephritis (16e) nephrotic syndrome (16f), normoalbuminuric (16g) and microalbuminuric type I diabetes (16h) were incubated (24 hours, 37° C., pH 6.2) with $^{35}$S-HSPG (50 µl) isolated from intact subendothelial ECM (♦). Heparanase mediated conversion of the heparan sulfate substrate (peak I) into low molecular weight degradation fragments (peak II) was analyzed by gel filtration on SEPHAROSE 6B.
Figure 16B:
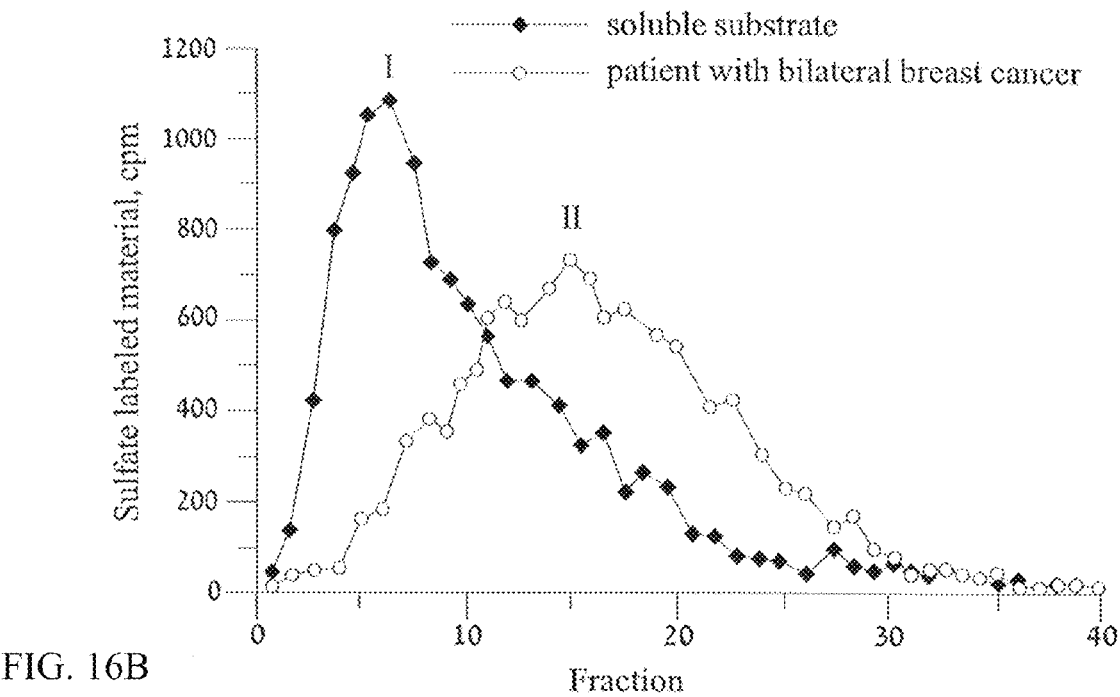
Figure 16C:
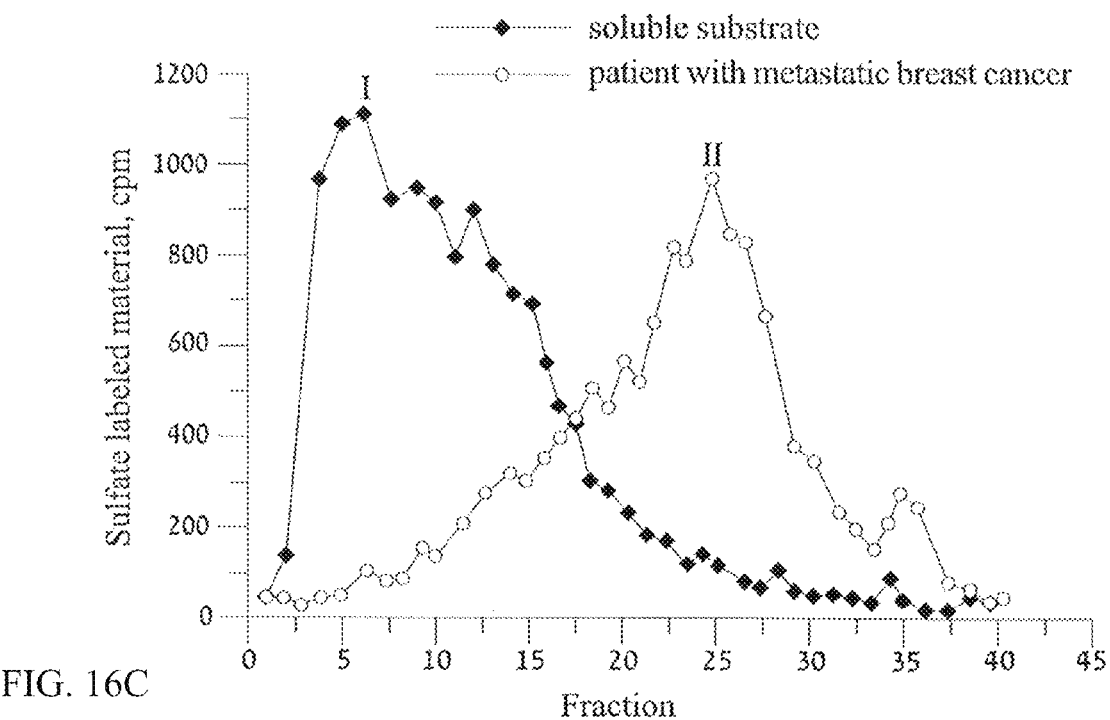
Figure 16D:
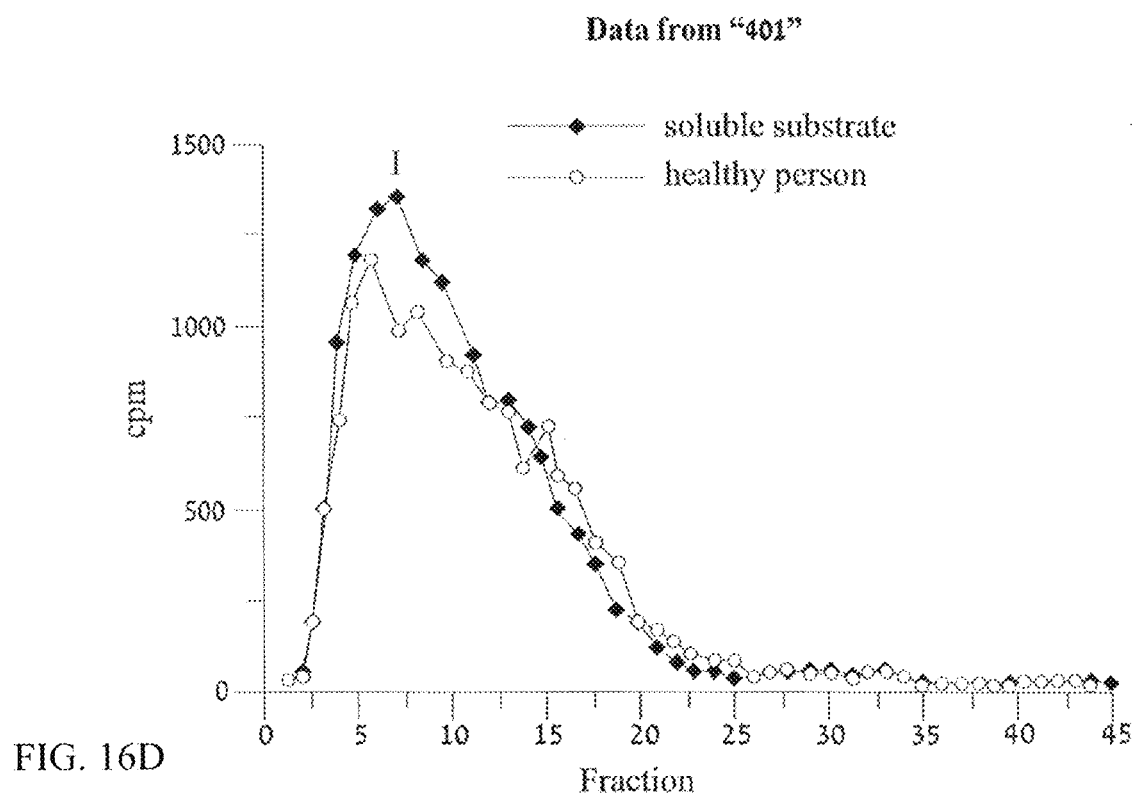

| Type | # of patients | # hpa positive | # hpa negative |
|---|---|---|---|
| CLL | 31 | 0 | 31 |
| AML | 14 | 14 | 0 |
| ALL | 2 | 2 | 0 |
| CML | 3 | 1 | 2 |
| NHL | 4 | 0 | 4 |
| Cord blood | 14 | 1 | 13 |
| Melanoma | 16 | 16 | 0 |
| Nevus (normal) | 3 | 0 | 3 | patients. Three examples are given in FIGS. 16a-c. High levels of heparanase activity were determined in the urine of patients with an aggressive disease (primarily breast carcinoma, FIGS. 16b-c, multiple myeloma, FIG. 16a) and there was no detectable activity in the urine of healthy donors (FIG. 16d). A more sensitive ELISA is expected to detect the heparanase protein at early stages of the disease. Urine may also contain heparanase inhibitors (i.e., GAGs) and hence an activity assay may underestimate the number of patients with positive urinary heparanase protein.

Heparanase activity in the urine of diabetic patients: Reduction in glomerular basement membrane (GBM) heparan sulfate proteoglycan (HSPG) is responsible for the microalbuminuria and proteinuria of diabetic nephropathy. We identified heparanase activity in cultured rat mesangial cells and postulated that the reduction in glomerular HSPG is secondary to increased glomerular heparanase activity and that the latter will be manifested by an increase in urinary heparanase. Urinary heparanase activity was tested in samples from 70 patients with type I diabetes and in 40 sex and age matched controls, as described above. The results are summarized in Table 2 below. Fifty patients were normoalbuminuric (NA) while 20 had microalbuminuria (MA). Urinary heparanase activity was detected in 13 of 70 (19%) diabetic patients while it was absent in the control group (p=0.002). Sixteen percent of the NA patients and 25% of the MA patients showed urinary heparanase activity (FIGS. 16g-h). Interestingly, over 80% of the heparanase positive patients were females. Heparanase positive patients had significantly higher blood glucose (p=0.0005) and HbA1C (p=0.03) levels compared with heparanase negative diabetic patients. This is the first study suggesting a role for heparanase in the pathogenesis of diabetic nephropathy. Urinary heparanase may be an early marker for renal involvement in type I diabetic patients, anteceding MA. The presence of heparanase activity in the urine of normo and microalbuminuric IDDM (insulin dependent diabetic mellitus) patients, is most likely due to diabetic nephropathy, the most important single disorder leading to renal failure in adults.

TABLE 2

Heparanase activity in urine of IDDM patients

| | No. of patients | Averaged Age | Sex | Disease duration | Blood pressure | GFR | Heparanase positive |
|---|---|---|---|---|---|---|---|
| Normo-albuminuria | 50 | $26.2 \pm 8.5$ years | 26 males 24 females | $16.5 \pm 7.3$ years | $112 \pm 17$ | $134 \pm 25$ ml/min/1.73 m$^2$ | 8/50 (16%) |
| Micro-albuminuria | 20 | $26.5 \pm 11.2$ years | 10 males 10 females | $14.5 \pm 7.9$ years | $115 \pm 13$ | $128 \pm 26$ ml/min/1.73 m$^2$ | 5/20 (25%) |

Heparanase activity in the urine of cancer patients: In an attempt to elucidate the involvement of heparanase in tumor progression and its relevance to human cancer, we screened urine samples for heparanase activity. Heparanase activity was determined by incubation of urine with soluble sulfate labeled proteoglycans obtained by trypsin digestion of metabolically Na$_2$$^{35}$SO$_4$ labeled subendothelial extracellular matrix. Heparanase activity resulted in conversion of a high molecular weight (MW) sulfate labeled substrate into low MW heparan sulfate degradation fragments as determined by gel filtration analysis. Heparanase activity was detected in the urine of 21 (renal cell carcinoma, breast carcinoma, rabdomyosarcoma, stomach cancer, myeloma) out of 157 cancer Repeated determination of urinary heparanase in 9 IDDM patients yielded similar results (6 negative and 3 positive) to the initial analysis performed 3 months earlier. Our results suggest that heparanase activity may play a role in the regulation of the number of HSPG anionic sites in the GBM and hence may modulate the permselective properties of the glomerular basement membrane.

Heparan sulfate contributes to the assembly and integrity of the ECM through binding to various ECM molecules such as collagen, laminin, fibronectin, thrombospondin and tenascin. Cleavage of heparan sulfate may therefore result in disassembly of the ECM leading to a loss of its barrier properties. We have identified heparanase activity expressed by mesanglial cells (not shown). Once heparanase is secreted by stimulated mesangial cells it will degrade heparan sulfate in the GBM thus allowing its passage into the urinary space.

Figure 16E:
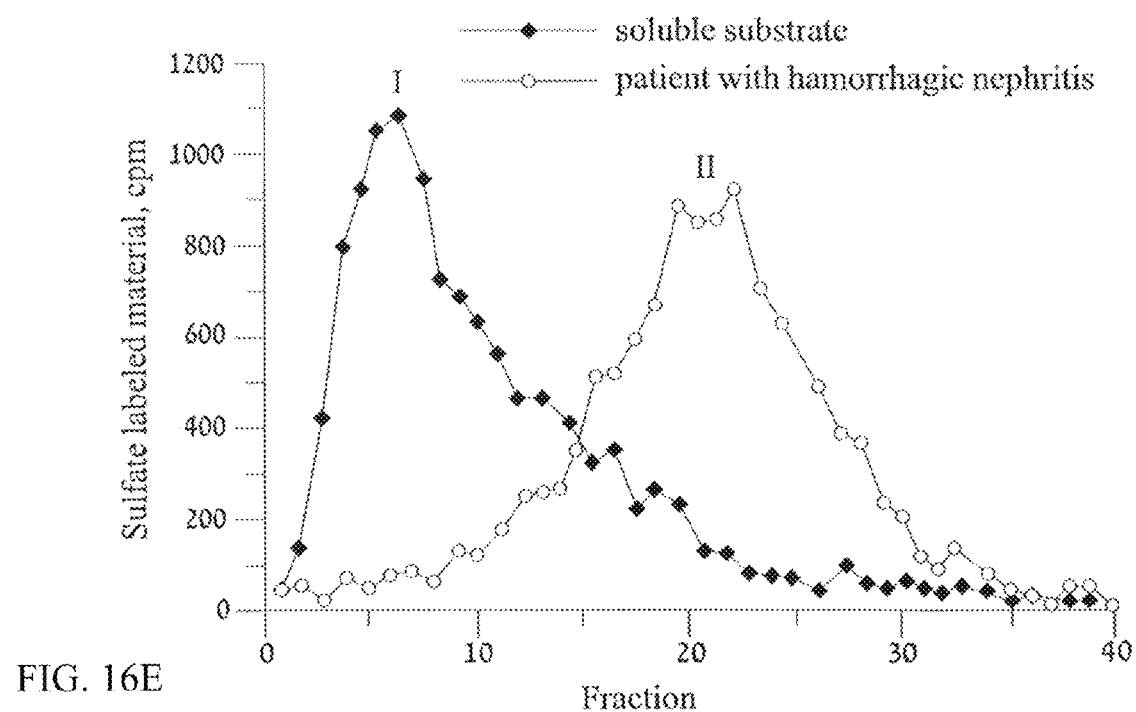
Figure 16F:
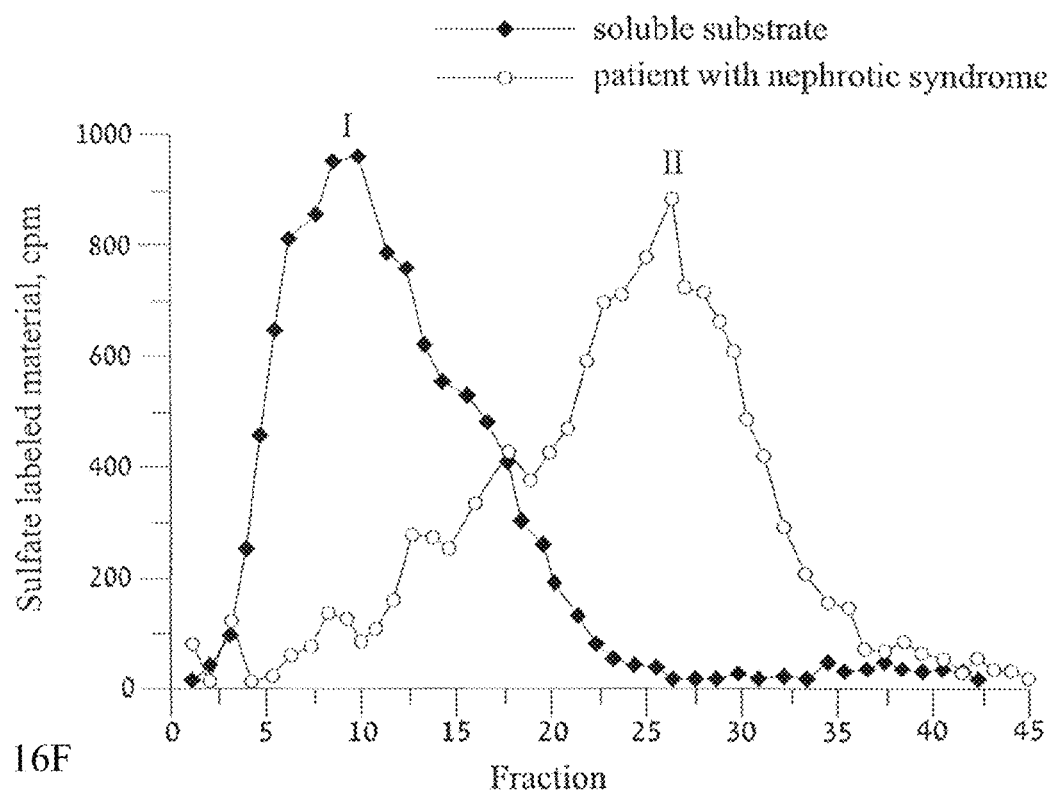
Figure 16G:
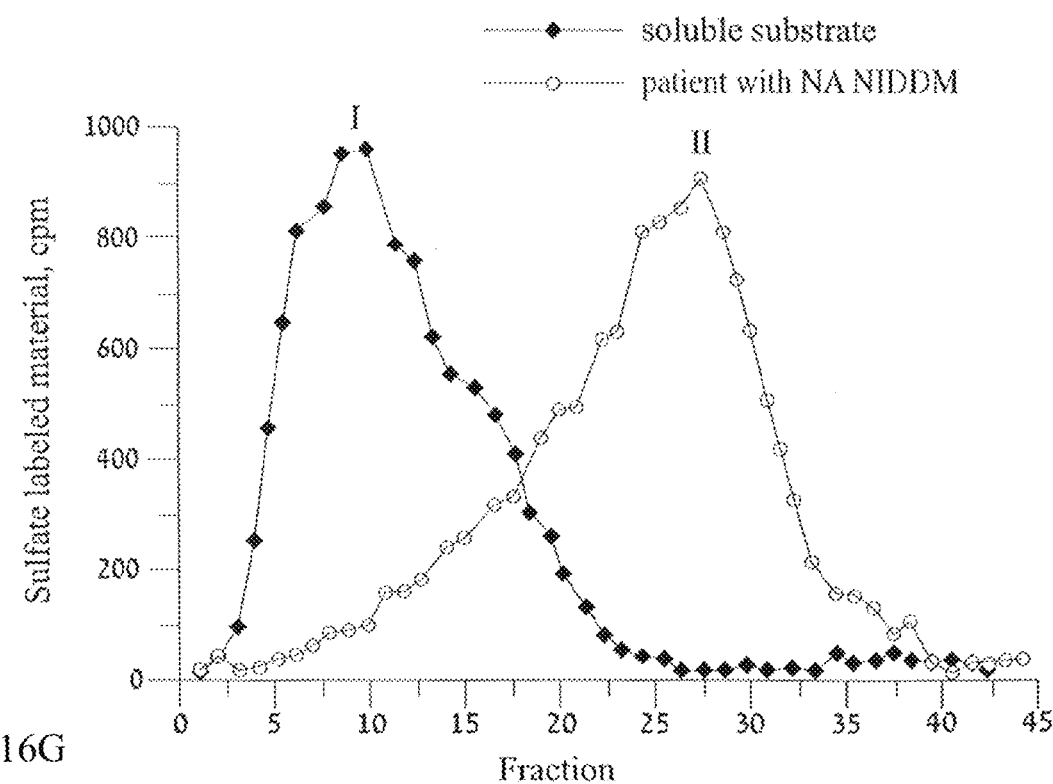
Figure 16H:
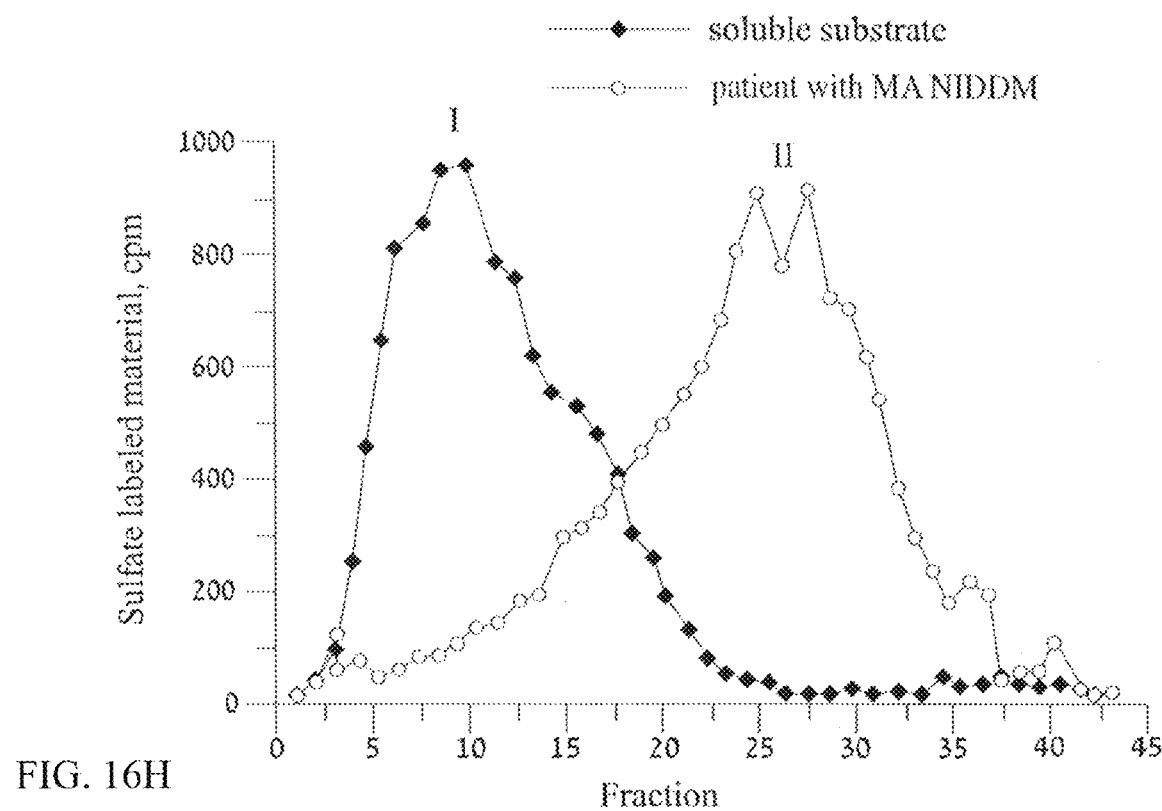

Heparanase activity was also detected in the urine of proteinuric patients not suffering from diabetes (FIGS. 16e-f). These included patients with focal segmental glomerulosclerosis, minimal change nephrotic syndrome and congenital nephrotic syndrome, thus indicating that the involvement of heparanase in the generation of proteinuria may not be limited to diabetic nephropathy. Urinary heparanase activity seems to be detected more frequently as the degree of proteinuria increases. Active heparanase was detected in the urine of 15% of normoalbuminuric and 25% microalbuminuric type I diabetic patients. The prevalence reached 48% in a group of 28 macroalbuminuric patients with NIDDM.

Diabetic nephropathy, occurring in approximately 30% of patients with type I diabetes, is a major cause of end stage renal disease. The inability to discriminate the subpopulation that will develop renal damage prior to the appearance of microalbuminuria, 10-15 years following the diagnosis of diabetes, prevents us from significantly changing the devastating natural history of the disease. Urinary heparanase activity is a distinguishing feature, occurring in 30-35% of normoalbuminuric females, within an otherwise homogenous group of patients.

This is the first result suggesting a role for heparanase in the pathogenesis of proteinuria in type I diabetes. Obviously, measurements of urinary heparanase activity is both time consuming and not sensitive enough. Moreover, we have demonstrated the presence of an inhibitor of mammalian heparanase in the urine of normal individuals. The nature of this inhibitory substance, possibly urinary glycosaminoglycans is currently being studied. Urinary heparanase activity is therefore the result of a balance between the presence in the urine of the enzyme and its inhibitor(s). Immunodetection of the heparanase protein is therefore a more sensitive and straightforward approach for diagnostic purposes. Altogether, our results clearly indicate that anti-heparanase antibodies that identify the heparanase antigen can be applied for early diagnosis of cancer metastasis and renal diseases. As discussed above, it is conceivable that heparanase may overcome the filtration barrier of the glomerular basement membrane and ECM simply by virtue of its ability to degrade the HS moieties that are held responsible for their permeaselective properties. Urinary heparanase is therefore expected to reflect the presence of heparanase in the circulation and hence be a sensitive marker for metastatic, inflammatory and kidney disease. Of particular significance is the potential ability to follow the course of tumor progression and spread, response to anti-cancer treatments, and possible relapse of the disease in a given patient. Targeted drug delivery and therapy are another aspect of the use for such antibodies.

Figure 17A:
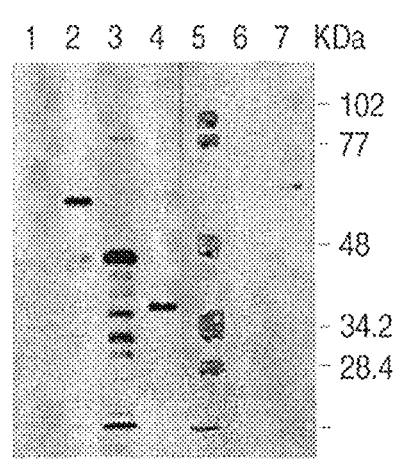
FIGS. 17a-b demonstrate Western blots of extracts of cells expressing various segments of heparanase as detected with polyclonal anti heparanase antibodies. 17a—antiserum from rabbit 7640, 17b—antiserum from rabbit 7644. Lane 1, E. coli BL21 (DE3)pLysS cells transfected with pRSET, lane 2, E. coli BL21 (DE3)pLysS cells transfected with pRSET containing the heparanase entire open reading frame (543 amino acids, SE ID NOs: 2 and 3), lane 3, E. coli BL21(DE3)pLysS cells transfected with pRSEThpaBK containing 414 amino acids of the heparanase open reading frame (amino acids 130-543 of SEQ ID NOs: 2 and 3), lane 4, E. coli BL21(DE3) pLysS cells transfected with pRSEThpaBH containing 302 amino acids of the heparanase open reading frame (amino acids 130-431 of SEQ ID NOs: 2 and 3), lane 5, molecular size markers, lane 6, medium of Sf21 insect cells infected with recombinant Baculovirus pFhpa containing the heparanase entire open reading frame (543 amino acids, SEQ ID NOs: 2 and 3), lane 7, Sf21 insect cells infected with recombinant baculovirus with no insert. Proteins were separated on 10% SDS-PAGE, antisera were diluted 1:1,000. Detection was performed by ECL (Amersham) according to the manufacturer's instructions. Size in kDa is shown to the right, as was determined using prestained SDS-PAGE standards, Bio-Rad, CA.
Figure 17B:
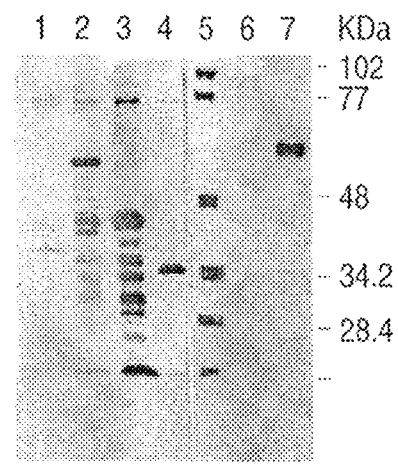

Anti-heparanase polyclonal antibodies: Antisera from two immunized rabbits were examined by western blot for reactivity with various segments of recombinant heparanase expressed in E. coli and with the Baculovirus expressed heparanase (FIGS. 17a-b). In both cases, the polyclonal antibody recognized proteins of the expected size in E. coli derived recombinant heparanase, about 60 kDa for the entire open reading frame (lanes 2), about 45 kDa for the 414 amino acids BamHI-KpnI hpa fragment (lanes 3) and 35 kDa for the 302 amino acids encoded by a BamHI-HindIII hpa fragment (lanes 4). A protein of approximately 65 kDa was recognized in the medium of Sf21 insect cells infected with recombinant Baculovirus pFhpa (lanes 7).

The specificity of affinity purified polyclonal antibodies was determined by Western blot with recombinant heparanase expressed in various expression systems, baculovirus infected insect cells, the yeast Pichia pastoris and CHO cells transfected with the hpa cDNA. For details about the CHO and Pichia clones see U.S. patent application Ser. No. 09/071,618, which is incorporated by reference as if fully set forth herein.

Figure 18:
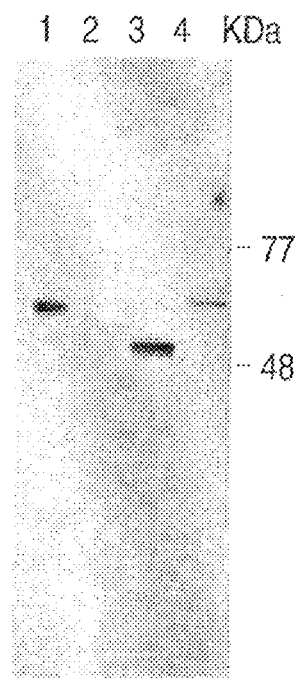
FIG. 18 demonstrates Western blot using affinity purified polyclonal antibodies with heparanase expressed in various expression systems. Lane 1, medium of Sf21 insect cells infected with recombinant Baculovirus pFhpa, lane 2, cell extract of a Chinese hamster ovary (CHO) clone stably transfected with a vector containing no insert, lane 3, cell extract of a CHO stable clone transfected with hpa cDNA, lane 4, proteins precipitated from medium of the yeast Pichia pastoris transfected with hpa cDNA. Proteins were separated on 4-20% gradient SDS-PAGE, antibody was diluted 1:100. Detection was performed by ECL (Amersham) according to the manufacturer's instructions. For CHO and Pichia clones see U.S. patent application Ser. No. 09/071,618, which is incorporated by reference as if fully set forth herein. Size in kDa is shown to the right, as was determined using prestained SDS-PAGE standards, Bio-Rad, CA.

The specificity of the purified antibody is demonstrated in FIG. 18. The purified antibody identified a single about 65 kDa protein expressed by Pichia pastoris (FIG. 18, lane 4), and a major band of similar size expressed by Sf21 cells infected with recombinant baculovirus (FIG. 18, lane 1). In a CHO stable transfected clone, 65 kDa and 50 kDa bands are detected (FIG. 18, lane 3) as compared with the negative control (FIG. 18, lane 2). In several experiments the two forms of the recombinant heparanase were identified, the higher form appeared as 60 to 65 kDa and the lower form as 45 to 50 kDa. Antibody 7644 was more specific and detected mainly the bands of the recombinant heparanase. 7460 detected several other cross reactive bands.

Figure 19A:
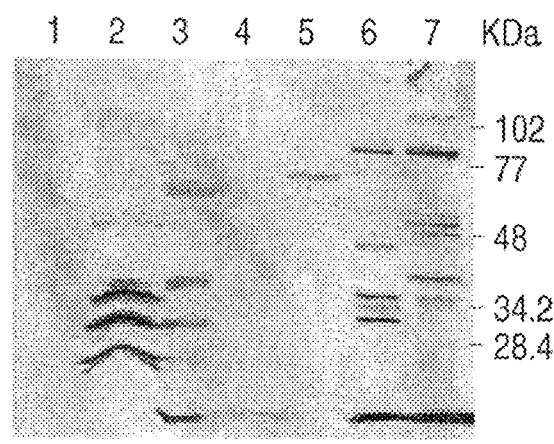
FIGS. 19a-b demonstrate Western blot of extracts of various cell types using anti-heparanase polyclonal antibodies. 19a—crude antiserum diluted 1:2,000, 19b—affinity purified antibodies diluted 1:100. lane 1, purified heparanase from placenta, lanes 2 and 3, cell extracts of platelets, insoluble and soluble fractions, respectively, lanes 4 and 5, cell extracts of neutrophils, insoluble and soluble fractions, respectively, lanes 6 and 7, cell extracts of mouse melanoma B16-F1 cells, insoluble and soluble fractions, respectively. Proteins were separated on 8-16% gradient gel. Detection was performed by ECL (Amersham) according to the manufacturer's instructions. Size in kDa is shown to the right, as was determined using prestained SDS-PAGE standards, Bio-Rad, CA.
Figure 19B:
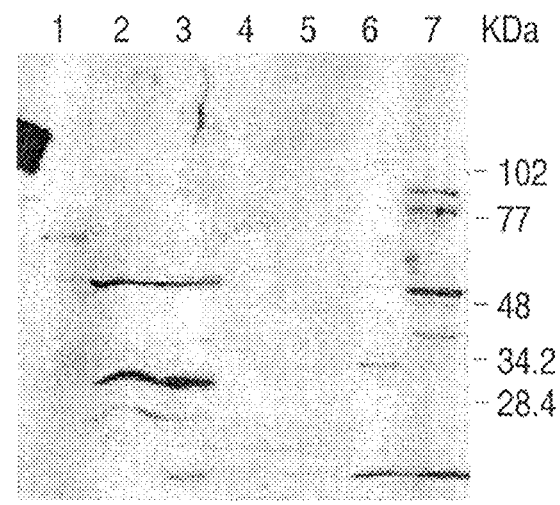

As shown in FIG. 19a, crude polyclonal antibodies recognized multiple bands in human platelets (lanes 2 and 3) and neutrophils cell extracts (lanes 4 and 5), as well as mouse melanoma cell line B16 (lanes 6 and 7). However, as shown in FIG. 19b, affinity purified antibodies recognized the 65 kDa and 50 kDa forms of heparanase purified from placenta (lane 1), two major bands in platelets extract, an upper band of approximately 50 kDa which corresponds with the lower band of the purified protein and a lower band of about 30 kDa (lanes 2 and 3). The 50 kDa protein appears in mouse melanoma cells as well as two bands of a higher molecular weight and several minor bands, which represent cross reactive proteins or other species of heparanase (lanes 6 and 7).

Monoclonal antibodies: Eight hundreds hybridomas, generated following 3 fusions were screened by ELISA for reactivity against human heparanase (native and denatured). Eight positive hybridomas were selected. Table 3 below summarizes the characteristics of the 8 hybridomas.

TABLE 3

Relative reactivity of hybridomas supernatants with native and denatured recombinant human heparanase

| Hybridoma | ELISA Native | ELISA Denature | Western blotting |
| --- | --- | --- | --- |
| HP-6 | − | + | n.d. |
| HP-40 | +++ | ++ | n.d. |
| HP-45 | + | ++ | n.d. |
| HP-92 | ++ | +++ | n.d./ |
| HP-117 | ++++ | +++ | 60, 45, 42 kDa |
| HP-130 | ++++ | +++ | n.d. |
| HP-239 | ++++ | +++ | n.d. |
| HP-303 | − | ++ | n.d. | n.d.—not determined

Figure 20:
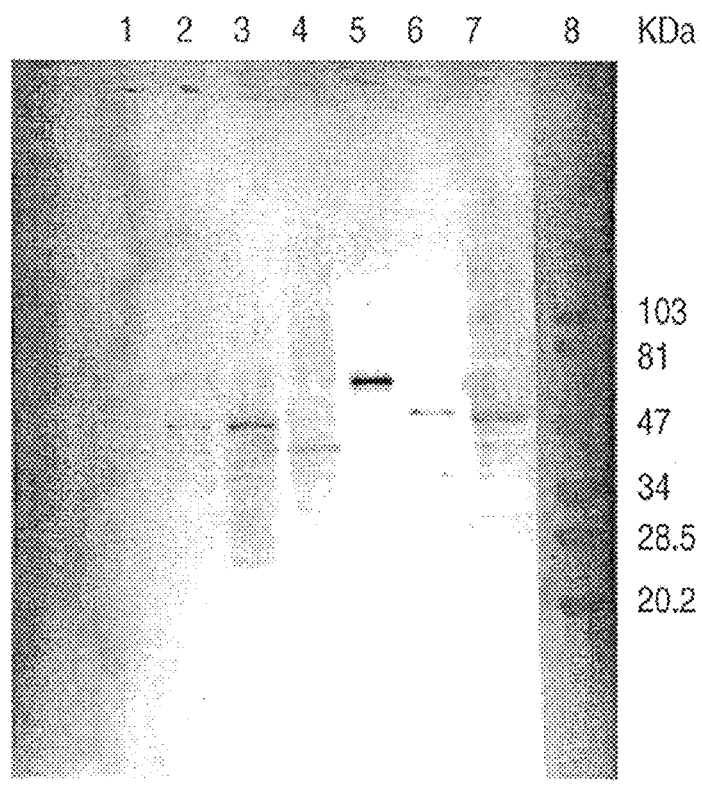
FIG. 20 demonstrates Western blot of recombinant and native heparanases from various origins using supernatant of hybridoma HP-117. Lanes 1 and 2, 293 human kidney cells non-transfected and transfected with hpa-pCDNA, respectively (15 µg), lane 3, CHO cells stably transfected with pShpa (40 µg), lane 4, mock transfected CHO cells (40 µg), lane 5, purified recombinant heparanase produced by baculovirus infected insect cells (50 ng), lane 6, cell extracts of E. coli expressing recombinant heparanase (50 ng), lane 7, cell extract of human platelets (100 µg), lane 8, prestained SDS-PAGE standard, Bio-Rad, CA. Proteins were separated on 4-20% gradient SDS-PAGE and transferred to a nylon membrane (Amersham). Membrane was incubated with supernatant of hybridoma Hp117 and detection was performed with alkaline phosphatase conjugated anti-mouse IgG antibodies.
Figures 21A, 21B:
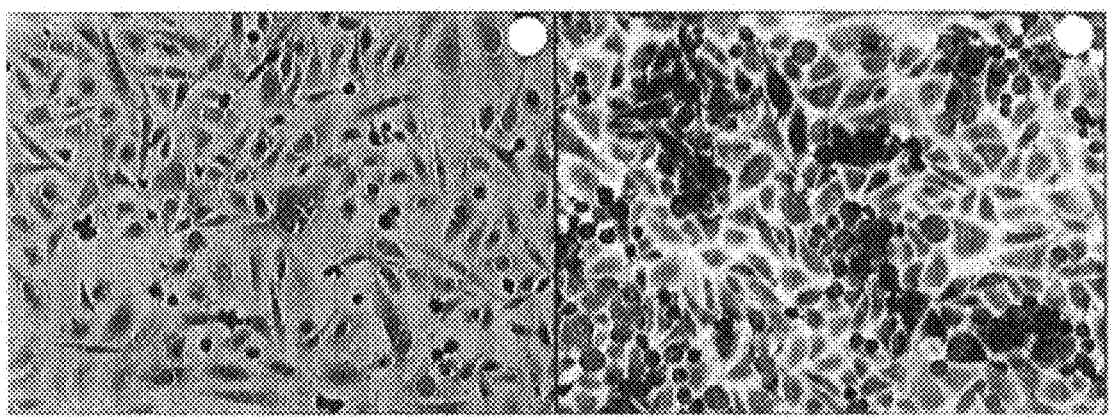
FIGS. 21a-b demonstrate immunostaining of heparanase in CHO cells with polyclonal antibodies. CHO cells transfected with the full length hpa gene (21a) were tested for overexpression of heparanase. Staining is detected in the cytoplasm of transfected cells. In non transfected CHO cells (21b), no staining of heparanase is detected.
Figures 22A, 22B:
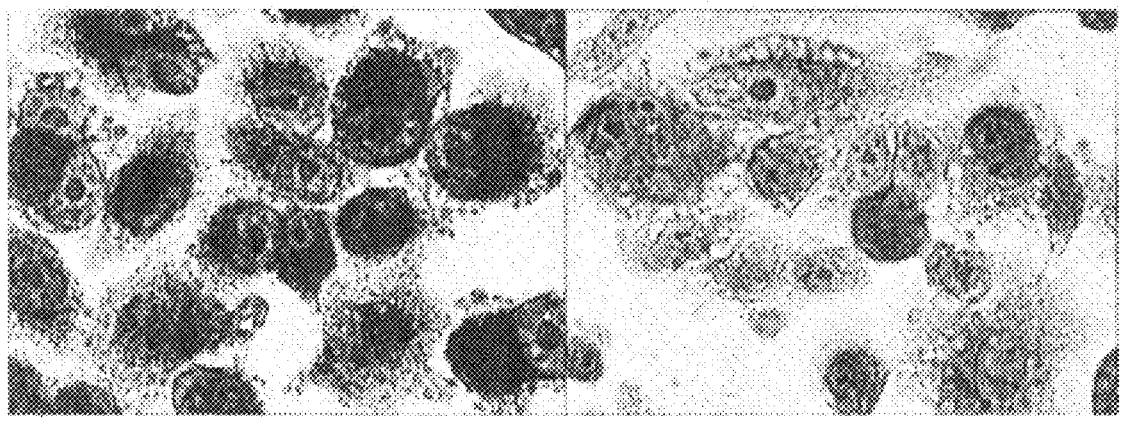
FIGS. 22a-b demonstrate immunostaining of heparanase in CHO cells with monoclonal antibody HP-130. CHO cells transfected with the full length hpa gene (22a) were tested for overexpression of heparanase. Staining is detected in the cytoplasm of transfected cells. In non transfected CHO cells (22b), no staining of heparanase is detected.
Figures 23A, 23B, 23C:
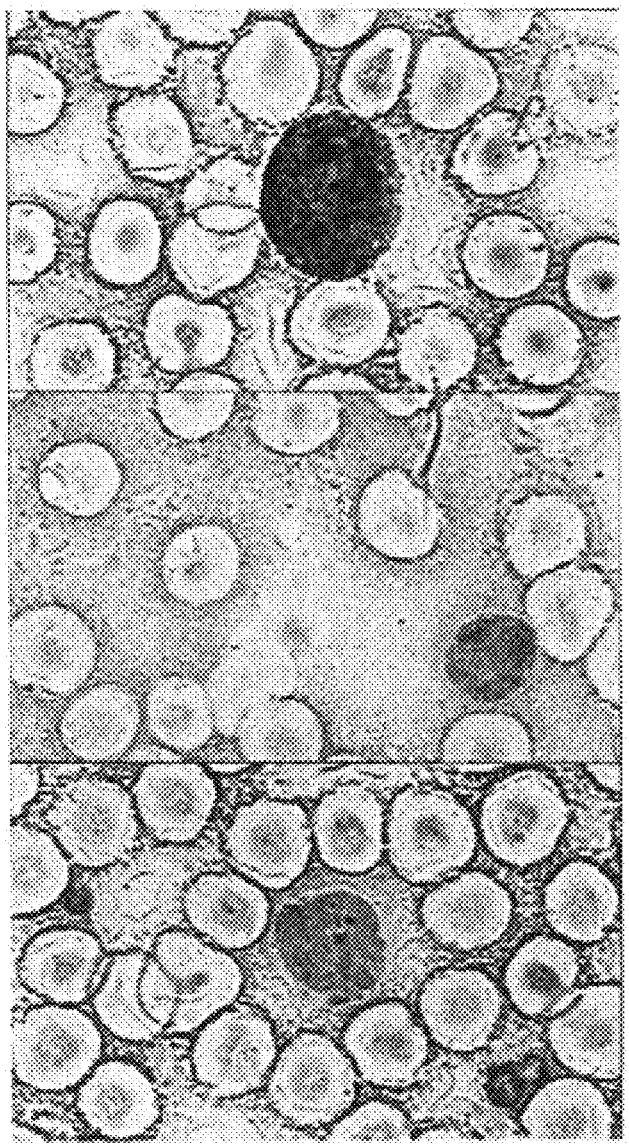
FIGS. 23a-c demonstrate immunostaining of heparanase in blood smears from normal donor with monoclonal antibody HP-92. Heparanase is found in the cytoplasm of neutrophils (23a) and platelets (23c) but is not detected in lymphocytes (23b) and monocytes (23c).

Immunoblot of native and recombinant heparanase expressed in various cell types was performed using the supernatant of hybridoma HP-117 (FIG. 20). A major band of approximately 50 kDa was detected in extract of stably transfected CHO cells (lane 3) and in platelets extract (lane 6). This band is also detected in transfected 293 cells as compared to the negative control (lanes 2 and 1 respectively). A band of approximately 42 kDa was observed in all mammalian cell extracts, including the negative control. This band probably represent a cross reactive protein or an endogenous form of heparanase. The 65 kDa recombinant heparanase purified from medium of baculovirus infected insect cells is clearly observed in lane 5 as well as a band of 53 kDa in lane 6 which is the expected size of the 508 amino acids heparanase polypeptide expressed in the E. coli. cells Both polyclonal and monoclonal antibodies were used successfully for detection of heparanase in intact cells by immunohistochemistry. Polyclonal antibodies showed specific staining of CHO cells transfected with pShpaCdhfr expression vector as described in U.S. patent application Ser. No. 09/071,618, which is incorporated by reference as if fully set forth herein, as compared with no staining of the non-transfected CHO cells (FIGS. 21a-b). Similar results were obtained with several monoclonal antibodies. FIGS. 22a-b demonstrate the specific staining of heparanase in the cytoplasm of transfected CHO cells, with supernatant of hybridoma HP-130. No staining was observed in non-transfected cells. Monoclonal antibody HP-92 showed a specific staining of neutrophils and platelets in blood smear of a healthy donor (FIGS. 23a-c). This expression pattern is consistent with the high levels of heparanase activity characteristic of these cells.

Availability of anti-heparanase antibodies will enable development of immunological assays for screening tissue and body fluids for heparanase. An ELISA will provide a more sensitive and convenient means of detection as compared to the currently available assays of heparanase activity which do not appear sensitive enough for the detection of the enzyme in non-concentrated plasma and body fluids.

ELISA will provide a powerful diagnostic tool for quantitative determination of heparanase concentrations in serum, plasma, urine and other biological fluids.

Although platelets and activated cells of the immune system (11) can express heparanase activity under certain conditions, we have detected little or no heparanase activity in normal human plasma. The possibility arises that with cancer patients, particularly those with leukemia and lymphoma, heparanase is secreted into the blood stream. In fact, our studies indicate that both acute and chronic human myeloid leukemic cells (AML and CML), but not chronic lymphocytic leukemic cells (CLL), secrete substantial amounts of heparanase during short incubation in PBS at 4° C.

As described above, elevated levels of heparanase were detected in sera from metastatic tumor bearing animals and melanoma patients (13) and in tumor biopsies of cancer patients (15). High levels of heparanase activity were measured in the urine of patients with aggressive metastatic disease and there was no detectable activity in the urine of healthy donors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES CITED

1. Wight, T. N., Kinsella, M. G., and Qwarnstromn, E. E. (1992). The role of proteoglycans in cell adhesion, migration and proliferation. Curr. Opin. Cell Biol. 4: 793-801.
2. Jackson, R. L., Busch, S. J., and Cardin, A. L. (1991). Glycosaminoglycans: Molecular properties, protein interactions and role in physiological processes. Physiol. Rev. 71: 481-539.
3. Wight, T. N. (1989). Cell biology of arterial proteoglycans. Arteriosclerosis 9: 1-20.
4. Kjellen, L., and Lindahl, U. (1991). Proteoglycans: structures and interactions. Annu. Rev. Biochem. 60: 443-475.
5. Ruoslahti, E., and Yamaguchi, Y. (1991). Proteoglycans as modulators of growth factor activities. Cell 64: 867-869.
6. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327-343. Academic press Inc., Orlando, Fla.
7. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis 12: 112-127.
8. Vlodavsky, I., Mohsen, M., Lider, O., Ishai-Michaeli, R., Ekre, H.-P., Svahn, C. M., Vigoda, M., and Peretz, T. (1995). Inhibition of tumor metastasis by heparanase inhibiting species of heparin. Invasion & Metastasis 14: 290-302.
9. Nakajima, M., Irimura, T., and Nicolson, G. L. (1988). Heparanase and tumor metastasis. J. Cell. Biochem. 36: 157-167.
10. Liotta, L. A., Rao, C. N., and Barsky, S. H. (1983). Tumor invasion and the extracellular matrix. Lab. Invest. 49: 639-649.
11. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res. 43: 2704-2711.
12. Vlodavsky, I., Ishai-Michaeli, R., Bar-Ner, M., Fridman, R., Horowitz, A. T., Fuks, Z. and Biran, S. (1988). Involvement of heparanase in tumor metastasis and angiogenesis. Is. J. Med. 24: 464-470.
13. Parish, C. R., Coombe, D. R., Jakobsen, K. B., and Underwood, P. A. (1987). Evidence that sulphated polysaccharides inhibit tumor metastasis by blocking tumor cell-derived heparanase. Int. J. Cancer 40: 511-517.
14. Vlodavsky, I., Liu, G. M., and Gospodarowicz, D. (1980). Morphological appearance, growth behavior and migratory activity of human tumor cells maintained on extracellular matrix vs. plastic. Cell 19: 607-616.
15. Gospodarowicz, D., Delgado, D., and Vlodavsky, I. (1980). Permissive effect of the extracellular matrix on cell proliferation in-vitro. Proc. Natl. Acad. Sci. USA 77: 4094-4098.
16. Burgess, W. H., and Maciag, T. (1989). The heparin-binding (fibroblast) growth factor family of proteins. Annu. Rev. Biochem. 58: 575-606.
17. Folkman, J., and Klagsbrun, M. (1987). Angiogenic factors. Science 235: 442-447.
18. Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci. 16: 268-271.
19. Cardon-Cardo, C., Vlodavsky, I., Haimovitz-Friedman, A., Hicklin, D., and Fuks, Z. (1990). Expression of basic fibroblast growth factor in normal human tissues. Lab. Invest. 63: 832-840.
20. Ishai-Michaeli, R., Eldor, A., and Vlodavsky, I. (1990). Heparanase activity expressed by platelets, neutrophils and lymphoma cells releases active fibroblast growth factor from extracellular matrix. Cell Reg. 1: 833-842.
21. Campbell, K. H., Rennick, R. E., Kalevich, S. G., and Campbell, G. R. (1992) Exp. Cell Res. 200: 156-167.
22. Oosta, G. M., Favreau, L. V., Beeler, D. L., and Rosenberg, R. D. (1982) Purification and properties of human platelets heparitinase. J. Biol. Chem. 257: 11,249-11,255.
23. Hoogewerf, A. J., Leone, J. W., Reardon, M., Howe, W. J., Asa, D., Heinrikson, R. L., and Ledbetter, S. R. (1995).

CXC chemokines connective tissue activating peptide-III and neutrophil activating peptide-2 are heparin/heparan sulfate-degrading enzymes. J. Biol. Chem. 270: 3268-3277.
24. Freeman, C., and Parish, C. R. (1988). Human platelet heparanase: Purification, characterization and catalytic activity. Biochem. J. 330:1341-1350.
25. Goshen, R., Hochberg, A., Korner, G., Levi, E., Ishai-Michaeli, R., Elkin, M., de Grot, N., and Vlodavsky, I. (1996) Purification and characterization of placental heparanase and its expression by cultured cytotrophoblasts. Mol. Human Reprod. 2: 679-684.
26. Jin, L., Nakajima, M. and Nicolson, G. L. (1990). Immunochemical localization of heparanase in mouse and human melanoma. Int. J. Cancer 45: 1088-1095.
26a. Mollinedo, F., Naagima, M., Leorens, A., Barbosa, e., Callejo, S., Gajate, C. and Fabras, a. (1997) Major co-localization of the extracellular-matrix degradative enzymes heparanase and gelatinase in tertiary granules of human neutrophils. Biochem. J. 327:917-923.
27. De Vouge, M. W., Yamazaki, A., Bennett, S. A. L., Chen, J.-H., Shwed, P. S., Couture, C., and Birnboim, H. C. (1994). Immuno selection of GRP94/endoplasmin from a KNRK cell specific λgt11 library using antibodies directed against a putative heparanase amino terminal peptide. Int. J. Cancer 56: 286-294.
28. Graham, L. D., and Underwood, P. A. (1996) Comparison of the heparanase enzyme from mouse melanoma cells, mouse macrophages and human platelets. Biochem. and Mol. Biol. International 39: 563-571.
29. Kosir, M. A., Quinn, C. C. V., Zukowski, K. L., Grignon, D. J., and Ledbetter, S. (1997) J. Surg. Res. 67: 98-105.
30. Kosir, M. A., Quinn, C. C. V., Pandey P., Berzinskas-Weller, E., Ledbetter, S. Fridman, R., and Wisscher, D. (1996) Cancer Res. 37: 495 (Ab. # 3378).
30a. Ernst, S., Langer, R., Cooney, Ch. L., and Sasisekharan, R. (1995) Enzymatic degradation of glycosaminoglycans. Critical Reviews in Biochemistry and Molecular Biology: 30(5): 387-444.
31. Gospodarowicz, D., Mescher, A. L., Birdwell, C. R. (1977). Stimulation of corneal endothelial cell proliferation in vitro by fibroblast and epidermal growth factors. Exp Eye Res 25: 75-89.
32. Haimovitz-Friedman, A., Falcone, D. J., Eldor, A., Schirrmacher, V., Vlodavsky, I., and Fuks, Z. (1991). Activation of platelet heparitinase by tumor cell derived factors. Blood 78: 789-796.
33. Yelton, D. E., Scharff, M. D. (1981). Monoclonal antibodies: a powerful new tool in biology and medicine. Annu. Rev. Biochem. 50: 657-680.
34. Friedmann, Y. and Daniel, C. W. (1996). Regulated expression of homeobox genes Msx-1 and Msx-2 in the mouse mammary gland suggests a role in epithelial-stromal interactions, hormone action and neoplasia. Devel. Biol. 177: 347-355.
35. Soule, H. D., Maloney, T. M., Wolman, S. R., Peterson, W. D., et al. (1990) Cancer Res. 50: 6075-6086.
36. Mill, F. R., Soul, H. D., Tait, L., Pauley, R. J., Wolman, S. R., Dawson, P. J., and Heppner, G. H. (1993) J. Nat. Cancer Inst. 85: 1725-1732.
37. Nakajima, M., Irimura, T., Di Ferrante, D., DiFerrante, N. and Nicolson, G. L. (1983) Heparan sulfate degradation: relation to tumor invasion and metastatic properties of mouse B16 melanoma sublines. Science 220: 611-613.

What is claimed is:

1. An antibody specifically binding an epitope of a heparanase protein, said heparanase protein comprising the amino acid sequence as set forth in SEQ ID NO:2, provided that phenylalanine replaces tyrosine at position 246.

2. The antibody of claim 1, wherein said heparanase protein consists of said amino acid sequence.

3. The antibody of claim 1, wherein said heparanase protein is recombinant.

4. The antibody of claim 1, wherein elicitation of the antibody is through in vivo or in vitro techniques, said antibody having been prepared by a process comprising the steps of:
   (a) exposing cells capable of producing antibodies to said at least one epitope of said heparanase protein and thereby generating antibody producing cells;
   (b) fusing said antibody producing cells with myeloma cells and thereby generating a plurality of hybridoma cells each producing monoclonal antibodies; and
   (c) screening said plurality of monoclonal antibodies to identify a monoclonal antibody which specifically binds heparanase.

5. The antibody of claim 1, wherein the antibody is selected from the group consisting of a polyclonal antibody and a monoclonal antibody.

6. The antibody of claim 5, wherein said polyclonal antibody is selected from the group consisting of a crude polyclonal antibody and an affinity purified polyclonal antibody.

7. An antibody elicited by an epitope of a heparanase protein, said heparanase protein comprising the amino acid sequence as set forth in SEQ ID NO:2, provided that phenylalanine replaces tyrosine at position 246.

8. The antibody of claim 7, wherein said heparanase protein consists of said amino acid sequence.

9. The antibody of claim 7, wherein said heparanase protein is recombinant.

10. The antibody of claim 7, wherein elicitation of the antibody is through in vivo or in vitro techniques, said antibody having been prepared by a process comprising the steps of:
    (a) exposing cells capable of producing antibodies to said at least one epitope of said heparanase protein and thereby generating antibody producing cells;
    (b) fusing said antibody producing cells with myeloma cells and thereby generating a plurality of hybridoma cells each producing monoclonal antibodies; and
    (c) screening said plurality of monoclonal antibodies to identify a monoclonal antibody which specifically binds heparanase.

11. The antibody of claim 7, wherein the antibody is selected from the group consisting of a polyclonal antibody and a monoclonal antibody.

12. The antibody of claim 11, wherein said polyclonal antibody is selected from the group consisting of a crude polyclonal antibody and an affinity purified polyclonal antibody.

* * * * *

SEQUENCE LISTING

```
<160> NUMBER OF SEQ ID NOS: 7

<210> SEQ ID NO 1
<211> LENGTH: 1721
<212> TYPE: DNA
<213> ORGANISM: Homo sapiens

<400> SEQUENCE: 1
ctagagcttt cgactctccg ctgcgcggca gctggcgggg ggagcagcca ggtgagccca      60
agatgctgct gcgctcgaag cctgcgctgc cgccgccgct gatgctgctg ctcctggggc     120
cgctgggtcc cctctcccct ggcgccctgc cccgacctgc gcaagcacag gacgtcgtgg     180
acctggactt cttcacccag gagccgctgc acctggtgag cccctcgttc ctgtccgtca     240
ccattgacgc caacctggcc acggacccgc ggttcctcat cctcctgggt tctccaaagc     300
ttcgtacctt ggccagaggc ttgtctcctg cgtacctgag gtttggtggc accaagacag     360
acttcctaat tttcgatccc aagaaggaat caacctttga agagagaagt tactggcaat     420
ctcaagtcaa ccaggatatt tgcaaatatg gatccatccc tcctgatgtg gaggagaagt     480
tacggttgga atggcgctac caggagcaat tgctactccg agaacactac cagaaaaagt     540
tcaagaacag cacctactca agaagctctg tagatgtgct atacactttt gcaaactgct     600
caggactgga cttgatcttt ggcctaaatg cgttattaag aacagcagat ttgcagtgga     660
acagttctaa tgctcagttg ctcctggact actgctcttc caagggtat aacatttctt      720 gggaactagg caatgaacct aacagtttcc ttaagaaggc tgatatttc atcaatgggt      780 cgcagttagg agaagattat attcaattgc ataaacttct aagaaagtcc accttcaaaa     840
```

```
atgcaaaact ctatggtcct gatgttggtc agcctcgaag aaagacggct aagatgctga      900
agagcttcct gaaggctggt ggagaagtga ttgattcagt tacatggcat cactactatt      960
tgaatggacg gactgctacc agggaagatt ttctaaaccc tgatgtattg acattttta      1020
tttcatctgt gcaaaaagtt ttccaggtgg ttgagagcac caggcctggc aagaaggtct     1080
ggttaggaga acaagctct gcatatggag gcggagcgcc cttgctatcc gacacctttg      1140
cagctggctt tatgtggctg ataaattgg gcctgtcagc ccgaatggga atagaagtgg      1200
tgatgaggca gtattctttt ggagcaggaa actaccattt agtggatgaa acttcgatc      1260
ctttacctga ttattggcta tctcttctgt tcaagaaatt ggtgggcacc aaggtgttaa     1320
tggcaagcgt gcaaggttca agagaagga agcttcgagt ataccttcat tgcacaaaca     1380
ctgacaatcc aaggtataaa gaaggagatt taactctgta tgccataaac ctccataacg     1440
tcaccaagta cttgcggtta ccctatcctt tttctaacaa gcaagtggat aaataccttc     1500
taagaccttt gggacctcat ggattacttt ccaaatctgt ccaactcaat ggtctaactc     1560
taaagatggt ggatgatcaa accttgccac ctttaatgga aaaacctctc cggccaggaa     1620
gttcactggg cttgccagct ttctcatata gttttttgt gataagaaat gccaaagttg     1680
ctgcttgcat ctgaaaataa aatatactag tcctgacact g                         1721

<210> SEQ ID NO 2
<211> LENGTH: 543
<212> TYPE: PRT
<213> ORGANISM: Homo sapiens

<400> SEQUENCE: 2

Met Leu Leu Arg Ser Lys Pro Ala Leu Pro Pro Leu Met Leu Leu
1               5                   10                  15

Leu Leu Gly Pro Leu Gly Pro Leu Ser Pro Gly Ala Leu Pro Arg Pro
                20                  25                  30

Ala Gln Ala Gln Asp Val Val Asp Leu Asp Phe Phe Thr Gln Glu Pro
            35                  40                  45

Leu His Leu Val Ser Pro Ser Phe Leu Ser Val Thr Ile Asp Ala Asn
        50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
                100                 105                 110

Glu Glu Arg Ser Tyr Trp Gln Ser Gln Val Asn Gln Asp Ile Cys Lys
            115                 120                 125

Tyr Gly Ser Ile Pro Pro Asp Val Glu Glu Lys Leu Arg Leu Glu Trp
        130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
        210                 215                 220
```

| | | | | | | | | | | | | | | |
|---|---|---|---|---|---|---|---|---|---|---|---|---|---|---|
|Glu|Pro|Asn|Ser|Phe|Leu|Lys|Lys|Ala|Asp|Ile|Phe|Ile|Asn|Gly|Ser|
|225| | | | |230| | | | |235| | | | |240|

Gln Leu Gly Glu Asp Tyr Ile Gln Leu His Lys Leu Leu Arg Lys Ser
            245                 250                 255

Thr Phe Lys Asn Ala Lys Leu Tyr Gly Pro Asp Val Gly Gln Pro Arg
        260                 265                 270

Arg Lys Thr Ala Lys Met Leu Lys Ser Phe Leu Lys Ala Gly Gly Glu
    275                 280                 285

Val Ile Asp Ser Val Thr Trp His His Tyr Tyr Leu Asn Gly Arg Thr
290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
        355                 360                 365

Leu Gly Leu Ser Ala Arg Met Gly Ile Glu Val Met Arg Gln Val
    370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Leu Val Gly Thr
                405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445

Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
    530                 535                 540

<210> SEQ ID NO 3
<211> LENGTH: 1721
<212> TYPE: DNA
<213> ORGANISM: Homo sapiens
<220> FEATURE:
<221> NAME/KEY: CDS
<222> LOCATION: (63)..(1691)

<400> SEQUENCE: 3
ctagagcttt cgactctccg ctgcgcggca gctggcgggg ggagcagcca ggtgagccca      60 ag atg ctg ctg cgc tcg aag cct gcg ctg ccg ccg ctg atg ctg             107
   Met Leu Leu Arg Ser Lys Pro Ala Leu Pro Pro Leu Met Leu
   1               5                   10                  15 ctg ctc ctg ggg ccg ctg ggt ccc ctc tcc cct ggc gcc ctg ccc cga        155
Leu Leu Leu Gly Pro Leu Gly Pro Leu Ser Pro Gly Ala Leu Pro Arg
                20                  25                  30

```
cct gcg caa gca cag gac gtc gtg gac ctg gac ttc ttc acc cag gag    203
Pro Ala Gln Ala Gln Asp Val Val Asp Leu Asp Phe Phe Thr Gln Glu
        35                  40                  45 ccg ctg cac ctg gtg agc ccc tcg ttc ctg tcc gtc acc att gac gcc    251
Pro Leu His Leu Val Ser Pro Ser Phe Leu Ser Val Thr Ile Asp Ala
    50                  55                  60 aac ctg gcc acg gac ccg cgg ttc ctc atc ctc ctg ggt tct cca aag    299
Asn Leu Ala Thr Asp Pro Arg Phe Leu Ile Leu Leu Gly Ser Pro Lys
65                  70                  75 ctt cgt acc ttg gcc aga ggc ttg tct cct gcg tac ctg agg ttt ggt    347
Leu Arg Thr Leu Ala Arg Gly Leu Ser Pro Ala Tyr Leu Arg Phe Gly
80                  85                  90                  95 ggc acc aag aca gac ttc cta att ttc gat ccc aag aag gaa tca acc    395
Gly Thr Lys Thr Asp Phe Leu Ile Phe Asp Pro Lys Lys Glu Ser Thr
                100                 105                 110 ttt gaa gag aga agt tac tgg caa tct caa gtc aac cag gat att tgc    443
Phe Glu Glu Arg Ser Tyr Trp Gln Ser Gln Val Asn Gln Asp Ile Cys
            115                 120                 125 aaa tat gga tcc atc cct cct gat gtg gag gag aag tta cgg ttg gaa    491
Lys Tyr Gly Ser Ile Pro Pro Asp Val Glu Glu Lys Leu Arg Leu Glu
        130                 135                 140 tgg ccc tac cag gag caa ttg cta ctc cga gaa cac tac cag aaa aag    539
Trp Pro Tyr Gln Glu Gln Leu Leu Leu Arg Glu His Tyr Gln Lys Lys
    145                 150                 155 ttc aag aac agc acc tac tca aga agc tct gta gat gtg cta tac act    587
Phe Lys Asn Ser Thr Tyr Ser Arg Ser Ser Val Asp Val Leu Tyr Thr
160                 165                 170                 175 ttt gca aac tgc tca gga ctg gac ttg atc ttt ggc cta aat gcg tta    635
Phe Ala Asn Cys Ser Gly Leu Asp Leu Ile Phe Gly Leu Asn Ala Leu
                180                 185                 190 tta aga aca gca gat ttg cag tgg aac agt tct aat gct cag ttg ctc    683
Leu Arg Thr Ala Asp Leu Gln Trp Asn Ser Ser Asn Ala Gln Leu Leu
            195                 200                 205 ctg gac tac tgc tct tcc aag ggg tat aac att tct tgg gaa cta ggc    731
Leu Asp Tyr Cys Ser Ser Lys Gly Tyr Asn Ile Ser Trp Glu Leu Gly
        210                 215                 220 aat gaa cct aac agt ttc ctt aag aag gct gat att ttc atc aat ggg    779
Asn Glu Pro Asn Ser Phe Leu Lys Lys Ala Asp Ile Phe Ile Asn Gly
    225                 230                 235 tcg cag tta gga gaa gat tat att caa ttg cat aaa ctt cta aga aag    827
Ser Gln Leu Gly Glu Asp Tyr Ile Gln Leu His Lys Leu Leu Arg Lys
240                 245                 250                 255 tcc acc ttc aaa aat gca aaa ctc tat ggt cct gat gtt ggt cag cct    875
Ser Thr Phe Lys Asn Ala Lys Leu Tyr Gly Pro Asp Val Gly Gln Pro
                260                 265                 270 cga aga aag acg gct aag atg ctg aag agc ttc ctg aag gct ggt gga    923
Arg Arg Lys Thr Ala Lys Met Leu Lys Ser Phe Leu Lys Ala Gly Gly
            275                 280                 285 gaa gtg att gat tca gtt aca tgg cat cac tac tat ttg aat gga cgg    971
Glu Val Ile Asp Ser Val Thr Trp His His Tyr Tyr Leu Asn Gly Arg
        290                 295                 300 act gct acc agg gaa gat ttt cta aac cct gat gta ttg gac att ttt   1019
Thr Ala Thr Arg Glu Asp Phe Leu Asn Pro Asp Val Leu Asp Ile Phe
    305                 310                 315 att tca tct gtg caa aaa gtt ttc cag gtg gtt gag agc acc agg cct   1067
Ile Ser Ser Val Gln Lys Val Phe Gln Val Val Glu Ser Thr Arg Pro
320                 325                 330                 335 ggc aag aag gtc tgg tta gga gaa aca agc tct gca tat gga ggc gga   1115
Gly Lys Lys Val Trp Leu Gly Glu Thr Ser Ser Ala Tyr Gly Gly Gly
                340                 345                 350
```

```
gcg ccc ttg cta tcc gac acc ttt gca gct ggc ttt atg tgg ctg gat    1163
Ala Pro Leu Leu Ser Asp Thr Phe Ala Ala Gly Phe Met Trp Leu Asp
        355                 360                 365 aaa ttg ggc ctg tca gcc cga atg gga ata gaa gtg gtg atg agg caa    1211
Lys Leu Gly Leu Ser Ala Arg Met Gly Ile Glu Val Val Met Arg Gln
        370                 375                 380 gta ttc ttt gga gca gga aac tac cat tta gtg gat gaa aac ttc gat    1259
Val Phe Phe Gly Ala Gly Asn Tyr His Leu Val Asp Glu Asn Phe Asp
    385                 390                 395 cct tta cct gat tat tgg cta tct ctt ctg ttc aag aaa ttg gtg ggc    1307
Pro Leu Pro Asp Tyr Trp Leu Ser Leu Leu Phe Lys Lys Leu Val Gly
400                 405                 410                 415 acc aag gtg tta atg gca agc gtg caa ggt tca aag aga agg aag ctt    1355
Thr Lys Val Leu Met Ala Ser Val Gln Gly Ser Lys Arg Arg Lys Leu
                420                 425                 430 cga gta tac ctt cat tgc aca aac act gac aat cca agg tat aaa gaa    1403
Arg Val Tyr Leu His Cys Thr Asn Thr Asp Asn Pro Arg Tyr Lys Glu
            435                 440                 445 gga gat tta act ctg tat gcc ata aac ctc cat aac gtc acc aag tac    1451
Gly Asp Leu Thr Leu Tyr Ala Ile Asn Leu His Asn Val Thr Lys Tyr
        450                 455                 460 ttg cgg tta ccc tat cct ttt tct aac aag caa gtg gat aaa tac ctt    1499
Leu Arg Leu Pro Tyr Pro Phe Ser Asn Lys Gln Val Asp Lys Tyr Leu
    465                 470                 475 cta aga cct ttg gga cct cat gga tta ctt tcc aaa tct gtc caa ctc    1547
Leu Arg Pro Leu Gly Pro His Gly Leu Leu Ser Lys Ser Val Gln Leu
480                 485                 490                 495 aat ggt cta act cta aag atg gtg gat gat caa acc ttg cca cct tta    1595
Asn Gly Leu Thr Leu Lys Met Val Asp Asp Gln Thr Leu Pro Pro Leu
                500                 505                 510 atg gaa aaa cct ctc cgg cca gga agt tca ctg ggc ttg cca gct ttc    1643
Met Glu Lys Pro Leu Arg Pro Gly Ser Ser Leu Gly Leu Pro Ala Phe
            515                 520                 525 tca tat agt ttt ttt gtg ata aga aat gcc aaa gtt gct gct tgc atc    1691
Ser Tyr Ser Phe Phe Val Ile Arg Asn Ala Lys Val Ala Ala Cys Ile
        530                 535                 540 tgaaaataaa atatactagt cctgacactg                                    1721

<210> SEQ ID NO 4
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 4
cgcatatgca ggacgtcgtg gacctg                                          26

<210> SEQ ID NO 5
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 5
tatgatcctc tagtacttct cgac                                            24

<210> SEQ ID NO 6
<211> LENGTH: 23
<212> TYPE: DNA
<213> ORGANISM: Artificial sequence
```

```
<220> FEATURE:
<223> OTHER INFORMATION: Single strand DNA oligonucleotide

<400> SEQUENCE: 6
ttcgatccca agaaggaatc aac                                            23

<210> SEQ ID NO 7
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 7
gtagtgatgc catgtaactg aatc                                           24
```